US010927108B2

(12) United States Patent
Hubin et al.

(10) Patent No.: US 10,927,108 B2
(45) Date of Patent: Feb. 23, 2021

(54) COMPOSITIONS COMPRISING MACROCYCLE DERIVATIVES INCORPORATING BRIDGED MACROCYCLES AND METHODS OF PRODUCING AND USING SAME

(71) Applicants: Southwestern Oklahoma State University, Weatherford, OK (US); University of Mississippi, University, MS (US)

(72) Inventors: Timothy J. Hubin, Weatherford, OK (US); M. O. Faruk Khan, Weatherford, OK (US); Stephen James Archibald, Hull (GB); Babu Lal Tekwani, Oxford, MS (US)

(73) Assignees: Southwestern Oklahoma State University, Weatherford, OK (US); University of Mississippi, University, MS (US)

( * ) Notice: Subject to any disclaimer, the term of this patent is extended or adjusted under 35 U.S.C. 154(b) by 130 days.

(21) Appl. No.: 15/753,409

(22) PCT Filed: Jul. 20, 2016

(86) PCT No.: PCT/US2016/043165
§ 371 (c)(1),
(2) Date: Feb. 19, 2018

(87) PCT Pub. No.: WO2017/030728
PCT Pub. Date: Feb. 23, 2017

(65) Prior Publication Data
US 2018/0251459 A1 Sep. 6, 2018

Related U.S. Application Data

(60) Provisional application No. 62/206,023, filed on Aug. 17, 2015.

(51) Int. Cl.
| | | |
|---|---|---|
| *C07D 471/00* | (2006.01) |
| *C07D 519/00* | (2006.01) |
| *A61K 31/4995* | (2006.01) |
| *A61K 31/55* | (2006.01) |
| *A61K 31/4985* | (2006.01) |
| *A61P 31/00* | (2006.01) |
| *C07D 401/04* | (2006.01) |
| *C07D 487/04* | (2006.01) |
| *A61K 45/06* | (2006.01) |
| *C07D 273/00* | (2006.01) |
| *G01N 33/58* | (2006.01) |
| *G01N 33/60* | (2006.01) |
| *A61P 31/04* | (2006.01) |
| *A61P 31/10* | (2006.01) |
| *A61K 33/30* | (2006.01) |
| *A61K 33/32* | (2006.01) |
| *A61K 33/34* | (2006.01) |

(52) U.S. Cl.
CPC ........ *C07D 471/00* (2013.01); *A61K 31/4985* (2013.01); *A61K 31/4995* (2013.01); *A61K 31/55* (2013.01); *A61K 45/06* (2013.01); *A61P 31/00* (2018.01); *C07D 273/00* (2013.01); *C07D 401/04* (2013.01); *C07D 487/04* (2013.01); *C07D 519/00* (2013.01); *G01N 33/582* (2013.01); *G01N 33/60* (2013.01); *A61K 33/30* (2013.01); *A61K 33/32* (2013.01); *A61K 33/34* (2013.01); *A61P 31/04* (2018.01); *A61P 31/10* (2018.01); *G01N 2800/26* (2013.01); *Y02A 50/30* (2018.01)

(58) Field of Classification Search
CPC .......................... A61K 31/4985; C07D 471/00
See application file for complete search history.

(56) References Cited

U.S. PATENT DOCUMENTS

| | | |
|---|---|---|
| 2002/0098149 A1 | 7/2002 | Liu |
| 2013/0309176 A1 | 11/2013 | Port et al. |

FOREIGN PATENT DOCUMENTS

| | | |
|---|---|---|
| WO | 200066112 | 11/2000 |
| WO | 2005121109 A2 | 12/2005 |
| WO | 2012019772 A1 | 2/2012 |

OTHER PUBLICATIONS

Extended European Search Report dated Dec. 11, 2018 in European Application No. 16837463.5, filed Jul. 20, 2016.
Sreedaran, et al.; "Synthesis, Electrochemical, Catalytic and Antimicrobial Activities of Novel Unsymmetrical Macrocyclic Dicompartmental Binuclear Nickel(II) Complexes," Polyhedron (2008), vol. 27, pp. 1867-1874.
Lars Ole Gerlach, et al.; "Molecular Interactions of Cyclam and Bicyclam Non-peptide Antagonists with the CXCR4 Chemokine Receptor," Journal of Biological Chemistry, American Society for Biochemistry and Molecular. Biology (2001), vol. 276, No. 17, pp. 14153-14160.
Esté, et al.; "Activity of Different Bicyclam Derivatives Against Human Immunodeficiency Virus Depends on Their Interaction with the CXCR4 Chemokine Receptor," Molecular Pharmaco, American Society for Pharmacology and Experimental Therapeutics (1999), vol. 55, No. 1, pp. 67-73.

(Continued)

*Primary Examiner* — Yong S. Chong
(74) *Attorney, Agent, or Firm* — Dunlap Codding, P.C.

(57) ABSTRACT

Compositions are disclosed herein that include macrocycle derivatives incorporating bridged macrocycles. Also disclosed are methods of producing and using the compositions.

24 Claims, 15 Drawing Sheets

(56) References Cited

OTHER PUBLICATIONS

Egberink, et al.; "Bicyclams, Selective Antagonists of the Human Chemokine Receptor CXCR4, Potently Inhibit Feline Immunodeficiency Virus Replication," Journal of Virology (1999), vol. 73, No. 8, pp. 6346-6352.
International Search Report, dated Dec. 8, 2016, in PCT/US2016/043165, filed Jul. 20, 2016.
Written Opinion of the International Searching Authority, dated Dec. 8, 2016, in PCT/US2016/043165, filed Jul. 20, 2016.
PUBCHEM, Substance Record for SID 78345586. Create Date Jun. 12, 2009; retrieved from internet on Nov. 3, 2016 at <https://pubchem.ncbi.nml.nih.gov/substance/78345586>.

DWDC04

NS11
Mn(L)Cl$_2$

BME07
[Co(L)(OAc)]PF$_6$ . H$_2$O

ANC26
[Ni(L)(OAc)]PF$_6$

TA17B
[Zn(L)(OAc)]PF$_6$

DJD29

FeLCl$_3$ · H$_2$O
SLK36

[Cu(L)(OAc)$_{0.4}$][PF$_6$]$_{1.6}$
AW040

[Ni(L)(OAc)]PF$_6$
DJD22

Ni(L)Cl$_2$ · 3H$_2$O
ADS20

[CoLCl$_2$]PF$_6$
DGJ031

KRW32

FeLCl₂
NS16

[Ni(L)(OAc)]PF₆
OB106

DJC55B

OB95A

[Co(L)(OAc)](PF₆)
OB118

2NO₃⁻

KS24
[Cu₂(L)(OAc)₂][PF₆]₂

OB45

CMB035
[Zn₂(L)(OAc)₂][PF₆]₂ · 3.3H₂O

OB30
[Co₂(L)(OAc)₂][PF₆]₂ · DMF

OB54
[Ni₂(L)][PF₆]₄

8HCl

OB34
[Cu₂(L)(OAc)₂][PF₆]₂ · 2H₂O

CMB029
[Cu₂(L)(OAc)₂][PF₆]₂

COMPOSITIONS COMPRISING MACROCYCLE DERIVATIVES INCORPORATING BRIDGED MACROCYCLES AND METHODS OF PRODUCING AND USING SAME

CROSS REFERENCE TO RELATED APPLICATIONS/INCORPORATION BY REFERENCE STATEMENT

This application is a US national stage application filed under 35 USC § 371 of International Application No. PCT/US2016/043165, filed Jul. 20, 2016; which claims benefit under 35 USC § 119(e) of U.S. Ser. No. 62/206,023, filed Aug. 17, 2015. The entire contents of the above-referenced patent applications are hereby expressly incorporated herein by reference.

STATEMENT REGARDING FEDERALLY SPONSORED RESEARCH OR DEVELOPMENT

This invention was made with government support under Contract Number P20RR016478 awarded by the National Institutes of Health IDeA Networks of Biomedical Research Excellence (INBRE) program. The government has certain rights in the invention.

BACKGROUND

AIDS patients, transplant recipients, and other immunocompromised individuals are susceptible to numerous opportunistic infections. One globally important type of opportunistic infection is caused by the fungal pathogen *Cryptococcus neoformans*. Initial pulmonary infection is believed to lead to Cryptococcal meningitis, which even if treated, is often fatal. The 10-week survival rate is only 70%, even with the best possible therapy. AIDS patients are even less likely to survive *C. neoformans* infections, with 10-week survival rates as low as 40%, making this pathogen a particularly significant threat in parts of the world where AIDS incidence is high. More than 500,000 deaths resulting from 1 million infections are reported each year, worldwide. In sub-Saharan Africa, *C. neoformans* infection has overtaken tuberculosis as the fourth leading imminent cause of death of AIDS patients by infectious disease.

Only a handful of antifungal drugs are effective against *C. neoformans*, and their use is often limited by drug toxicity and antifungal resistance issues. Amphotericin B (AMB) is a natural product antifungal that has been used successfully over the past 50 years to reduce the previous near 100% fatality of Cryptococcal infection to a success rate of 60-70% in non-AIDS patients. Unfortunately, treatment of AIDS patients with AMB alone drops the success rate to only 40%.

Leishmaniasis, another disease caused by infection with a pathogen (in this case, a parasite of the genus *Leishmania*), is among the major debilitating and devastating tropical diseases that are targets for the World Health Organization's special program Research and Training in Tropical Diseases (TDR) (Hyde (1990) *Molecular parasitology*. Milton Keynes: Open University press) and most recently the Drugs for Neglected Diseases initiative (Geneva, Switzerland). These diseases are caused by the parasites of the genus *Leishmania*. Table 1 gives an outline of the major human leishmaniasis with their global annual disease burdens (as of 1999) in terms of disability adjusted life years (DALY).

TABLE 1

The Major Leishmaniasis Diseases, Causative Agents, Their Global Burdens in Terms of Disability Adjusted Life Years (DALY), and Current Treatments

| Disease | Causative Agent(s) | DALY* (million/year) | Current Treatments |
|---|---|---|---|
| Visceral leishmaniasis or Kala azar | Leishmania donovani | 1.7 | Pentostam, glucantime |
| Dermal leishmaniasis or tropical sore | L. major, L. tropica, L. braziliensis, L. mexicana | | Pentamidine |

*Taken from World Health Report 1999, publ. World Health Organization Geneva (1999).

Pentavalent antimonials such as, but not limited to, pentostam or pentamidine are the recommended treatment for visceral leishmaniasis; however, these treatments are toxic, and the causative agents have developed resistance thereto (Croft (1988) *Trends. Pharmacol. Sci.*, 9:376-81; and Grogl et al. (1992) *Am. J. Trop. Med. Hyg.*, 47:117-26.). Relapse of the disease or only a partial response to the treatment are seen more commonly in leishmaniasis in Kenya, the Sudan, and India, as compared to Mediterranean or Latin American leishmaniasis; in these countries, a second or longer course of treatment is often needed.

Overall, the demand for chemotherapeutic agents for the treatment of leishmaniasis is desperate. Those needing treatment are mainly in impoverished rural and urban communities with poor housing and limited access to medical attention, and in countries where basic healthcare infrastructures have yet to be developed. Approved chemotherapies that are available were developed in the first half of the last century (suramine, pentamidine, arsenicals, and antimonials); some would fail today's more stringent standards for drug safety. Given the initial success of a largely empirical approach, progress in drug development in recent years has been poor, and undoubtedly there is great need for new treatments for human diseases by parasitic leishmanial that are less toxic than the treatments that are currently commercially available.

Certain macrocycle derivatives having bridged macrocycles incorporated therein have been identified. These certain macrocycle derivatives have been shown to act as anti-viral agents, CXCR4 chemokine receptor antagonists, and as biological imaging agents (see, for example, U.S. Pat. No. 8,034,800, issued to Archibald, Lewis, and Hubin on Oct. 11, 2011; the entire contents of which are hereby expressly incorporated herein by reference). However, only certain particular structures of this class of compounds have been identified, and the anti-microbial activity associated therewith is limited to the specific anti-viral activity disclosed in the above reference.

In the presently disclosed and/or claimed inventive concept(s), new and improved compositions that include novel macrocycle derivatives incorporating bridged macrocycles are disclosed. Surprisingly, it has been found that certain of these novel compounds possess one or more anti-microbial activities (including, but not limited to, an anti-fungal activity that is selectively effective against *C. neoformans*). Therefore, it is to such compositions, as well as methods of producing and using same, that the presently disclosed and/or claimed inventive concept(s) is directed.

DETAILED DESCRIPTION

Figure 1:
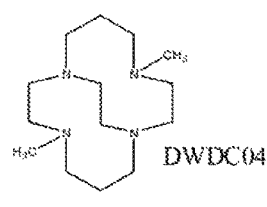
FIGS. 1, 2, 3, 4, 5, and 6 graphically depict non-limiting examples of specific structures of compositions in accordance with Formula (I) of the presently disclosed and/or claimed inventive concept(s).
Figure 1:
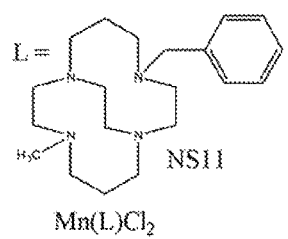
Figure 1:
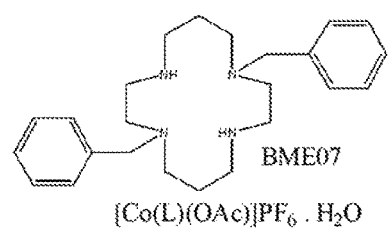
Figure 1:
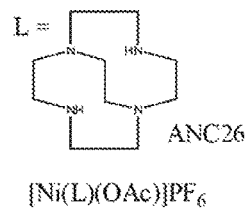
Figure 1:
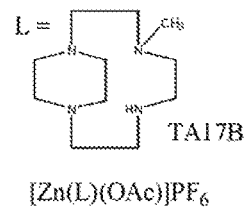
Figure 1:
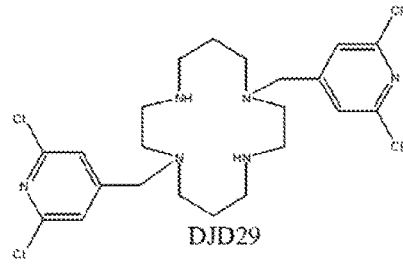
Figure 2:
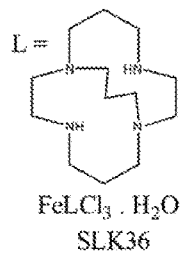
Figure 2:
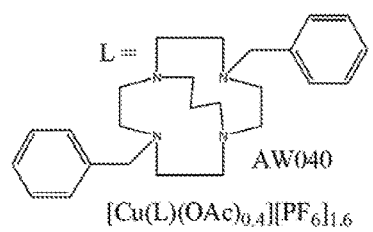
Figure 2:
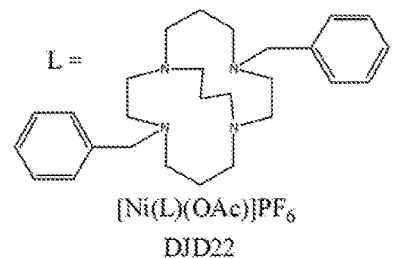
Figure 2:
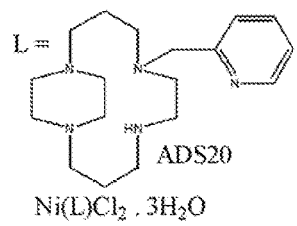
Figure 2:
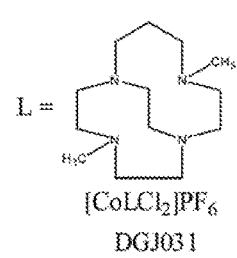
Figure 2:
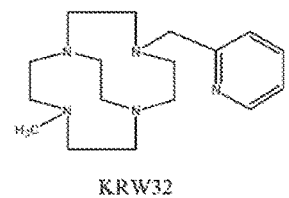
Figure 3:
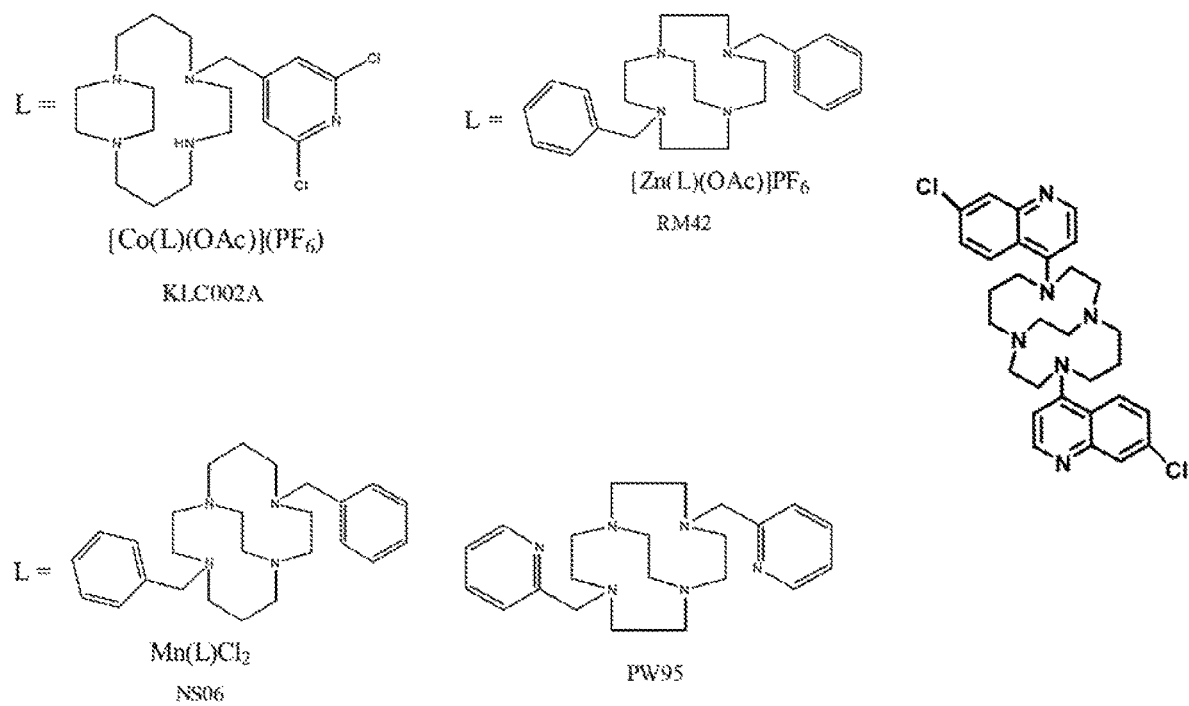
Figure 4:
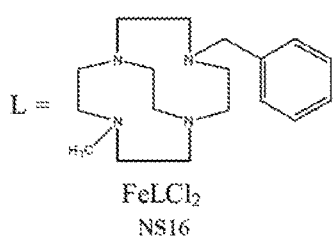
Figure 4:
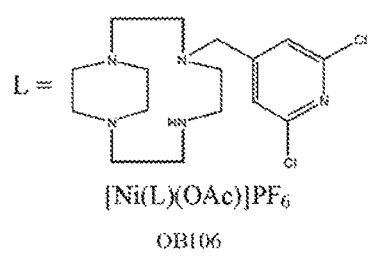
Figure 4:
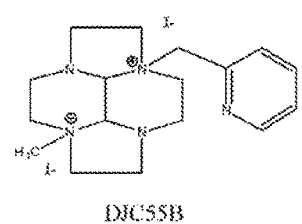
Figure 4:
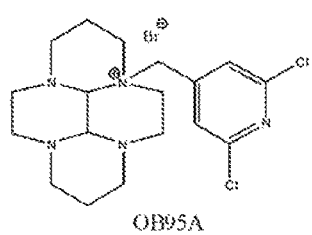
Figure 4:
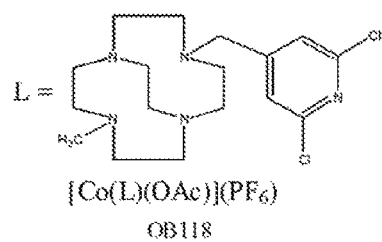
Figure 4:
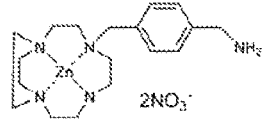
Figure 5:
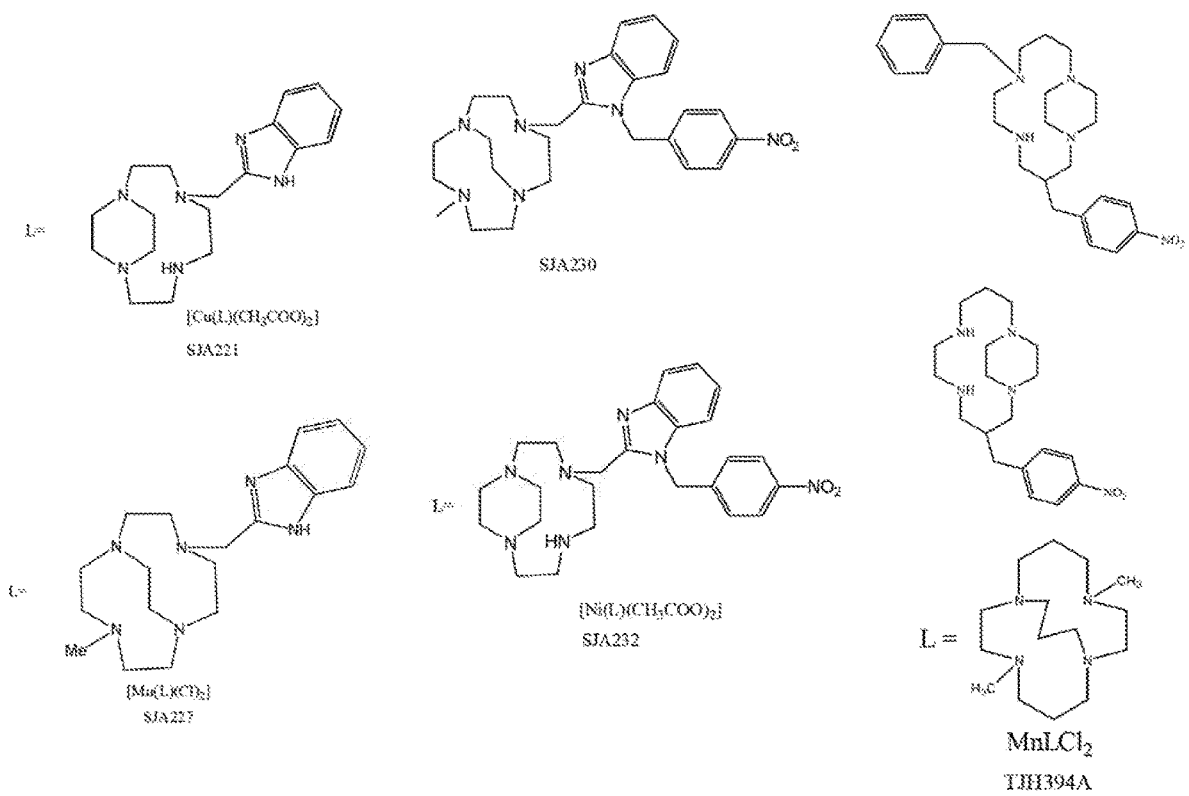
Figure 6:
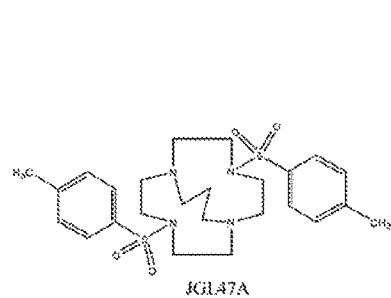
Figure 6:
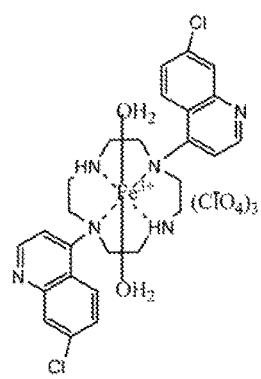
Figure 6:
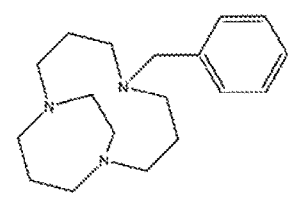
Figure 6:
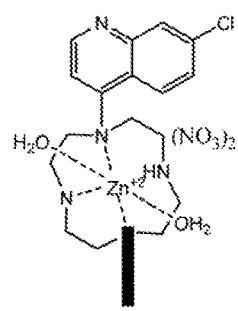
Figure 6:
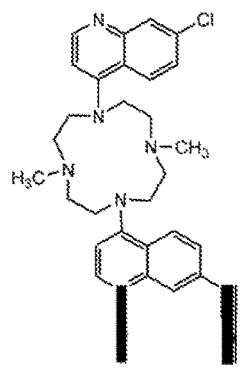
Figure 6:
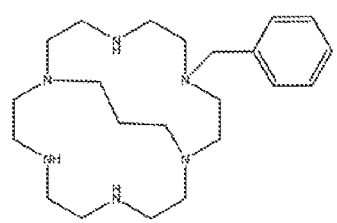
Figure 7:
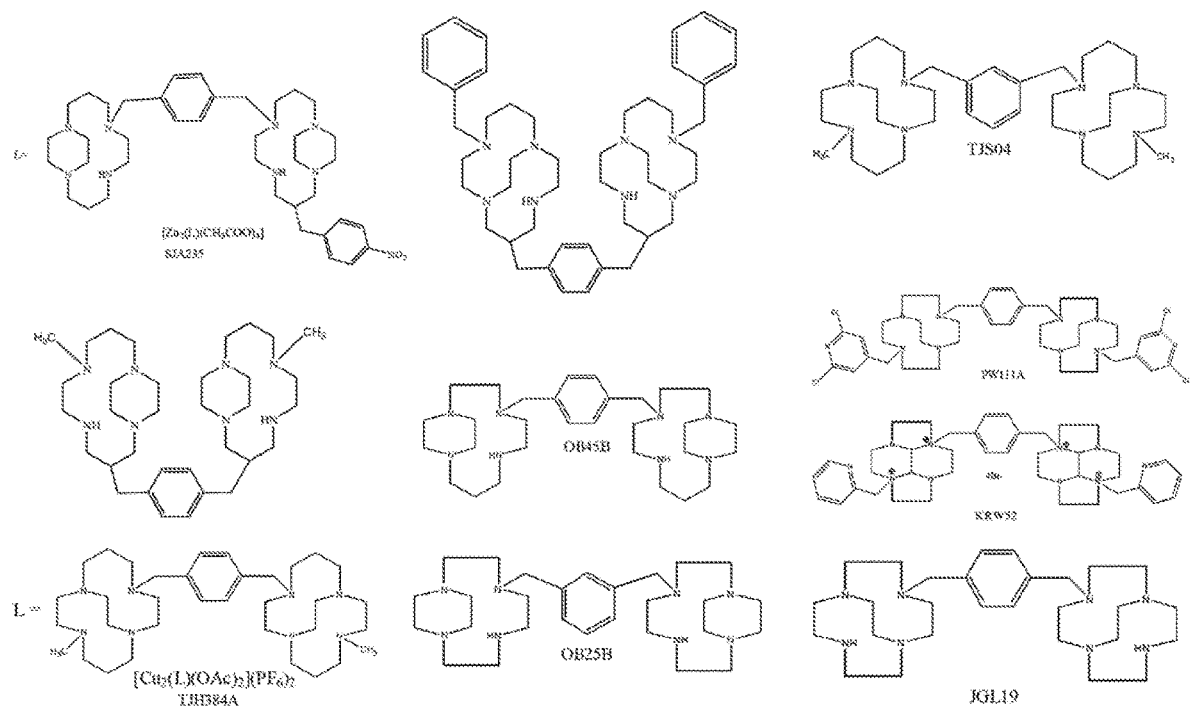
FIGS. 7, 8, 9, and 10 graphically depict non-limiting examples of specific structures of compositions in accordance with Formula (II) of the presently disclosed and/or claimed inventive concept(s).
Figure 8:
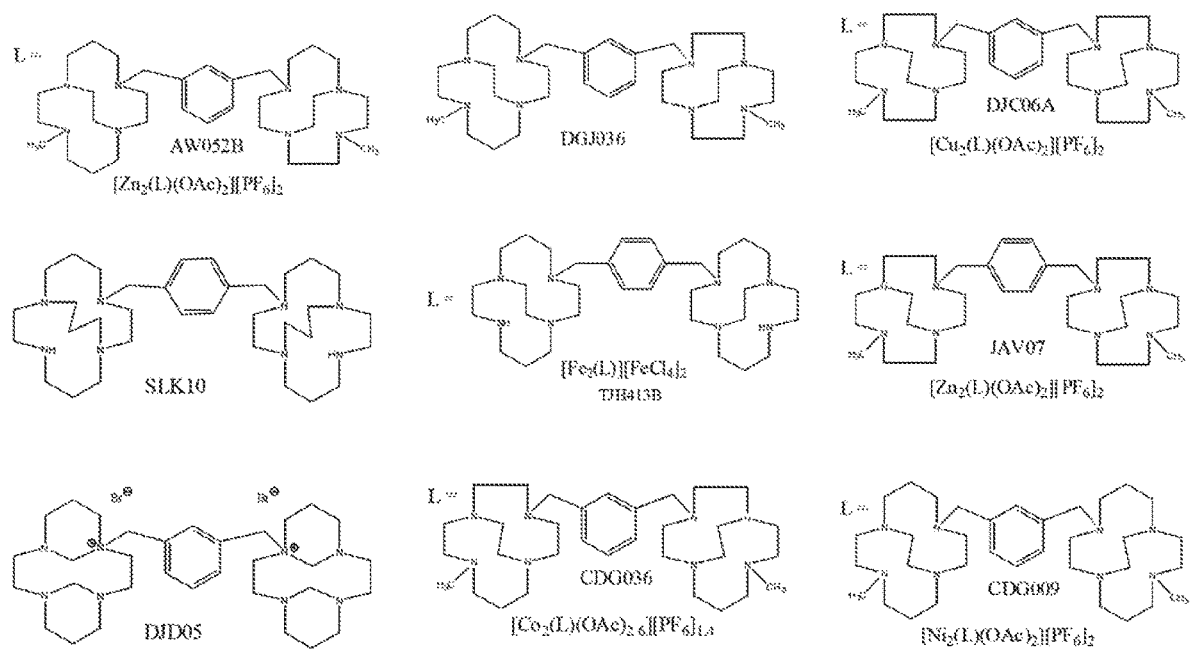
Figure 9:
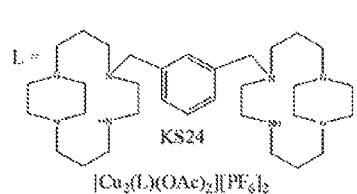
Figure 9:
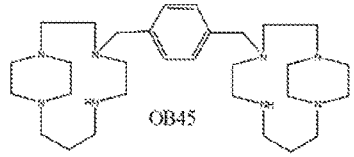
Figure 9:
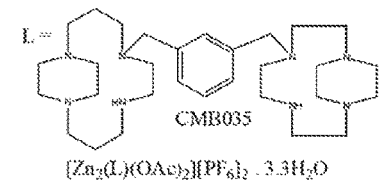
Figure 9:
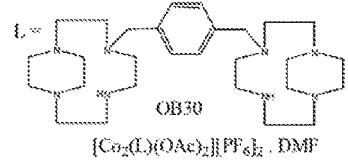
Figure 9:
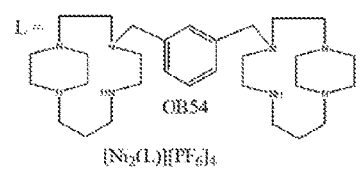
Figure 9:
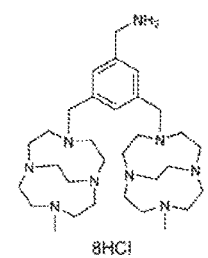
Figure 9:
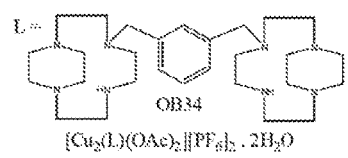
Figure 9:
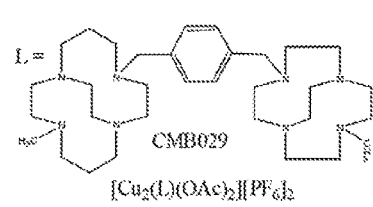
Figure 9:
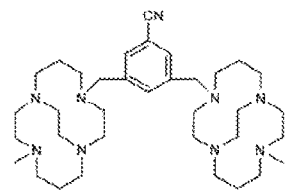
Figure 10:
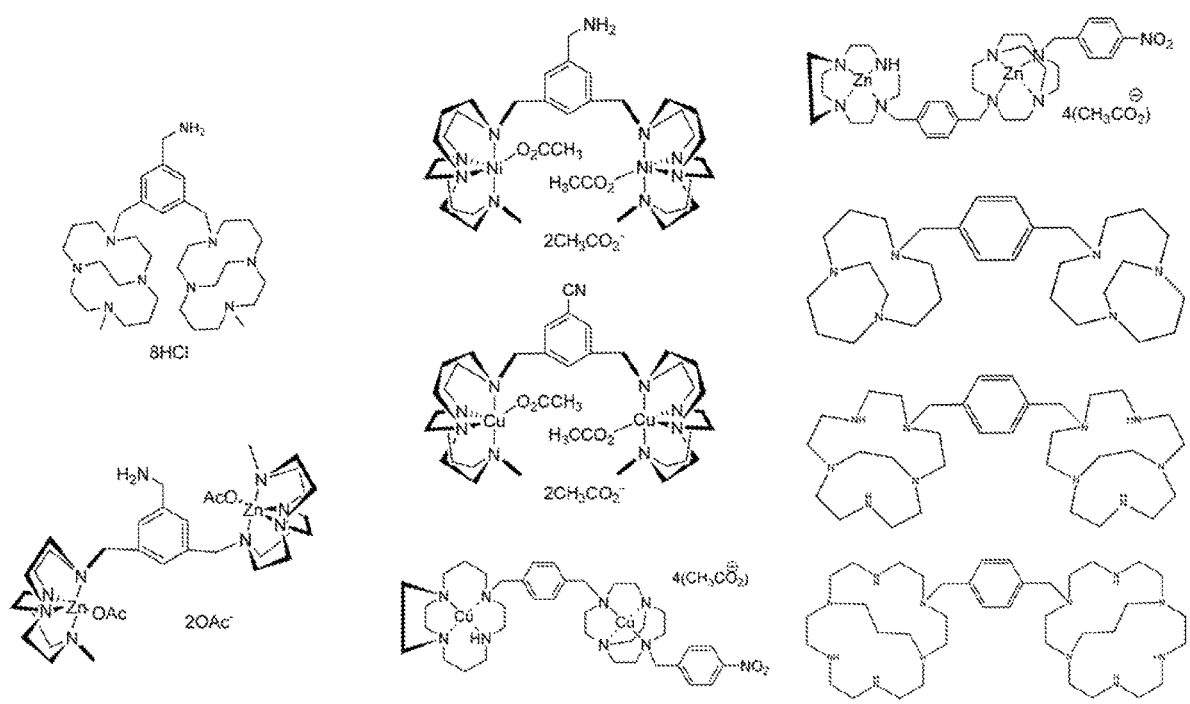

Before explaining at least one embodiment of the inventive concept(s) in detail by way of exemplary drawings, experimentation, results, and laboratory procedures, it is to be understood that the inventive concept(s) is not limited in its application to the details of construction and the arrangement of the components set forth in the following description or illustrated in the drawings, experimentation, and/or results. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All patents, published patent applications, and non-patent publications mentioned in the specification are indicative of the level of skill of those skilled in the art to which this presently disclosed and/or claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed and/or claimed herein can be made and executed without undue experimentation in light of the present disclosure. While the compositions and methods of the inventive concept(s) have been described in terms of particular embodiments, it will be apparent to those of skill in the art that variations may be applied to the compositions and/or methods and in the steps or in the sequence of steps of the method described herein without departing from the concept, spirit and scope of the presently disclosed and/or claimed inventive concept(s). All such similar substitutes and modifications apparent to those skilled in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or" Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first," "second," "third," "fourth," etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism. A molecule can be biologically active through its own functionalities, or may be biologically active based on its ability to activate or inhibit molecules having their own biological activity.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "patient" as used herein includes human and veterinary subjects. "Mammal" for purposes of treatment refers to any animal classified as a mammal, including human, domestic and farm animals, nonhuman primates, and any other animal that has mammary tissue.

"Treatment" refers to both therapeutic treatment and prophylactic or preventative measures. Those in need of treatment include, but are not limited to, individuals already having a particular condition or disorder as well as individuals who are at risk of acquiring a particular condition or disorder (e.g., those needing prophylactic/preventative measures). The term "treating" refers to administering an agent to a patient for therapeutic and/or prophylactic/preventative purposes.

A "therapeutic composition" or "pharmaceutical composition" refers to an agent that may be administered in vivo to bring about a therapeutic and/or prophylactic/preventative effect.

Administering a therapeutically effective amount or prophylactically effective amount is intended to provide a therapeutic benefit in the treatment, prevention, or management of a disease and/or condition. The specific amount that is therapeutically effective can be readily determined by the ordinary medical practitioner, and can vary depending on factors known in the art, such as the type of disease/cancer, the patient's history and age, the stage of disease/cancer, and the co-administration of other agents.

A "disorder" is any condition that would benefit from treatment with the compositions disclosed herein. This includes chronic and acute disorders or diseases including those pathological conditions which predispose the mammal to the disorder in question.

The term "effective amount" refers to an amount of a biologically active molecule or conjugate or derivative thereof sufficient to exhibit a detectable therapeutic effect without undue adverse side effects (such as toxicity, irritation and allergic response) commensurate with a reasonable benefit/risk ratio when used in the manner of the inventive concept(s). The therapeutic effect may include, for example but not by way of limitation, inhibiting the growth of microbes and/or opportunistic infections. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy," and will be understood to mean that the patient in need of treatment is treated or given another drug for the disease in conjunction with the pharmaceutical compositions of the presently disclosed and/or claimed inventive concept(s). This concurrent therapy can be sequential therapy, where the patient is treated first with one drug and then the other, or the two drugs are given simultaneously.

The terms "administration" and "administering," as used herein will be understood to include all routes of administration known in the art, including but not limited to, oral, topical, transdermal, parenteral, subcutaneous, intranasal, mucosal, intramuscular, intraperitoneal, intravitreal and intravenous routes, including both local and systemic applications. In addition, the compositions of the presently disclosed and/or claimed inventive concept(s) (and/or the methods of administration of same) may be designed to provide delayed, controlled or sustained release using formulation techniques which are well known in the art.

Turning now to the presently disclosed and/or claimed inventive concept(s), compositions are provided that comprise macrocycle derivatives incorporating bridged macrocycles. The compositions may incorporate metal ions and form stable complexes prior to administration to a subject. In particular, the presently disclosed and/or claimed inventive concept(s) include mono- or poly-azamacrocyclic molecules or their transition metal complexes that incorporate a bridged macrocycle. The compositions may possess one or more antimicrobial activity(ies), as described in further detail herein. For example, but not by way of limitation, the compositions may be effective against *Cryptococcus neoformans*.

In certain embodiments, the presently disclosed and/or claimed inventive concept(s) is directed to a composition containing at least one macrocyclic ligand, the composition comprising a compound of Formula I, II, or III:

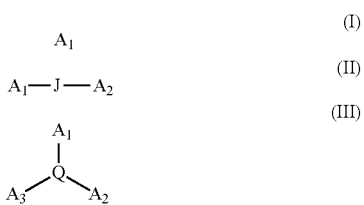

In Formulas (I)-(III), each "A" is a macrocyclic ligand independently selected from the group consisting of Formulas (IV)-(VIII), with the proviso that at least one "A" in each Formula (II) or (III) must come from Formulas (IV)-(VII):

(a) the macropolycyclic rigid ligand of Formula (IV) having denticity of 3 or 4:

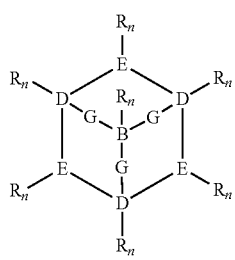

(IV)

(b) the macropolycyclic rigid ligand of Formula (V) having denticity of 4 or 5:

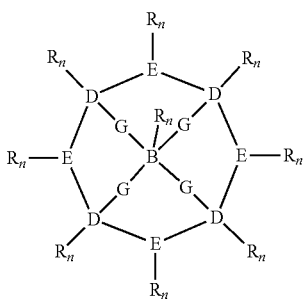

(V)

(c) the macropolycyclic rigid ligand of Formula (VI) having denticity of 5 or 6:

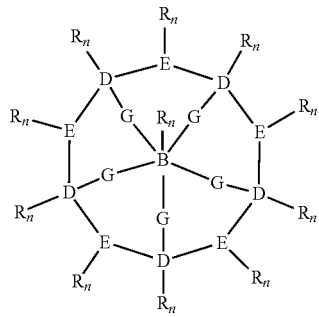

(VI)

(d) the macropolycyclic rigid ligand of Formula (VII) having denticity of 6 or 7:

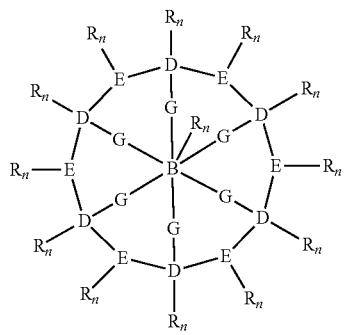

(VII)

and (e) the macrocyclic ligand of Formula (VIII) having "t"=1-4 and a denticity of 3-6:

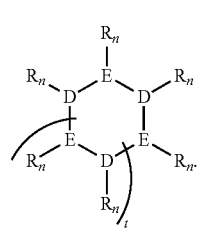

(VIII)

In Formulas (I)-(III), "J" in Formula (II) is a linking atom or a group linking two "A" macrocyclic ligands by replacing one "$R_n$" in each linked macrocycle. For example, but not by way of limitation, "J" in Formula (II) may be an o-, m-, or p-xylene linker. Also in Formulas (I)-(III), "Q" in Formula (III) is a linking atom or a group linking three "A" macrocyclic ligands by replacing one "$R_n$" in each linked macrocyle. For example, but not by way of limitation, "Q" in Formula (III) may be a 1,3,5-mesityl linker.

In Formulas (IV)-(VIII), each "E" is the moiety $(CR_n)_a$—X—$(CR_n)_{a'}$, wherein "X" is selected from the group consisting of O, S, N, P, or C. Also, for each "E," the sum of "a" plus "a'" is independently selected from 0 to 4. In certain particular embodiments, for each "E" in Formulas (IV)-(VIII), the sum of "a" plus "a'" is independently selected from 1 and 2. In addition, the sum of all "a" plus "a'" for all of the "E"s in Formula (IV) is in a range of from about 4 to about 9, the sum of all "a" plus "a'" for all of the "E"s in Formula (V) is in a range of from about 3 to about 9 (such as, but not limited to, about 5), the sum of all "a" plus "a'" for all of the "E"s in Formula (VI) is in a range of from about 5 to about 12 (such as, but not limited to, about 7), the sum of all "a" plus "a'" for all of the "E"s in Formula (VII) is in a range of from about 7 to about 15 (such as, but not limited to, about 9), and the sum of all "a" plus "a'" for all of the "E"s in Formula (VIII) is in a range of from about 4 to about 15.

Also in Formulas (IV)-(VIII), each "R" is independently selected from the group consisting of H, alkyl, heteroalkyl, alkenyl, heteroalkenyl, alkynyl, heteroalkynyl, aryl, heteroaryl, alkylaryl (e.g., benzyl), and heteroalkylaryl groups, and/or wherein two or more "R" are covalently bonded to form an aromatic, heteroaromatic, cycloalkyl, or heterocycloalkyl ring.

In addition, each "D" is a donor atom independently selected from the group consisting of N, O, S, and P, and at least two "D" atoms are bridgehead donor atoms. In particular embodiments, each "D" is a donor atom that coordinates to a metal ion.

In Formulas (IV)-(VIII), each "B" is a carbon atom, a "D" donor atom, or a cycloalkyl, aromatic, or heterocyclic ring.

Also in Formulas (IV)-(VIII), each "n" is an integer independently selected from 0, 1, and 2, completing the valence of the atoms to which the "R" moieties are covalently bonded.

Further in Formulas (IV)-(VIII), each "G" is the moiety $(CR_n)_b$, wherein (i) each "b" is an integer independently selected from about 0 to about 9, or (ii) in any of Formulas (IV)-(VIII), one or more of the $(CR_n)_b$ moieties covalently bonded from any "D" to the "B" atom or group is absent, and at least two $(CR_n)_b$ covalently bond two of the "D" donor atoms to the "B" atom in the Formula, and the sum of all "b" is within the range of from about 1 to about 5. In certain embodiments, for each "G" is the moiety $(CR_n)_b$, each "b" is an integer independently selected from about 0 to about 5, and wherein when "b" is 0, $(CR_n)_0$ represents a covalent bond.

Figure 11:
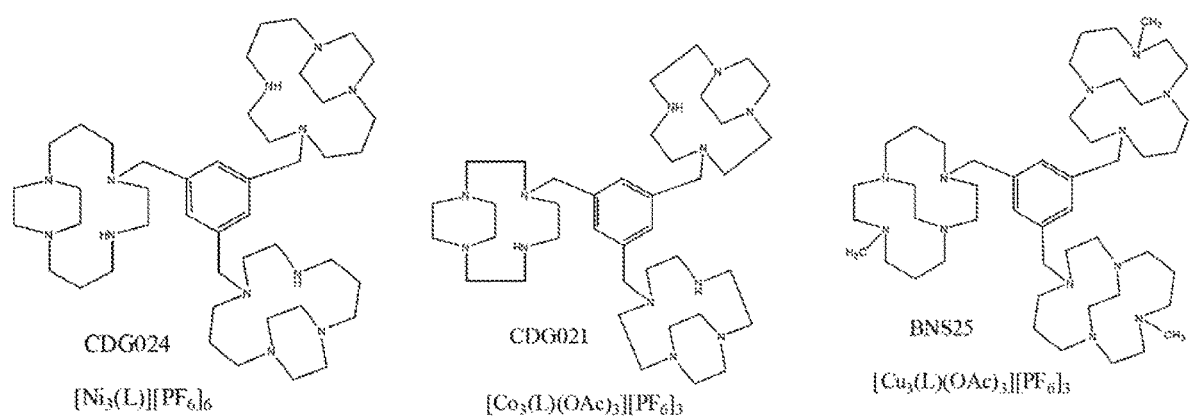
FIGS. 11, 12, and 13 graphically depict non-limiting examples of specific structures of compositions in accordance with Formula (III) of the presently disclosed and/or claimed inventive concept(s).
Figure 12:
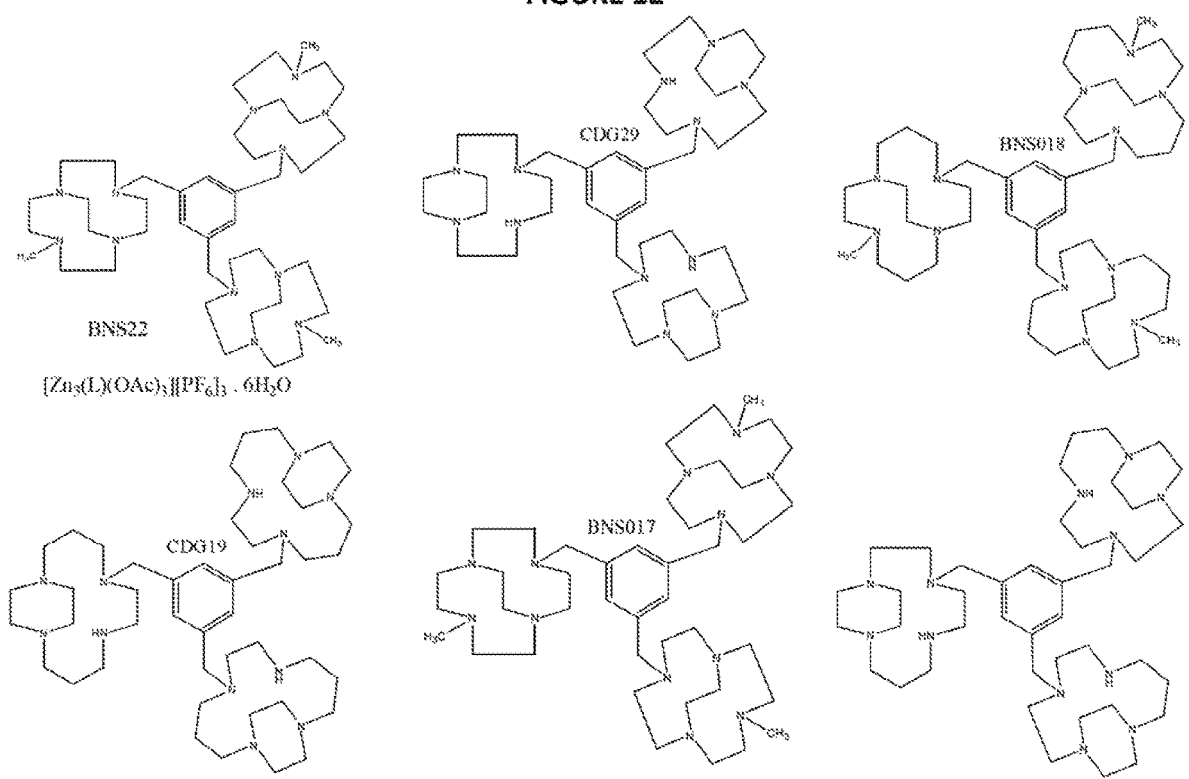
Figure 13:
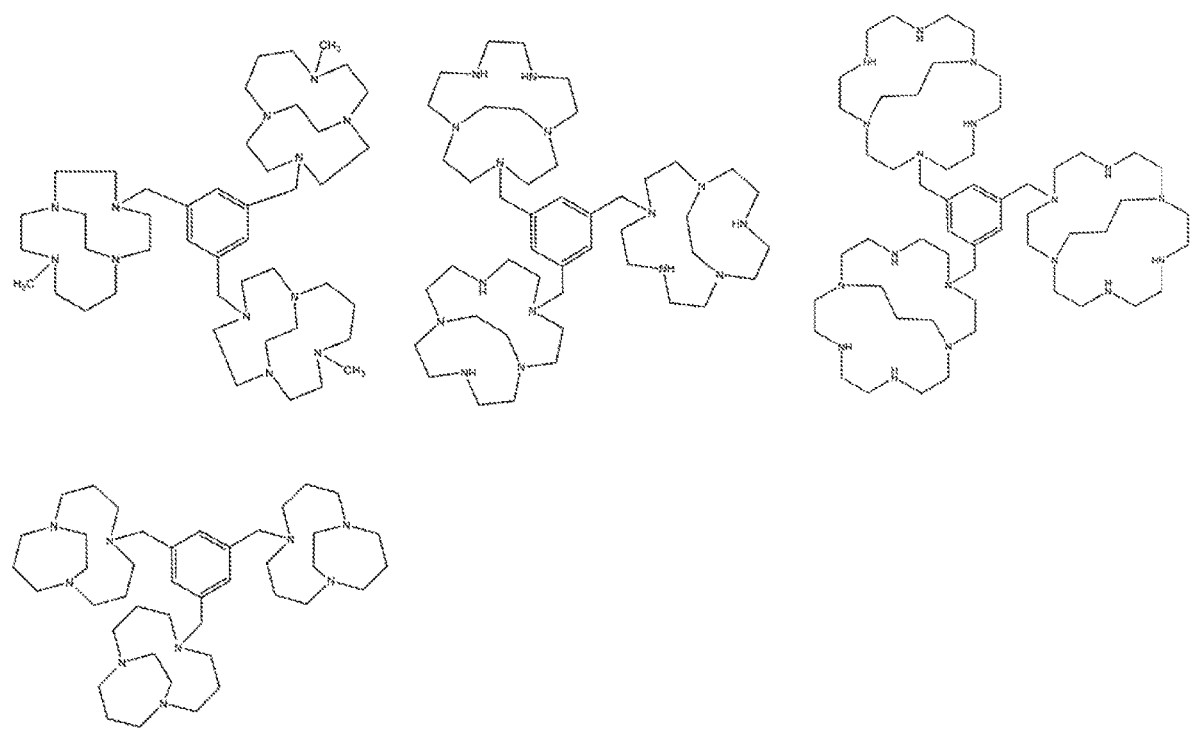
Figure 14:
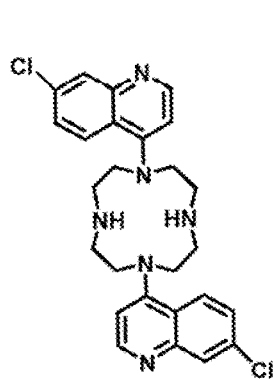
FIGS. 14-15 graphically depict non-limiting examples of specific structures of compounds in accordance with Formula (I), wherein the macrocyclic ligand "A" thereof has a structure in accordance with Formula (VIII), in accordance with the presently disclosed and/or claimed inventive concept(s).
Figure 14:
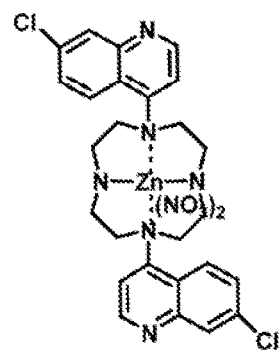
Figure 14:
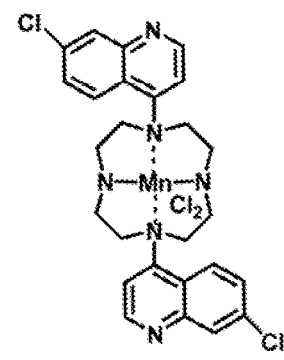
Figure 14:
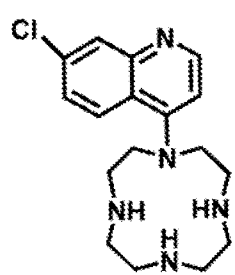
Figure 14:
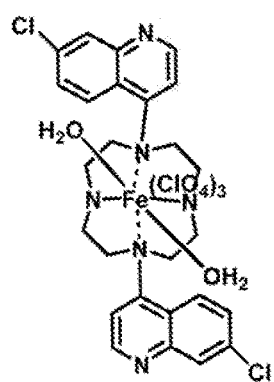
Figure 14:
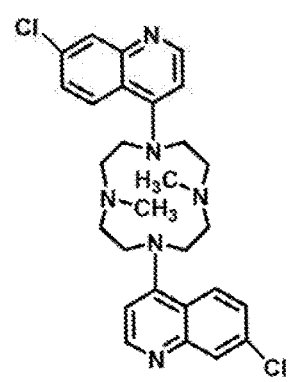
Figure 15:
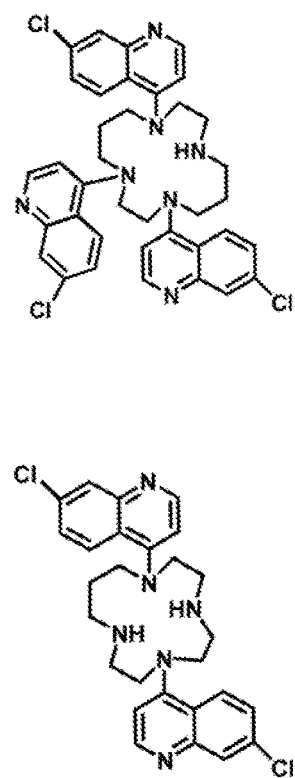
Figure 15:
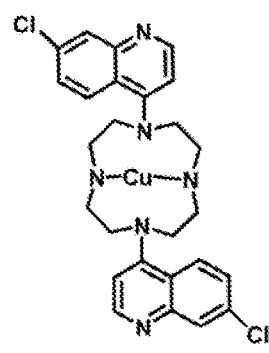
Figure 15:
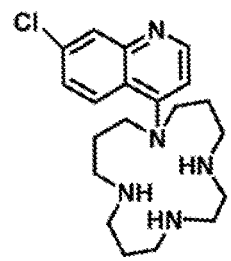
Figure 15:
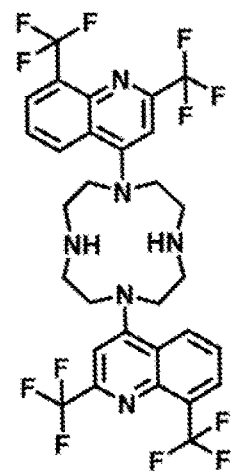

Particular, non-limiting examples of specific structures of compounds in accordance with Formula (I) are shown in FIGS. 1-6. Particular, non-limiting examples of specific structures of compounds in accordance with Formula (II) are shown in FIGS. 7-10. Particular, non-limiting examples of specific structures of compounds in accordance with Formula (III) are shown in FIGS. 11-13. Particular, non-limiting examples of specific structures of compounds in accordance with Formula I, wherein the macrocyclic ligand "A" thereof has a structure in accordance with Formula (VIII), are shown in FIGS. 14-15.

The compositions of the presently disclosed and/or claimed inventive concept(s) also include pharmaceutically acceptable salts and/or pro-drugs of the above-disclosed compounds. The compounds (as well as salts and/or pro-drugs thereof) are prepared from readily available starting materials, as described in further detail in the examples.

Any of the compositions disclosed or otherwise contemplated herein may further include a metal with which the compound is complexed. Any metal capable of complexing with the compounds may be utilized in accordance with the presently disclosed and/or claimed inventive concept(s), and the ability to select metals that may function in this manner is well within the skill of a person of ordinary skill in the art. Non-limiting examples of metals that may be utilized in accordance with the presently disclosed and/or claimed inventive concept(s) include a transition metal, a main group metal, a lanthanide, an actinide, and mixtures thereof. Particular non-limiting examples of transition metals that may be utilized in accordance with the presently disclosed and/or claimed inventive concept(s) include cobalt, copper, iron, manganese, nickel, zinc, and mixtures thereof.

In certain embodiments, the metal/compound complexes of the presently disclosed and/or claimed inventive concept(s) are charged species having formula such as, but not limited to, Formulas (XII) and (XIII) shown and described in detail herein below. The transition metal may have valence of +1, +2, +3, +4 or +5; in these cases, a pharmaceutically acceptable anion would be present in sufficient quantity to provide electronic neutrality.

Any of the compositions disclosed and/or otherwise contemplated herein may be useful in a variety of methods. For example, but not by way of limitation, said compositions may possess one or more anti-microbial activities. In particular, but not by way of limitation, any of the compositions may possess one or more activities selected from anti-fungal, anti-bacterial, and/or anti-parasitic activities. When the composition possesses an anti-fungal activity, the composition may be effective against one or more fungus including, but not limited to, *Cryptococcus* (including, but not limited to, *C. neoformans*, *C. laurentii*, and *C. albidus*); *Candida* (including, but not limited to, *C. albicans*, *C. glabrata*, and *C. krusei*); *Aspergillus* (including, but not limited to, *A. fumigatus*); and the like. When the composition possesses an anti-bacterial activity, the composition may be effective against one or more bacteria including, but not limited to, *Staphylococcus* (such as, but not limited to, *S. aureus* and Methicillin-resistant *S. aureus* (MRSA)); *Escherichia* (including, but not limited to, *E. coli*); *Pseudomonas* (including, but not limited to, *P. aeruginosa*); *Mycobacterium* (including, but not limited to, *M. intracellulare*); and the like. When the composition possesses an anti-parasitic activity, the composition may be effective against one or more parasites including, but not limited to, *Leishmania* (including, but not limited to, *L. donovani*, *L. major*, *L. tropica*, *L. braziliensis*, and *L. mexicana*); *Plasmodium* (such as, but not limited to, *P. falciparum*); *Schistosoma* (such as, but not limited to, *Schistosoma mansoni*); and the like.

Particular compounds disclosed and/or claimed herein may kill *C. neoformans* at very low concentrations and find particular but not exclusive application as antifungals which are useful in treating streptococcal meningitis among other opportunistic diseases.

Any of the compositions disclosed and/or otherwise contemplated herein may include one or more imaging agents attached thereto. Any imaging agent known in the art and capable as functioning as described in detail herein may be utilized, and thus is included within the scope of the presently disclosed and/or claimed inventive concept(s). Non-limiting examples of imaging agents include at least one of a fluorophore and/or a radioisotope. In one particular, non-limiting example, a fluorescent tag (such as, but not limited to, Rhodamine B) is attached to one or more of the macrocyclic chelators either in the presence or absence of one or more transition metal ions. In another particular, non-limiting example, one or more radioisotopes is inserted into one or more of the macrocyclic chelators either in the presence or absence of one or more transition metal ions. A non-limiting example of a pharmaceutically significant radioisotope for use in accordance with the imaging applications of the presently disclosed and/or claimed inventive concept(s) is $^{64}Cu$ (following a similar procedure to that described by Sun et al. (*Journal of Medicinal Chemistry* (2002) 45:469).

The presently disclosed and/or claimed inventive concept(s) also includes a pharmaceutical composition comprising a therapeutically effective amount of at least one of the compositions described herein in combination with a pharmaceutically acceptable carrier. As used herein, a "pharmaceutically acceptable carrier" is a pharmaceutically acceptable solvent, suspending agent, or vehicle for delivering the compositions of the presently disclosed and/or claimed inventive concept(s) to the human or animal. The carrier may be liquid or solid and is selected with the planned manner of administration in mind. Examples of pharmaceutically acceptable carriers that may be utilized in accordance with the presently disclosed and/or claimed inventive concept(s) include, but are not limited to, PEG, liposomes, ethanol, DMSO, aqueous buffers, oils, DPPC, lipids, other biologically-active molecules, vaccine-adjuvants, and combinations thereof.

The terms "liposome," "lipid nanostructure" and "vesicle" may be used interchangeably herein and will be understood to refer to an assembled structure constructed of molecules such as lipids and/or proteins, for example, not through covalent bonds but through interactions (such as but not limited to, hydrophobic interactions, electrostatic interactions and hydrogen bonds) acting between the molecules in an aqueous medium.

The terms "aqueous solution" and "aqueous medium" will be used interchangeably herein and will be understood to refer to water as well as any kind of solution which is physiologically acceptable and solvent in water.

Certain embodiments of the presently disclosed and/or claimed inventive concept(s) are directed to a method of inhibiting the growth and/or activity of at least one microbe. In the method the microbe(s) is/are contacted with any of the compositions disclosed or otherwise contemplated herein.

Other embodiments of the presently disclosed and/or claimed inventive concept(s) are directed to a method of treating, reducing the occurrence of, and/or reducing the severity of an infection in a subject. In the method, an effective amount of any of the compositions disclosed or otherwise contemplated herein is administered to the subject. In particular embodiments, the infection may be an opportunistic infection, such as but not limited to, a fungal infection, a bacterial infection, and/or a parasitic infection. In certain particular embodiments, the infection is at least one of the following: (i) a fungal infection caused by *Cryptococcus* (including, but not limited to, *C. neoformans*, *C. laurentii*, and *C. albidus*); *Candida* (including, but not limited to, *C. albicans*, *C. glabrata*, and *C. krusei*); or *Aspergillus* (including, but not limited to, *A. fumigatus*); (ii) a bacterial infection caused by *Staphylococcus* (such as, but not limited to, *S. aureus* and Methicillin-resistant *S. aureus* (MRSA)); *Escherichia* (including, but not limited to, *E. coli*); *Pseudomonas* (including, but not limited to, *P. aeruginosa*); or *Mycobacterium* (including, but not limited to, *M. intracellulare*); and/or (iii) a parasitic infection caused by at least one of *Leishmania* (including, but not limited to, *L. donovani*, *L. major*, *L. tropica*, *L. braziliensis*, and *L. mexicana*); *Plasmodium* (such as, but not limited to, *P. falciparum*); or *Schistosoma* (such as, but not limited to, *Schistosoma mansoni*). Thus, certain particular embodiments of the presently disclosed and/or claimed inventive concept(s) are directed to a method of treating, reducing the occurrence of, and/or reducing the severity of any of the above infections in a subject. In addition, certain particular embodiments of the presently disclosed and/or claimed inventive concept(s) are directed to a method of treating, reducing the occurrence of, and/or reducing the severity of a disease in a subject, wherein the disease is caused by any of the above infections. For example, but not by way of limitation, such diseases include streptococcal meningitis, leishmaniasis, and malaria.

In particular, non-limiting embodiments, a sterile aqueous solution or a physiological or buffered solution containing any of the compositions of the presently disclosed and/or claimed inventive concept(s) (including, but not limited to, metal/compound complexes) will be administered to a patient in a variety of ways, as described herein above. In addition, any of the methods disclosed herein may further include co-administration of one or more other pharmaceuticals for treatment of the infection.

In another aspect, the presently disclosed and/or claimed inventive concept(s) is directed to a method for treating a fungal disease in a mammal comprising administering to said mammal an effective amount of any of the compounds disclosed or otherwise contemplated herein, or a pharmaceutically acceptable salt or pro-drug thereof.

In addition, any of the compounds disclosed or otherwise contemplated herein are useful for application for comparative human and veterinary treatments.

In certain other embodiments, the presently disclosed and/or claimed inventive concept(s) is directed to a method of screening for the presence of an infection in a subject. In the method, the subject is contacted with an effective amount of any of the compositions disclosed or otherwise contemplated herein that has an imaging agent attached thereto. The composition is allowed to bind to an infection present in the subject, and at least a portion of the subject is exposed to an imaging device for cellular and/or tissue imaging of at least a portion of the subject to detect the presence of the imaging agent within the subject. It is determined that the patient is infected if the imaging agent is detected.

EXAMPLES

Examples are provided hereinbelow. However, the presently disclosed and/or claimed inventive concept(s) is to be understood to not be limited in its application to the specific experimentation, results and laboratory procedures. Rather, the Examples are simply provided as one of various embodiments and are meant to be exemplary, not exhaustive.

Example 1

Synthesis of meta-Xylyl bis(1,5,8,12-tetraazabicyclo[10.2.2]hexadecane (Formula IX)

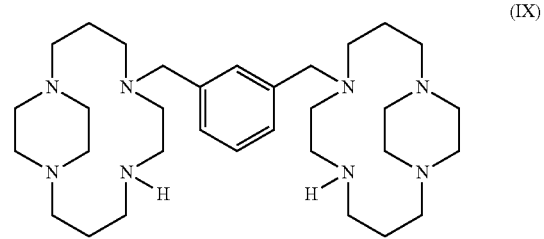 [SMILES: c1cc(CN2CCCN3CCN(CCCNCC2)CC3)cc(CN2CCCN3CCN(CCCNCC2)CC3)c1]

(IX)

cis-Perhydrotetraazapyrene, 1.2 g (5.40 mmol) and para-xylenedibromide, 0.71 g (2.70 mmol) were stirred together in dry acetonitrile (20 ml) for 24 hours. A white precipitate resulted which was collected by filtration, washed in acetonitrile, and dried in vacuo to give a white solid (1.35 g, 71%) [Procedure modified from Le Baccon et al. (*New Journal of Chemistry* (2001) 25:118)]. Mass and NMR ($^1$H and $^{13}$C) spectra were consistent with the expected product.

1.16 g (1.60 mmol) of this compound was dissolved in dry ethanol (100 ml), stirred under nitrogen, and 0.61 g (16 mmol) of NaBH$_4$ was added over a period of 20 minutes. The solution was then stirred for a further 30 minutes and refluxed under nitrogen for one hour. The solution was cooled to room temperature, 3M HCl (10 ml) was added slowly, and the solvent was removed. The resulting residue was dissolved in water (30 ml), and the pH was reduced to 14 using KOH pellets. Benzene was used to extract the basic solution (6×50 ml). The combined extracts were dried and filtered, and the solvent was removed, giving a white solid (0.59 g, 65%): $^1$H NMR (400 MHz, CDCl$_3$) δ 7.20 (s, 4H, ArH), 3.65 (s, 4H, NCH$_2$Ar), 3.27 (m, 4H, NCH$_2$), 3.02 (m, 4H, NCH$_2$), 2.93 (m, 4H, NCH$_2$), 2.70 (m, 4H, NCH$_2$), 2.63 (m, 8H, NCH$_2$), 2.56 (m, 12H, NCH$_2$), 2.26 (m, 4H, NCH$_2$), 1.81 (s, 4H, NCH$_2$), 1.72 (m, 4H, NCH$_2$). $^{13}$C NMR (CDCl₃) δ 136.40 (ArCH₂), 129.36 (ArH), 57.07 (ArCH₂N), 56.24 (CH₂N), 55.51 (CH₂N), 55.15 (CH₂N), 54.73 (CH₂N), 51.30 (CH₂N), 50.62 (CH₂N), 48.26 (CH₂N), 48.17 (CH₂N), 26.43 (NCH₂CH₂), 23.52 (NCH₂CH₂).

The HCl salt of this compound was formed by the following method. The solid, 101 mg (0.19 mmol), was dissolved in methanol (10 ml), and conc HCl:methanol (1 ml:20 ml) was added dropwise until a precipitate was observed. Filtrate was decanted off, and this process was repeated twice. Finally, the filtrate was concentrated in vacuo to give a white powder as product. Mass and NMR (¹H and ¹³C) spectra were consistent with the expected product.

Example 2: Synthesis of the Compound of Formula (X)

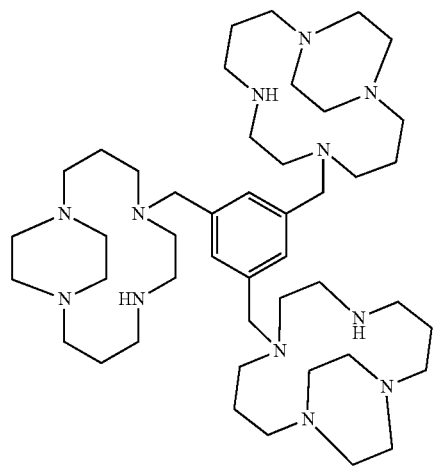

CDG19

Cyclam-glyoxal, (3.37 g, 15 mmol) synthesized according to a literature procedure, and 1,3,5-tris(bromomethyl)benzene (1.93 g, 5.42 mmol) purchased from Aldrich, were dissolved in dry acetonitrile (50 mL) and stirred under nitrogen at room temperature for 5 days. A white precipitate was collected by filtration, washed with acetonitrile (50 mL) followed by diethyl ether (10×25 mL), and dried in vacuo to yield a white powder (4.63 g, 90%).

¹H NMR: (D₂O) δ 1.40-1.43 (m, 3H), 1.75-1.78 (m, 3H), 2.16-2.20 (m, 6H), 2.29-2.34 (m, 2H), 2.42-2.48 (m, 7H), 2.63-2.69 (m, 3H), 2.96-3.10 (m, 24H), 3.19-3.33 (m, 4H), 3.43-3.52 (m, 4H), 3.52-3.60 (m, 2H), 3.66-3.69 (m, 4H), 4.19-4.25 (m, 3H), 4.36-4.37 (m, 3H), 4.90-4.95 (m, 2H), 5.19-5.30 (m, 2H), 7.81-7.83 (br s, 3H, $CH_{aromatic}$). ¹³C NMR: (D₂O) δ 18.16 (N-β-CH₂), 18.63 (N-β-CH₂), 42.10 (N-α-CH₂), 46.74 (N-α-CH₂), 51.56 (N-α-CH₂), 52.05 (N-α-CH₂), 53.48 (N-α-CH₂), 54.03 (N-α-CH₂), 54.12 (N-α-CH₂), 60.15 (N-α-CH₂), 61.18 (N-α-CH₂), 69.64 ($CH_{aminal}$), 82.53 ($CH_{aminal}$). 128.88 ($CH_{aromatic}$), 140.36 ($CH_{aromatic}$) MS: (ESI) m/z 261 [M]³⁺. HRMS: Calcd. for $C_{45}H_{75}N_{12}^{3+}$: 261.2074; Found 261.2076. Elemental Analysis Calculated as $C_{45}H_{25}N_{12}Br.7\ H_2O$: Calc: C, 47.00, H, 7.80, N, 14.62; Found: C, 47.37, H, 8.40, N, 14.80.

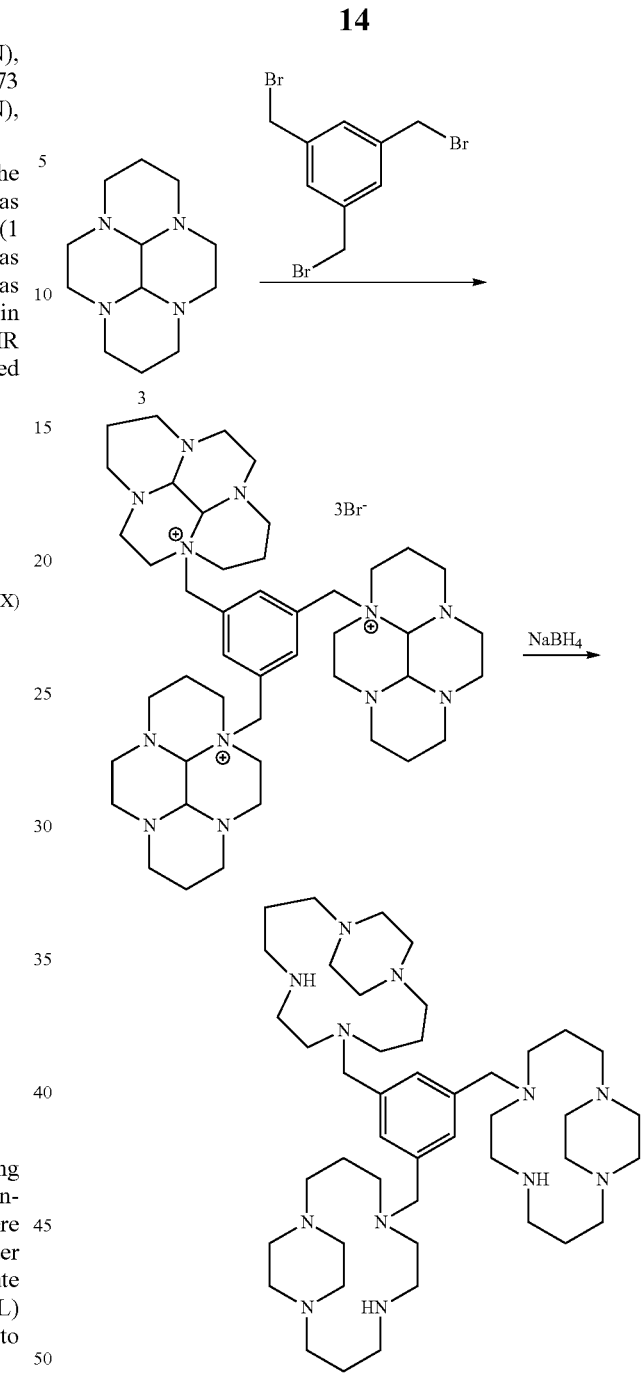

Tris-linked cyclam-glyoxal tribromide salt (5.025 g, 4.91 mmol) was dissolved in methanol (300 mL) and cooled to 0° C. Sodium borohydride (11.097 g, 293.3 mmol) was added slowly, and the clear solution was stirred under nitrogen at room temperature for 4 hours. The pH was adjusted to 1 (6M HCl). The solution was concentrated by means of rotary evaporation, and water (50 mL) was added. 30% KOH solution (100 mL) and KOH (10 g) was added to the solution, and the basic solution was then extracted with dichloromethane (3×100 mL). The combined organic fractions were dried (NaSO4), filtered, and evaporated in vacuo to yield a yellow solid (3.506 g, 90%).

¹³C NMR: (CDCl₃) δ 21.81 (N-β-CH₂), 22.03 (N-β-CH₂), 44.68 (N-α-CH₂), 46.17 (N-β-CH₂), 47.72 (N-β-CH₂), 49.30 (N-β-CH₂), 50.76 (N-β-CH₂), 54.07 (N-β-

CH$_2$), 54.27 (N-β-CH$_2$), 55.96 (N-β-CH$_2$), 56.57 (N-β-CH$_2$), 57.23 (N-β-CH$_2$), 59.12 (N-β-CH$_2$), 129.60 (CH$_{aromatic}$), 130.50 (C$_{aromatic}$). MS: (ESI) m/z 794 [MH]$^+$. HRMS: Calcd. for C$_{45}$H$_{85}$N$_{12}$$^+$: 793.6942; Found 793.6937. Elemental Analysis Calculated as C$_{45}$H$_{84}$N$_{12}$·7.8 H$_2$O: Calc: C, 57.88, H, 10.75, N, 18.00; Found: C, 58.27, H, 10.35, N, 17.60.

Example 3: Synthesis of the Compound of Formula (XI)

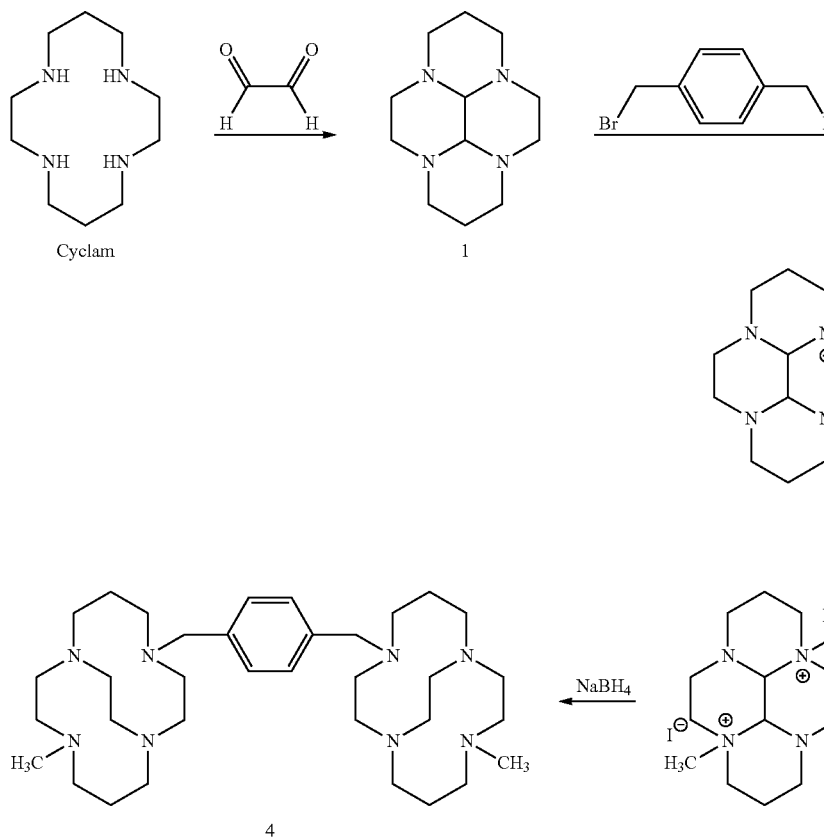
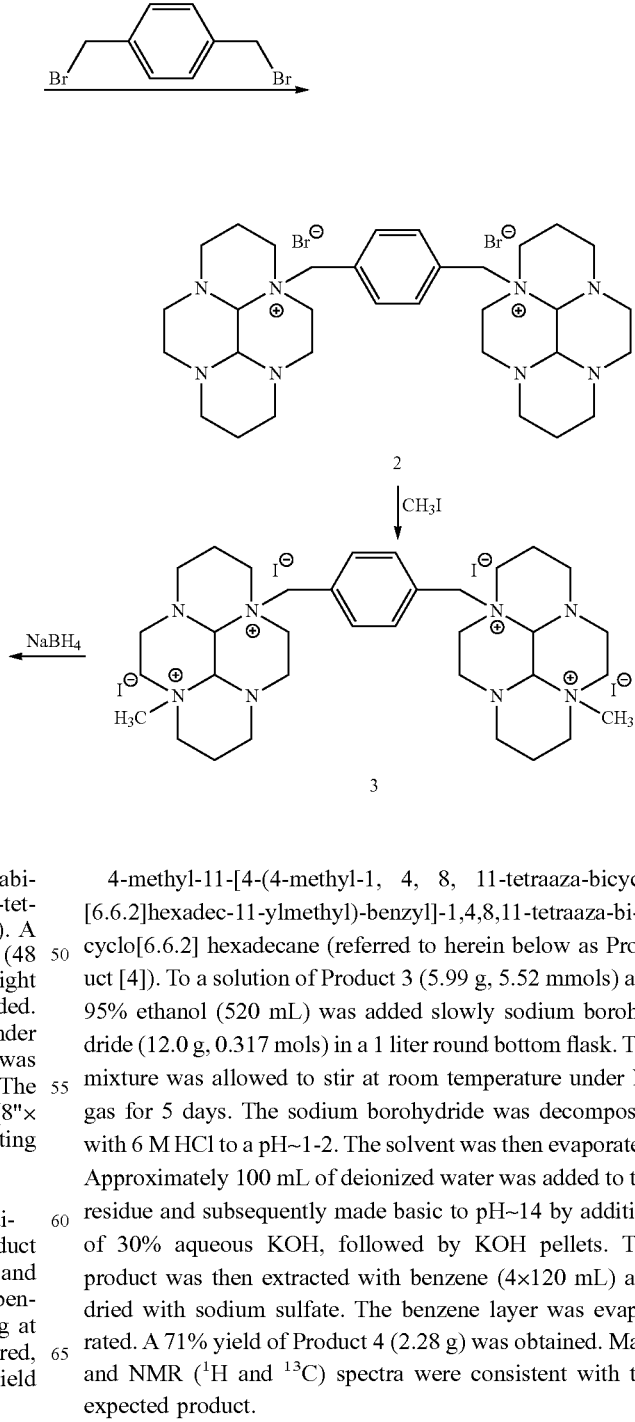

Synthesis of para-xylyl bis(1-methyl-1,5,8,12-tetraazabicyclo[6.6.2]hexadecane cis-decahydro-3a,5a,8a,10a-tetraaza-pyrene (referred to herein below as Product [1]). A solution of cyclam (11.9 g, 59.5 mmol) in acetonitrile (48 mL) was flushed with N$_2$ gas for 15 minutes before a slight molar excess of 40% glyoxal (9.34 g, 161 mmol) was added. The reaction was left to stir for 3 hours at 50-65° C. under N$_2$ gas. The solvent was evaporated, and the product was extracted from the residue with chloroform (6×40 mL). The product was then purified by alumina chromatography (8"×1") with 1% methanol in dichloromethane. The resulting yield of Product 1 was quantitative (100%).

3a-[4-(cis-decahydro-{5a,8a,10a-diaza-3a-azonia}-pyren-3a-ylmethyl)-benzyl]-cis-decahydro-{5a,8a,10a-diaza-3a-azonia}-pyrene (referred to herein below as Product [2]). To a solution of cyclam glyoxal (7.00 g, 0.03 mol) and acetonitrile (60 mL) was added 1,4-Bis-bromomethyl-benzene (4.16 g, 0.015 mol). The mixture was left stirring at room temperature for a week. The precipitate was filtered, washed with acetonitrile, and dried, giving an 86.7% yield of Product 2 (9.68 g).

3a-[4-(8a-methyl-cis-decahydro-{5a,10a-diaza-3a,8a-azonia}-pyren-3a-yl methyl)-benzyl]-8a-methyl-cis-decahydro-{5a,10a-diaza-3a,8a-azonia}-pyrene (referred to herein below as Product [3]). To a solution of Product 2 and acetonitrile (300 mL) was added iodomethane (40 mL, 0.641 mols). The mixture was left stirring at room temperature under N$_2$ gas for 2 weeks. The product was filtered and washed with acetonitrile and ether, giving a 75.5% yield of Product 3 (11.21 g).

4-methyl-11-[4-(4-methyl-1, 4, 8, 11-tetraaza-bicyclo[6.6.2]hexadec-11-ylmethyl)-benzyl]-1,4,8,11-tetraaza-bicyclo[6.6.2] hexadecane (referred to herein below as Product [4]). To a solution of Product 3 (5.99 g, 5.52 mmols) and 95% ethanol (520 mL) was added slowly sodium borohydride (12.0 g, 0.317 mols) in a 1 liter round bottom flask. The mixture was allowed to stir at room temperature under N$_2$ gas for 5 days. The sodium borohydride was decomposed with 6 M HCl to a pH~1-2. The solvent was then evaporated. Approximately 100 mL of deionized water was added to the residue and subsequently made basic to pH~14 by addition of 30% aqueous KOH, followed by KOH pellets. The product was then extracted with benzene (4×120 mL) and dried with sodium sulfate. The benzene layer was evaporated. A 71% yield of Product 4 (2.28 g) was obtained. Mass and NMR ($^1$H and $^{13}$C) spectra were consistent with the expected product.

Example 4: Synthesis of Metal Complexes (Formulae (XII) and (XIII))

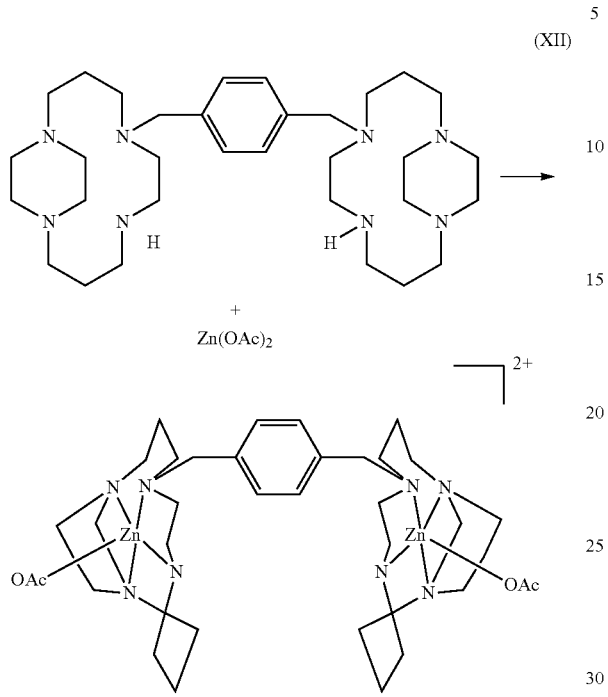

For production of the complex of Formula (XII), the ligand shown above (133.6 mg/0.23 mmol) was dissolved in methanol (20 ml), and zinc acetate (0.10 g/0.46 mmol) was added. The orange solution was refluxed for 2 hours and stirred at room temperature for 48 hours. The solution was concentrated in vacuo and redissolved in a minimum amount of methanol in an attempt to grow crystals.

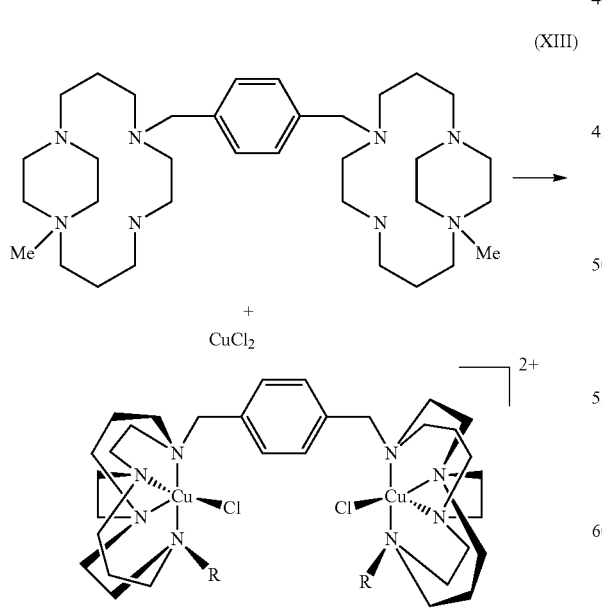

For production of the complex of Formula (XIII), the ligand shown above (112.4 mg/0.2 mmol) was dissolved in methanol (20 ml), and copper chloride (0.07 g/0.4 mmol) was added. The blue solution was refluxed for 2 hours and stirred at room temperature for 48 hours. The solution was concentrated in vacuo and redissolved in a minimum amount of methanol for recrystallisation.

Mass spectra and elemental analysis for both complexes were consistent with the expected products.

Example 5: Synthesis of Unsymmetric Compounds (Formula (XIV))

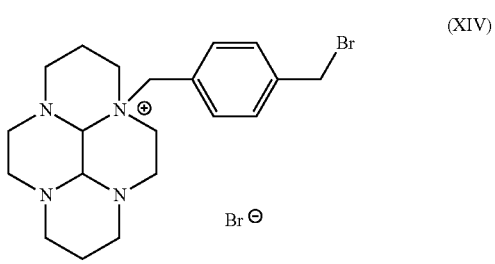 [SMILES: BrCc1ccc(C[N+]23CCCN4CCN5CCCN(CC2)C5C43)cc1 ; [Br-]]

Synthesis of 4-(bromomethyl)toludyl-glyoxal cyclam (3)

A solution of α-α'-dibromo-p-xylene (1.18 g, 4.5 mmol) in dry THF (10 mL) was added drop-wise to a solution of glyoxal cyclam (1 g, 4.5 mmol) in dry THF (15 mL), and the mixture was stirred for 10 days at room temperature. A precipitate was filtered off, washed with dry THF (4×10 mL), and dried in vacuo to yield white solid 1 (1.31 g, 60%). $^1$H NMR: (D$_2$O) δ 1.28-1.32 (m, 2H, N-β-CH$_2$), 1.68-1.72 (quin, 2H, N-β-CH$_2$), 2.03-2.12 (m, 6H, N-αCH$_2$), 2.45-2.51 (m, 6H, N-α-CH$_2$), 3.05-3.39 (m, 4H), 4.48 (s, 2H), 4.59 (s, 2H), 4.63 (d, 1H), 4.89-4.92 (d, 1H), 7.36-7.38 (d, 2H, ArH), 7.44-7.46 (d, 2H, ArH). $^{13}$C NMR: (D$_2$O) δ 18.9, 22.6 (N-α-CH$_2$), 29.8 (CH$_2$Br), 37.4, 46.8, 51.2, 56.0, 56.6, 58.6, 64.8, 66.5 (N-β-CH$_2$), 74.6, 86.4 ($C_{aminal}$), 130.3, 132.6, 134.6, 138.5 ($C_{aromatic}$). MS: (ESI) m/z 407 (M$^+$). HRMS: Calcd. for C$_{20}$H$_{30}$N$_4$Br: 405.1648; Found 405.1637.

Synthesis of 3a-(Phenylenemethylene [2a-{methylene}-perhydro-2a,4a,6a,8a-tetroozacyclooenta[f,g]acenaphthylene])-decahydro-3a,5a,8a,10a-tetraaza-pyrenium dibromide

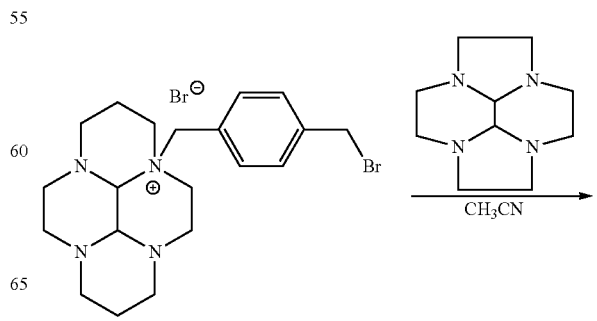

-continued

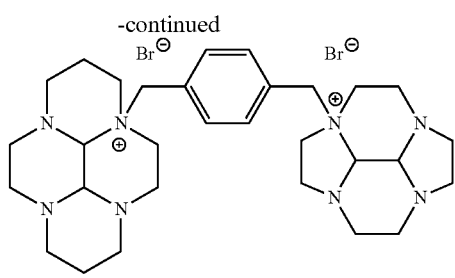

A suspension of 3a-(Phenylenemethylene bromomethyl)-decahydro-3a,5a,8a,10a-tetraaza-pyrenium bromide (0.63 g, 1.30 mmol) in acetonitrile (15 mL) was prepared, and perhydro-2a,4a,6a,8a-tetraazacyclopenta[f,g]acenaphthylene (0.3 g, 1.54 mmol) was added thereto. The resulting mixture was stirred for 5 days. The precipitate was then filtered, washed with acetonitrile, and dried in vacuo to yield 0.67 g product as a white powder (75.7% yield).

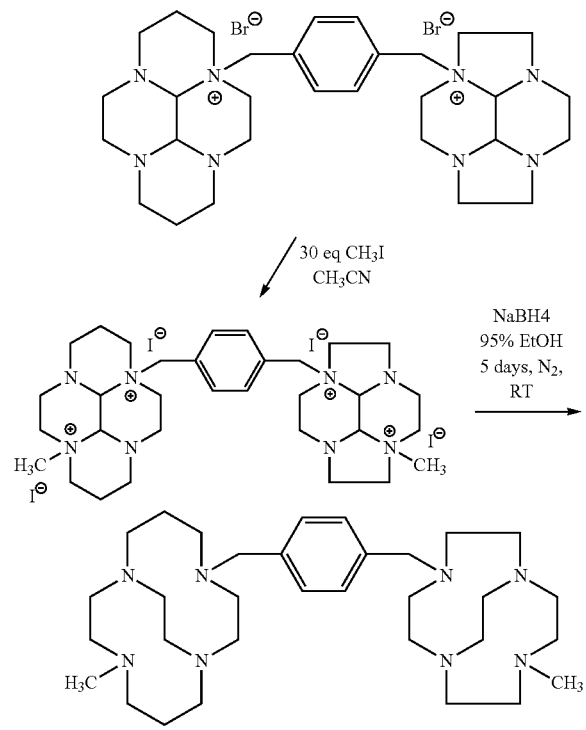

3a-(Phenylenemethylene[2a-{methylene}-perhydro-2a,4a,6a,8a-tetraazacyclo-penta[f,g]acenaphthylene])-decahydro-3a,5a,8a,10a-tetraaza-pyrenium dibromide (11.81 g, 0.0173 mol) was added to a 500 ml flask with 16.2 ml (0.260 mol) of iodomethane and 350 ml of acetonitrile. The solution was stirred at room temperature for six days, then filtered and washed with acetonitrile to yield 16.38 g of pure methylated intermediate (89% yield). This intermediate was added to a 2 L round bottom flask along with 1375 ml of 95% ethanol and 33.0 g (0.8726 mol) of NaBH$_4$. The solution was stirred at room temperature under nitrogen for five days. The sodium borohydride was decomposed with 6 M HCl, evaporated to dryness, redissolved in 200 ml of 30% aqueous KOH, and extracted with benzene. The benzene layers were combined, dried over sodium sulphate, filtered, and evaporated to give a brown oil that dried into a glassy solid product (3.59 g, 42% yield). NMR, mass spectral data, and elemental analysis were consistent with the expected product.

Example 6: Synthesis of 1,5,9,13-Tetraazabicyclo[11.2.2]heptadecane Derivatives 1,1'[1,4-phenylenebis(methylene)]-bis(1,5,9,12 Tetraazabicyclo[3.6.9.11] heptadecane)

The bis-monoquaternary macrocycle salt [synthesised by a modified procedure from Le Baccon et al. (*New Journal of Chemistry* (2001) 25:118) (1.27 mmol, 0.933 g) in dry ethanol (100 ml) was cooled in an ice bath under an inert atmosphere. Sodium borohydride (12.2 mmol, 0.479 g) was added slowly. The mixture was stirred for 30 minutes and refluxed for 1 hour. The solvent was evaporated, and water (60 ml) was added. The pH was then raised to 14 using KOH. Dichloromethane was used to extract the basic solution, and the extracts were dried over sodium sulphate for 30 minutes. The solution was then filtered, and the solvent was removed from the filtrate to give a white solid. Mass and NMR ($^1$H and $^{13}$C) spectra were consistent with the expected product. Yield=91%.

Formation of the HCl Salt.

The bis(macrocycle) (0.3448 mmol, 0.2 g) was dissolved in ethanol (20 ml), and HCl gas was bubbled through the solution for 5 minutes. A white powder precipitated out and was filtered off to yield the HCl salt. Mass and NMR ($^1$H and $^{13}$C) spectra were consistent with the expected product. Yield=85%.

Formation of a Copper Complex

Copper acetate (0.74 mmol, 0.158 g) in methanol (30 ml) was slowly added to a stirred solution of the bis(macrocycle) (0.34 mmol, 0.20 g) in methanol (20 ml) under an inert atmosphere. The copper solution changed color from turquoise to blue on addition to the macrocycle solution, indicating that the copper was complexing with the macrocycle. The mixture was stirred and refluxed for 1 hour, after which it was dried on the schlenk line to yield a blue crystalline powder. The mass spectrum was consistent with the expected product. Yield=0.29 g (90%).

Formation of the Zinc Complex

Zinc acetate (0.74 mmol, 0.159 g) in methanol (30 ml) was slowly added to a stirred solution of the bis(macrocycle) (0.34 mmol, 0.20 g) in methanol (20 ml) under an inert atmosphere. The mixture was stirred and refluxed for 1 hour, after which the product was dried on the schlenk line to yield the zinc complex. The mass spectrum was consistent with the expected product.

Example 7: Antifungal Activity of Various Macrocyclic

Derivative Compounds Against *Cryptococcus neoformans*

Summary: Various macrocyclic derivatives constructed in accordance with the presently disclosed and/or claimed inventive concept(s) were screened in vitro against *Cryptococcus neoformans* ATCC 90113 using a microdilution assay. The minimum fungicidal concentration (MFC), the lowest test concentration that kills the organism, was determined in broth media. Most of the compounds tested were found to be potent inhibitors of *C. neoformans*, with a few of the compounds being many times more potent than the standard drug Amphotericin B.

Materials and Methods:
Antimicrobial Assay:
*Cryptococcus neoformans* ATCC 90113 were obtained from the American Type Culture Collection (Manassas, Va.). The susceptibility testing was performed using a modified version of the CLSI (formerly NCCLS) methods (see below), and optical density was used to monitor growth. Samples were serially diluted in 20% DMSO/saline and transferred in duplicate to 96-well flat bottom microplates. Microbial inocula were prepared by correcting the OD630 of cell/spore suspensions in incubation broth RPMI at pH 6.0 to afford final desired target inocula. Amphotericin B ("AMB;" ICN Biomedicals, OH) was used as drug control. The organism concentration was read at 630 nm using the Biotek Powerwave XS plate reader (Bio-Tek Instruments, VT) prior to and after incubation. Minimum fungicidal concentrations were determined by removing 5 µL from each clear well, transferring to agar, and incubating until growth was seen. The MFC/MBC is defined as the lowest test concentration that kills the organism (allows no growth on agar).

References for NCCLS methods referenced above: 1 NCCLS. Reference method for broth dilution antifungal susceptibility testing of yeasts, Vol. 22. Approved standard, 2nd ed. Wayne: National Committee for Clinical Laboratory Standards; 2002: 1-51. 2 NCCLS. Reference method for broth dilution antifungal susceptibility testing of conidium forming filamentous fungi, Vol. 18. Proposed standard M38-P. Wayne: National Committee for Clinical Laboratory Standards; 1998: 1-39. 3 NCCLS. Methods for dilution antimicrobial susceptibility tests for bacteria that grow aerobically, Vol. 20. NCCLS Document M7-A5. Wayne: National Committee for Clinical Laboratory Standards; 2000: 1-58.

The term "$IC_{50}$" as used herein will be understood to refer to a test concentration in mol/L that affords 50% inhibition of the microbe relative to negative and positive controls. The abbreviation "MIC" as used herein will be understood to refer to a minimum inhibitory concentration, or the lowest test concentration in mol/L that completely inhibits the growth of the organism (100% inhibition). The abbreviation "MFC" as used herein will be understood to refer to a minimum fungicidal concentration, or the lowest test concentration in mol/L that kills the organism. All $IC_{50}$s are calculated using the XLfit® fit curve fitting software (ID Business Solutions Ltd, Guildford, Surrey, UK).

Results: As can be seen in Table 2, a surprisingly large number of the screened compounds were found to be potent inhibitors of the opportunistic fungal pathogen *C. neoformans*. The standard clinically used drug Amphotericin B (AMB) was used as a control and gave an $IC_{50}$ of 238.1 nanomols/liter. A number of the screened compounds gave $IC_{50}$ values under identical conditions that were below 100 nanmols/liter. The bolded entries in Table 2 represent test compounds that were at least as potent as the control drug AMB.

The most potent compound shown in Table 2, KS40—[Co$_2$(p-CB-cyclams)(OAc)$_2$](PF$_6$)$_2$), had an $IC_{50}$ of less than 18.04 nanomols/liter, thus making it 13 times more potent than AMB; its lower limit (MIC) was not found under the test conditions (data not shown). Low $IC_{50}$ values indicate that the composition is very potent, with lower concentrations required to produce inhibition.

Therefore, these results demonstrate that the compounds of the presently disclosed and/or claimed inventive concept(s) are effective in the treatment of *C. neoformans* infections, and that certain compounds are surprisingly much more effective than the current drug AMB.

Example 8: Antiparasitic Activity of Various Macrocyclic

Derivative Compounds Against *Leishmania donovani*

Summary: The same compounds from Example 7 were screened for activity against the leishmaniasis-causing parasite, *Leishmania donovani*. Many of these compounds were found to be potent inhibitors with activities similar to the standard clinically used drug Pentamidine.

Methods: The compounds were screened in vitro against the promastigote forms of the *leishmania* parasites employing the Alamar Blue assay as discussed below.

Antileishmanial activity of the compounds was tested in vitro against a culture of *L. donovani* promastigotes, grown in RPMI 1640 medium supplemented with 10% fetal calf serum (FCS, Gibco Chem. Co., Grand Island, N.Y.) at 26° C. A 3-day-old culture was diluted to $5\times10^5$ promastigotes/mL. Drug dilutions (50-3.1 µg/mL) were prepared directly in cell suspension in 96-well plates. Plates were incubated at 26° C. for 48 hours, and growth of *leishmania* promastigotes was determined by Alamar Blue assay. Standard fluorescence was measured on a FLUOstar® Galaxy plate reader (BMG Lab Technologies, Ortenberg, Germany) at an excitation wavelength of 544 nm and emission wavelength of 590 nm. Pentamidine and amphotericin B were used as the standard antileishmanial agents. Percent growth was calculated and plotted versus test concentration for computing the $IC_{50}$ values.

Results: As shown in Table 3, many of the compounds tested were potent inhibitors of *L. donovani*. A few of them were found to be even more potent than the standard antiparasitic drug Pentamidine (see shaded entries in Table 3). The known drug Pentamidine gave an $IC_{50}$ (inhibitory concentration inhibiting 50% of *L. donovani* growth) of 5.32 micromols/liter and was used as the control in these experiments. A number of the compounds gave $IC_{50}$ values under identical conditions below 5 micromols/liter. The most potent compound tested (BME08—[Mn(Bn$_2$PBCyclam)][MnCl4]) had an $IC_{50}$=2.65 micromols/liter, making in 2 times more potent than Pentamidine. Low $IC_{50}$ values indicate that a potential drug molecule is very potent, with lower concentrations required to produce inhibition. Therefore, these results demonstrate the discovery of novel lead structures against *L. donovani* infections.

Example 9: Antifungal Activity of Various Macrocyclic

Derivative Compounds Against *Candida glabrata* and *Candida krusei*

The single most important fungal infection worldwide and fourth most common bloodstream fungal infection in the U.S. is caused by fungi of the genus *Candida*. Although *Candida albicans* is the most common species, *C. glabrata* and *C. krusei* are also emerging causes of this infection in the last two decades, especially to those with immunocompromised and hematological malignancies. Factors like use of anti-HIV drugs, prolonged use of broad spectrum antibiotics, use of a catheter (including in kidney dialysis patients), and intensive care treatment over long periods of time may also lead to this infection due to the latter two species.

The blood infection by this fungus is known as Candidemia, which can be invasive when it spreads from the blood stream to other parts of the body, such as but not limited to, the eyes, kidney, liver, and brain. Fever, chills, skin rash, generalized weakness or fatigue, low blood pressure, muscle aches, vision changes or signs of an eye infection, headaches and neurological deficits, and abdominal pain are common syndromes of Candidemia. There is a high mortality rate in compromised, at-risk hospitalized patients from these infections. *C. glabrata* and *C. krusei* have developed resistance against the standard azole antifungal agents (such as but not limited to, fluconazole), giving a relatively higher mortality rate over *C. albicans*. A number of other types of candidiasis are also known, including but not limited to, oropharyngeal, esophageal, vulvovaginal, and urinary tract candidiasis. Vulvovaginal candidiasis, a common female genital tract infection, is caused mostly (80%-85%) by *C. albicans*; however, many of the non-*albicans* candidiasis are known to be caused by *C. glabrata* and *C. krusei*. The infections by *C. krusei* are especially troublesome, since it is considered a multidrug resistant pathogen due to its natural fluconazole resistance as well as decreased susceptibility to both flucytosine and amphotericin B. Thus, there is tremendous impetuous in discovery of drugs against these fungi.

As shown in Table 4, a number of the macrocyclic derivatives were found to be potent inhibitors of *C. krusei*. A number of these compounds had similar or higher potencies than the standard drug AMB (amphotericin B) (see shaded entries in Table 4). The most potent compound tested (BNS20—[Co$_3$(tris-CB-Cyclens(OAc)$_3$][PF$_6$]$_6$) was about 3 times more potent than AMB in inhibiting *C. krusei* in vitro.

As shown in Table 5, a large number of macrocyclic derivative compounds were found to be active against *C. glabrata*. The shaded entries in Table 5 represent test compounds that were at least as potent as the control drug AMB. As can be seen, many of these compounds were about 2-3 times more potent than AMB. The most potent compound (CDG021—[Co$_3$(tris-SB-Cyclens(OAc)$_3$][PF$_6$]$_3$) was 2.66 times more potent than AMB. Thus, these compounds clearly serve as attractive new agents for the treatment of candidiasis caused by *C. krusei* and/or *C. glabrata*.

Example 10: Antiparasitic Activity of Various Macrocyclic

Derivative Compounds Against *Plasmodium falciparum*

Malaria is a major global health problem with almost half of the global population at risk of being infected with one of the five *Plasmodium* species namely: *P. falciparum* (80% of cases), *P. vivax, P. ovale, P. malariae,* and *P. knowlesi*. In 2012, according to the World Health Organization (WHO), more than 207 million developed symptomatic malaria causing about 473,000 to 789,000 deaths. 80% of these deaths were in sub-Saharan Africa. Current US military personnel deployed in the endemic areas as well as veterans of wars are also susceptible to malaria. A military peacekeeping operation in Liberia in 2003 failed due to 80 cases of malaria in 220 Marines within the first few weeks of the mission. In 2011, 1,925 cases of malaria were reported in the US, which is the highest since 1971. 1,920 cases of these were contracted in countries outside of the US. About 64% of these malaria cases were due to *P. falciparum*, and 28% were due to *P. vivax* infection. The deadliest of the *Plasmodium* species that causes human malaria is *P. falciparum*. The 4-aminoquinoline based drugs, such as chloroquine (CQ), have historically proven to be highly effective to treat malaria, but are now rendered less effective due to resistance problems. Artemisinin-based combination chemotherapies (ACTs) form the mainstay of current WHO-recommended malaria treatment approaches. However, delayed hemolysis has been reported in several cases after treatments with ACTs, and the risk of neurotoxic effects of artemisinins in populations have not been fully addressed. Moreover, artemisinins are not fully effective in blocking transmission of malaria and also prevention of malaria relapse, the major challenges for malarial control and elimination efforts. The spread of artemisinin resistance has already caught global attention. There are no effective vaccines for human malaria, and the efficacy of the available drugs, which are not free of toxicity, is declining as resistance emerges. Thus, there is a strong impetus to identify potential new drug treatments for malaria.

As seen in Table 6, a large number of the macrocyclic derivative compounds were found to inhibit the malarial parasite (*P. falciparum*) at nanomolar concentrations. A number of these compounds have comparable potencies to the standard drug chloroquine against both chloroquine-sensitive (D6 strain) and chloroquine-resistant (W2 strain) *P. falciparum*. A large number of these compounds were several times more potent than chloroquine against the chloroquine-resistant *P. falciparum* (see shaded entries); two of these compounds (K-PAA2-0016-P32—Tris-Cyclam; and K-PAA-0016-P36—Fe-complex-4,10-bis(chloroquinoline) cyclen) were about 13 and 18 times more potent, respectively, than chloroquine. One of these compounds was also found to be a potent antimalarial agent in vivo when tested in a mouse model.

Experimental Procedure for Malaria Screen

The compounds were assayed for in vitro antimalarial activity against the W2 clone and D6 clone of the pathogenic *Plasmodium falciparum*. The strains of *P. falciparum* were obtained from the Division of Experimental Therapeutics, Walter Reed Army Institute of Research, Washington D.C. Strains of Sierra Leon D6 and Indochina W2 are chloroquine-sensitive and chloroquine-resistant, respectively. The parasite was grown in type A human RBCs and, two strains subcultured daily with fresh medium and blood cells. On the day of the assay, a suspension of infected blood cells (2% parasitemia and 2% hematocrit) was prepared using type A human red blood cells. Assays were performed by standard 96-well flat-bottomed microplate methods and done in duplicate at different concentrations. IC$_{50}$ values were obtained from the dose curves. Artemisinin and chloroquine were included in each assay as the drug controls, and DMSO was used as vehicle control. The whole protocol was developed based on the published method of Makler. The cytotoxicity assays were also performed in parallel against the Vero cells, and the selectivity index was measured. A selectivity index of >9 was considered to indicate a lead for further development of antimalarial drug.

Example 11: Antibacterial Activity of Various Macrocyclic Derivative Compounds

Against *Staphyloccus Aureus* and Methicillin-Resistant *S. aureus* (MRSA)

Most Staphylococci infections, which can be contagious, are caused by *S. aureus*. It is normally found in the nose and on the skin, which on damage to the skin or other injury, overcome the natural protective mechanisms of the body, leading to infection. Apart from a variety of skin infections, it can also infect blood (bacteremia or sepsis that may lead to death) and other organs including lungs (pneumonia), the heart valves (endocarditis—leading to heart failure), and bones (osteomyelitis). The mortality rate of untreated sepsis is over 80%.

The methicillin-resistant *S. aureus* (MRSA), aka superbug, is resistant to the antibiotic methicillin and related drugs, including penicillin, amoxicillin, and oxacillin. MRSA can be both health care-associated (HA-MRSA) and community-associated (CA-MRSA). According to the U.S. Centers for Disease Control and Prevention (CDC) estimation, about 12% of MRSA infections are CA-MRSA arising from poor hygiene. Although skin infections with MRSA can be treated successfully with proper skin care and antibiotics, it can lead to life-threatening blood or bone infections due to its inherent resistance to the common antibiotics.

As can be seen in Tables 7 and 8, a number of the various macrocyclic derivative compounds were found to be inhibitors of *S. aureus* (Table 7) and MRSA (Table 8). The standard clinical drug ciprofloxacin (CIPRO) was used as a control and gave $IC_{50}$ values against *S. aureus* and MRSA of 0.272 micromols/liter and 0.211 micromoles/liter, respectively. A number of the screened compounds gave $IC_{50}$ values under identical conditions below 10 micromols/liter. However, none of the compounds in Tables 7 and 8 showed potency that was greater than the standard drug CIPRO. The most potent compounds were about 20% as potent as CIPRO against both *S. aureus* and MRSA. Although these compounds are not more potent than the standard drug, due to growing antibiotic resistance, and in particular the difficulties in controlling MRSA, classes of compounds with significant activity, such as those in Tables 7 and 8, should be viewed as potential leads for further development of new antibiotic compounds.

Example 12: General Experimental Procedures for Examples 7-11

Unless otherwise described herein above, the general experimental procedures for Examples 7-11 were as follows.

General Experimental Procedures. All organisms were obtained from the American Type Culture Collection (Manassas, Va.) and include the fungi *Candida albicans* ATCC 90028, *C. glabrata* ATCC 90030, *C. krusei* ATCC 6258, and *Cryptococcus neoformans* ATCC 90113, and the bacteria *Staphylococcus aureus* ATCC 29213 and methicillin-resistant *S. aureus* ATCC 33591 (MRS). All organisms were tested using modified versions of the CLSI (formerly NCCLS) methods. For all organisms, optical density was used to monitor growth (NCCLS, Reference Method for Broth Dilution Antifungal Susceptibility Testing of Yeasts; Approved Standard M27-A2. National Committee on Clinical Laboratory Standards, 2002 22 (15); and NCCLS, Methods for Dilution Antimicrobial Susceptibility Tests for Bacteria that Grow Aerobically; Approved Standard, Seventh Edition M7-A7. National Committee on Clinical Laboratory Standards, 2006. 26(2)).

Samples (dissolved in DMSO) were serially-diluted in 20% DMSO/saline and transferred (10 μL) in duplicate to 96 well flat bottom microplates. Inocula were prepared by correcting the $OD_{630}$ of microbe suspensions in incubation broth [RPMI 1640/0.2% dextrose/0.03% glutamine/MOPS @ pH 6.0 (Cellgro) for *Candida* spp., Sabouraud Dextrose for *C. neoformans*, and cation-adjusted Mueller-Hinton (Difco) @ pH 7.3 for *Staphylococcus* spp. to afford an assay volume of 2004 and final target inocula of: *Candida* spp. and *C. neoformans*: $1.5 \times 10^3$, and *Staphylococcus* spp.: $5.0 \times 10^5$ CFU/ml. Final sample test concentrations were 1/100th the DMSO stock concentration. Drug controls [Ciprofloxacin (ICN Biomedicals, Ohio) for bacteria and Amphotericin B (ICN Biomedicals, Ohio) for fungi] were included in each assay. All organisms were read at either 530 nm using the Biotek Powerwave XS plate reader (Bio-Tek Instruments, Vermont) prior to and after incubation: *Candida* spp. at 35° C. for 46-50 h, *Staphylococcus* spp. at 35° C. for 16-20 h, and *C. neoformans* at 35° C. for 70-74 h. $IC_{50}$s (concentrations that afford 50% inhibition relative to controls) were calculated using XLfit 4.2 software (IDBS, Alameda, Calif.) using fit model 201. The MIC is defined as the lowest test concentration that allows no detectable growth. Minimum fungicidal or bactericidal concentrations were determined by removing 5 μl from each clear (or blue) well, transferring to fresh media, and incubating as previously mentioned. The MFC/MBC is defined as the lowest test concentration that kills the organism (allows no growth).

Primary Analysis. Samples were tested in duplicate at one test concentration (50 μg/mL), and percent inhibitions were calculated relative to blank and growth controls. Samples showing ≥50% inhibition in at least one test organism were selected for dose response (Secondary) studies.

Secondary Analysis. Extracts from the Primary Assay, and first-run pure compounds and column fractions were tested in duplicate at 3 test concentrations (5-fold dilutions). Samples dissolved to 20 mg/mL in DMSO were tested at 200, 40, and 8 μg/mL. Samples dissolved to 2 mg/mL in DMSO were tested at 20, 4, and 0.8 μg/mL.

Tertiary Analysis. Pure compounds showing an $IC_{50}$ 7 μg/mL were re-tested in duplicate using 2-fold (vs. 5-fold) dilutions: 20, 10, 5 . . . μg/mL.

Example 13: Antiparasitic Activity of Various Macrocyclic Derivative Compounds Against *Schistosoma mansoni*

The compounds utilized in this Example are listed in Table 9. All compounds were initially dissolved in 100% DMSO to a concentration of 10 mM. The compounds were stored at −20° C.

Methods

In Vitro Testing on *Schistosoma mansoni* Newly Transformed Schistosomula (NTS)

Assays were prepared according to the laboratory SOP for the lab of Dr. Jennifer Keiser (Swiss Tropical and Public Health Institute, Basel). Harvested *S. mansoni* cercariae (Liberian strain) obtained from infected *Biomphalaria glabrata* snails were mechanically transformed into newly transformed schistosomula (NTS) following standard procedures. Briefly, snails were placed under light in the morning to stimulate cercarial shedding. The cercarial suspension was collected, cooled for 30 minutes, and then vigorously pipetted (30×) and vortexed (3 minutes). The suspension was then placed in the incubator (37° C. and 5% $CO_2$) for 30 minutes, and the vortexing and pipetting steps were repeated. The transformation was complete at this point, and the tails were separated from the heads by rinsing three times with cold HBSS. NTS were then incubated overnight in culture medium overnight and used the next day.

The original stock compounds (which were not already dissolved) were dissolved in dimethyl sulfoxide (DMSO) to a concentration of 10 mM. 100 NTS were placed in each well of a 96-well plate with culture medium, and the test compound for a final well volume of 250 μl. Culture medium was composed of Medium 199 (Invitrogen, Carlsbad, Calif.)

supplemented with 5% fetal calf serum (iFCS, 100 U/ml) and 1% penicillin/streptomycin mixture (Invitrogen, 100 U/ml). Each compound was first tested at a single high concentration (33.3 µM) once in triplicate. NTS incubated with no more than 1% DMSO served as control. NTS were kept in an incubator at 37° C. and 5% $CO_2$ for up to 72 hours. After 72 hours, the condition of the NTS was microscopically evaluated using a scale from 3 (normal activity and no tegument alteration) to 0 (dead, completely granulated). In a next step, active compounds were studied at 10 µM. $IC_{50}$ determination assays were performed for active compounds and set up in the same manner. Active compounds progressed into $IC_{50}$ determination. For the $IC_{50}$ determination assays, drug concentrations ranging from 8.3-0.52 µM were used.

In Vitro Tests on *Schistosoma mansoni* Adult Worms

All assays were prepared in compliance with the laboratory SOP described herein above. Female NMRI mice (age 3 weeks, weight ca. 14 g) were purchased from Charles River (Sulzfeld) or Harlan Laboratories (Blackthorn, United Kingdom). The animals were allowed to adapt for 1 week under controlled conditions (22° C., 50% humidity, 12 hours light, and free access to water and rodent diet) before experimental handling. To obtain adult schistosomes, NMRI mice were infected subcutaneously with 80 to 100 cercariae. After 7 to 8 weeks, the mice were euthanized with $CO_2$, and the worms were collected from the hepatic portal and mesenteric veins.

Two pairs of adult worms were placed in each well of a 24-well plate with 2 ml culture medium and the test compound. Culture medium was composed of RPMI 1640 (Invitrogen, Carlsbad, Calif.) supplemented with 5% fetal calf serum (iFCS, 100 U/ml) and 1% penicillin/streptomycin mixture (Invitrogen, 100 U/ml). Compounds active against NTS were tested against adult worms at 10 µM. Schistosome incubation with no more than 1% DMSO served as control. Worms were kept in an incubator at 37° C. and 5% $CO_2$ for up to 72 hours. After 72 hours, worm condition was microscopically evaluated using a scale from 3 (normal activity and no tegument alteration) to 0 (dead, completely granulated). Active compounds progressed into $IC_{50}$ determination. For the $IC_{50}$ determination assays drug concentrations ranging from 10-0.41 µM were used.

Statistics

For the in vitro drug sensitivity assays, all viability scores were averaged across replicates and normalized to the average viability scores of the control wells (Microsoft Office Excel 2010). To calculate $IC_{50}$ values, viability scores were converted into effect stores which were entered, along with the drug concentrations, into the $IC_{50}$-calculating software, CompuSyn2® (ComboSyn Inc., MIT, Cambridge, Mass.; 2007).

Results

Results of In Vitro *S. mansoni* NTS Screen

Thirteen compounds of the 98 compounds tested were highly active on NTS (33.3 µM) (Table 9). These compounds were next tested at 10 µM (Table 10). Five compounds resulted in death of all NTS. The five compounds were then assayed for $IC_{50}$ determination. Table 11 below lists the $IC_{50}$ of these compounds. $IC_{50}$s range from 0.83-9.65 µM. For comparison, praziquantel has an $IC_{50}$ of 2.2 µM against NTS.

Results of In Vitro *S. mansoni* Adult Worm Screen

Of the five compounds assayed on adult worms at a concentration of 10 µM (Table 12), two were highly active by 72 hours post-exposure, killing all the worms. One was moderately active by 72 hours post-exposure (activity over 80%), and two compounds were not active by 72 hours post-exposure (activity under 10%) at 10 µM. The three active compounds further underwent $IC_{50}$ characterization, and the values are shown in Table 13. $IC_{50s}$ range from 1.6-4.2 µM. For comparison, praziquantel has an $IC_{50}$ of 0.1 µM.

Since from this set of compounds tests were done against both adults and NTS, Table 14 shows how the activities of the compounds overlap against these stages.

Thus, in accordance with the presently disclosed and/or claimed inventive concept(s), there have been provided compositions and methods of producing and using same that fully satisfy the objectives and advantages set forth hereinabove. Although the presently disclosed and/or claimed inventive concept(s) has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the presently disclosed and/or claimed inventive concept(s).

TABLE 2

The in vitro Inhibitory Activity of the Macrocyclic Compounds Against *C. neoformans*

| Sample Code | Sample Code | Molecular Weight | *C. neoformans* $IC_{50}$ (µg/mL) | X more potent than Amphotericin B | *C. neoformans* $IC_{50}$ (mol/L) |
|---|---|---|---|---|---|
| Amphotericin B | AMB | 924.079 | 0.220 | 1.00 | 2.381E−07 |
| p-CB-cyclens HCl salt | OB15B | 872.115 | 0.610 | 0.34 | 6.994E−07 |
| m-CB-homocyclens HCl salt | OB65B | 990.676 | 0.160 | 1.47 | 1.615E−07 |
| m-CB-cyclens HCl salt | DJC05C | 890.561 | 0.940 | 0.23 | 1.056E−06 |
| p-CB-homocyclens HCl salt | TA22C | 928.223 | 0.310 | 0.71 | 3.340E−07 |
| p-CB-cyclams | KS23 | 582.926 | 8.200 | 0.02 | 1.407E−05 |
| m-CB-cyclams HCl salt | TJS04 | 973.692 | 0.380 | 0.61 | 3.903E−07 |
| m-SB-cyclams HCl salt | KS22B | 918.615 | 0.070 | 3.13 | 7.620E−08 |
| p-SB-cyclens HCl salt | OB24B | 863.104 | 0.670 | 0.31 | 7.763E−07 |
| m-SB-cyclens HCl salt | OB25B | 926.161 | 0.300 | 0.74 | 3.239E−07 |
| p-SB-homocyclens HCl salt | OB45B | 818.500 | 0.290 | 0.67 | 3.543E−07 |
| m-SB-homocyclens HCl salt | OB46B | 881.5 | 0.280 | 0.75 | 3.176E−07 |
| tris-SB-cyclams | CDG19 | 793.242 | 0.180 | 1.05 | 2.269E−07 |
| tris-SB-cyclens | CDG29 | 709.081 | 0.100 | 1.69 | 1.410E−07 |
| tris-CB-cyclens | BNS017 | 751.162 | 0.070 | 2.56 | 9.319E−08 |
| tris-CB-cyclams | BNS018 | 835.323 | 0.090 | 2.21 | 1.077E−07 |
| (dcp)1-SB-cyclen | OB99 | 358.314 | 0.310 | 0.28 | 8.652E−07 |

TABLE 2-continued

The in vitro Inhibitory Activity of the Macrocyclic Compounds Against *C. neoformans*

| Sample Code | Sample Code | Molecular Weight | *C. neoformans* IC$_{50}$ (μg/mL) | X more potent than Amphotericin B | *C. neoformans* IC$_{50}$ (mol/L) |
|---|---|---|---|---|---|
| [Cu(dcp1-SB-cyclen)(OAc)]PF6 | OB105 | 707.370 | 2.190 | 0.08 | 3.096E−06 |
| [Ni(dcp1-SB-cyclen)(OAc)]PF6 | OB106 | 621.013 | 0.390 | 0.38 | 6.280E−07 |
| [Zn(dcp1-SB-cyclen)(OAc)]PF6 | OB110A | 758.105 | 0.610 | 0.30 | 8.046E−07 |
| [Co(Me1dcp1-CB-cyclen)(OAc)]PF6 | OB118 | 635.283 | 6.050 | 0.03 | 9.523E−06 |
| [Cu2(p-CB-cyclams)(OAc)2](PF6)2 | TJH384A | 1118.030 | 0.700 | 0.38 | 6.261E−07 |
| [Zn2(p-CB-cyclams)(OAc)2](PF6)2 | KS34 | 1121.697 | 0.650 | 0.41 | 5.795E−07 |
| [Ni2(p-CB-cyclams)(OAc)2](PF6)2 | KS33 | 1108.317 | 1.020 | 0.26 | 9.203E−07 |
| [Co2(p-CB-cyclams)(OAc)2](PF6)2 | KS40 | 1108.804 | 0.020 | 13.21 | 1.804E−08 |
| Me1Pic1-CB-cyclen | KRW32 | 303.454 | 5.490 | 0.01 | 1.809E−05 |
| [Co(Me1Pic1-CB-cyclen)](PF6)3 | KRW48 | 838.329 | 1.090 | 0.18 | 1.300E−06 |
| [Zn(Me1Pic1-CB-cyclen)](PF6)2 | KRW49 | 694.79 | 5.230 | 0.03 | 7.527E−06 |
| p-CB-H2Bcyclams | JGL44 | 554.872 | 0.180 | 0.73 | 3.244E−07 |
| p-CB-H2Bcyclens | JGL19 | 498.764 | 0.590 | 0.20 | 1.183E−06 |
| p-dcp2-CB-cyclens | PW111A | 818.764 | 0.040 | 4.88 | 4.885E−08 |
| Fe-complex-4,10-bis(7-chloroquinoline)cyclen)Cl2 | K-PAA-0016-P36 | 885.67 | 0.940 | 0.22 | 1.061E−06 |
| [Mn2(H2-p-CB-cyclams)][MnCl4]2 | TJH412 | 1058.231 | 1.990 | 0.13 | 1.880E−06 |
| [Fe2(H2-p-CB-cyclams)][FeCl4]2 | TJH413B | 1061.859 | 7.380 | 0.03 | 6.950E−06 |
| [Co2(H2-p-CB-cyclams)(OAc)3][PF6]3 | TJH414B | 1284.749 | 0.234 | 1.31 | 1.821E−07 |
| [Ni2(H2-p-CB-cyclams)(OAc)2][PF6]2 | TJH415B | 1080.261 | 0.850 | 0.30 | 7.868E−07 |
| [Cu2(H2-p-CB-cyclams)(OAc)2][PF6]2•5H2O | T1H416B | 1180.042 | 3.030 | 0.09 | 2.568E−06 |
| [Zn2(H2-p-CB-cyclams)(OAc)2][PF6]2•H2O | TJH417B | 1111.681 | 3.120 | 0.08 | 2.807E−06 |
| [Co(Me1Py1-CB-Cyclam)Cl]PF6 | DGJ012 | 570.849 | 4.730 | 0.03 | 8.286E−06 |
| [Co(B13N4)Cl2]PF6 | DGJ031 | 515.192 | 4.980 | 0.02 | 9.666E−06 |
| m-CB-cyclam-cyclen | DGJ036 | 554.856 | 5.800 | 0.02 | 1.045E−05 |
| Bn2PBCyclam | SLK09 | 420.645 | 0.910 | 0.11 | 2.163E−06 |
| [Mn(Bn2PBCyclam)][MnCl4] | BME08 | 672.321 | 1.203 | 0.13 | 1.789E−06 |
| [Fe(Bn2PBCyclam)][FeCl4]•H2O | BME09 | 692.15 | 1.070 | 0.15 | 1.546E−06 |
| [Cu(Bn2PBCyclam)(OAc)]PF6•2.5 H2O | BME10B | 733.227 | 13.810 | 0.01 | 1.883E−05 |
| Cu(Bn2PBCyclam)(OAc)2 | DJD20 | 602.281 | 3.130 | 0.05 | 5.197E−06 |
| [Co(Bn2PBCyclam)(OAc)]PF6 | DJD21 | 683.587 | 3.510 | 0.05 | 5.135E−06 |
| [Ni(Bn2PBCyclam)(OAc)]PF6 | DJD22 | 683.344 | 5.240 | 0.03 | 7.668E−06 |
| [Zn(Bn2PBCyclam)(OAc)]PF6 | DJD23 | 690.044 | 1.990 | 0.08 | 2.884E−06 |
| [p-(BMBCyclams)]Br2 | SLK17A | 712.568 | 8.250 | 0.02 | 1.158E−05 |
| [m-(BMBCyclams)]Br2 | DJD05 | 712.568 | 3.250 | 0.05 | 4.561E−06 |
| [Mn2(m-cyclam-homocyclen)][MnCl4]2•12H2O | AW047 | 1288.441 | 3.770 | 0.08 | 2.926E−06 |
| [Fe2(m-cyclam-homocyclen)][FeCl4]2•7H2O | AW048 | 1201.993 | 1.660 | 0.17 | 1.381E−06 |
| [Co2(m-cyclam-homocyclen)(OAc)2][PF6]2 | AW049 | 1094.768 | 0.156 | 1.67 | 1.425E−07 |
| [Ni2(m-cyclam-homocyclen)(OAc)2][PF6]2•H2O | AW050 | 1112.303 | 1.040 | 0.25 | 9.350E−07 |
| [Cu2(m-cyclam-homocyclen)(OAc)1.5][PF6]2.5 | AW051A | 1146.953 | 1.172 | 0.23 | 1.022E−06 |
| [Zn2(m-cyclam-homocyclen)(OAc)2][PF6]2 | AW052B | 1107.692 | 1.150 | 0.23 | 1.038E−06 |
| p-H2PBCyclams | SLK10 | 582.911 | 15.010 | 0.01 | 2.575E−05 |
| Bn2Cyclam | BME04 | 380.571 | 12.160 | 0.01 | 3.195E−05 |
| [Ni(Bn2Cyclam)(OAc)]PF6•H2O | BME06 | 661.287 | 17.990 | 0.01 | 2.720E−05 |
| [Co(Bn2Cyclam)(OAc)]PF6•H2O | BME07 | 661.215 | 6.980 | 0.02 | 1.056E−05 |
| Mn(Bn2Cyclam)Cl2•H2O | TJH397A | 524.429 | 16.870 | 0.01 | 3.217E−05 |
| [Zn(Bn2Cyclam)(OAc)]PF6 | SLK07B | 649.974 | 19.840 | 0.01 | 3.052E−05 |
| H2PBCyclam | DJD27 | 240.389 | 1.830 | 0.03 | 7.613E−06 |
| Fe(H2PBCyclam)Cl3•H2O | SLK36 | 420.607 | 3.330 | 0.03 | 7.917E−06 |
| Mn(H2PBCyclam)Cl3•3H2O | SLK37 | 455.730 | 1.780 | 0.06 | 3.906E−06 |
| [Co(H2PBCyclam)(OAc)]PF6•NH4PF6•H2O | SLK38B | 684.348 | 6.230 | 0.03 | 9.104E−06 |
| [Ni(H2PBCyclam)(OAc)]PF6•2NH4PF6 | SLK39B | 829.096 | 5.890 | 0.03 | 7.104E−06 |
| [Cu(H2PBCyclam)(OAc)]PF6•2NH4PF6 | SLK40B | 833.948 | 6.930 | 0.03 | 8.310E−06 |
| [Zn(H2PBCyclam)(OAc)]PF6•2.5NH4PF6 | SLK41 | 917.299 | 5.190 | 0.04 | 5.658E−06 |
| [Mn(Py-SB-Cyclam)Cl]PF6•3H2O | ADS17 | 606.874 | 5.220 | 0.03 | 8.601E−06 |
| [Fe(Py-SB-Cyclam)Cl]PF6 | ADS18C | 553.735 | 18.540 | 0.01 | 3.348E−05 |
| Ni(Py-SB-Cyclam)Cl2•3H2O | ADS20 | 501.117 | 18.590 | 0.01 | 3.710E−05 |
| Bn2PBCyclen | AW009 | 392.581 | 6.740 | 0.01 | 1.717E−05 |
| [Mn(Bn2PBCyclen)(C2H3O2)]PF6•2NH4PF6 | AW036 | 977.533 | 7.070 | 0.03 | 7.232E−06 |
| [Fe(Bn2PBCyclen)(C2H3O2)]PF6•1.2NH4PF6 | AW037 | 848.038 | 8.400 | 0.02 | 9.905E−06 |
| [Co(Bn2PBCyclen)(C2H3O2)]PF6 | AW038 | 655.523 | 4.370 | 0.04 | 6.666E−06 |
| [Ni(Bn2PBCyclen)(C2H3O2)]PF6 | AW039 | 655.283 | 7.640 | 0.02 | 1.166E−05 |
| [Cu(Bn2PBCyclen)(C2H3O2)0.4][PF6]1.6 | AW040 | 711.687 | 7.050 | 0.02 | 9.906E−06 |
| [Zn(Bn2PBCyclen)(C2H3O2)]PF6 | AW041 | 661.985 | 7.330 | 0.02 | 1.107E−05 |
| [Cu2(p-CB-Cyclens)(OAc)2][PF6]2 | JAV06 | 1061.922 | 10.900 | 0.02 | 1.026E−05 |
| [Cu2(m-CB-Cyclens)(OAc)2][PF6]2 | DJC06A | 1061.922 | 6.710 | 0.04 | 6.319E−06 |
| [Zn2(m-CB-Cyclens)(OAc)2][PF6]2 | DJC07 | 1065.590 | 7.410 | 0.03 | 6.954E−06 |
| [Cu2(p-CB-Homocyclens)(OAc)2][PF6]2 | ANC011 | 1089.274 | 4.190 | 0.06 | 3.847E−06 |
| [Ni2(p-CB-Homocyclens)(OAc)2][PF6]2 | TJH378A | 1080.264 | 7.540 | 0.03 | 6.980E−06 |
| [Co2(p-CB-Homocyclens)(OAc)2][PF6]2 | TJH379A | 1080.750 | 0.800 | 0.32 | 7.402E−07 |
| [Cu2(m-CB-Homocyclens)(OAc)2.5][PF6]1.5 | CDG035 | 1047.006 | 3.260 | 0.08 | 3.114E−06 |
| [Co2(m-CB-Homocyclens)(OAc)2.6][PF6]1.4 | CDG036 | 1029.189 | 3.040 | 0.08 | 2.954E−06 |
| [Zn2(m-CB-Homocyclens)(OAc)0.5][PF6]3.5 | CDG037 | 1222.546 | 1.620 | 0.18 | 1.325E−06 |
| [Ni2(m-CB-Homocyclens)(OAc)1.9][PF6]2.1 | CDG038 | 1088.853 | 3.010 | 0.09 | 2.764E−06 |

TABLE 2-continued

The in vitro Inhibitory Activity of the Macrocyclic Compounds Against *C. neoformans*

| Sample Code | Sample Code | Molecular Weight | *C. neoformans* IC$_{50}$ (μg/mL) | X more potent than Amphotericin B | *C. neoformans* IC$_{50}$ (mol/L) |
|---|---|---|---|---|---|
| [Cu2(m-CB-Cyclams)(OAc)2][PF6]2 | RM52 | 1118.029 | 0.820 | 0.32 | 7.334E−07 |
| [Zn2(m-CB-Cyclams)(OAc)2][PF6]2 | RM51 | 1121.697 | 1.850 | 0.14 | 1.649E−06 |
| [Ni2(m-CB-Cyclams)(OAc)2][PF6]2 | CDG009 | 1108.315 | 3.530 | 0.07 | 3.185E−06 |
| [Co2(m-CB-Cyclams)(OAc)2][PF6]4 | CDG010 | 1398.723 | 0.960 | 0.35 | 6.863E−07 |
| [Cu2(m-SB-Cyclams)(OAc)2][PF6]2 | KS24 | 1030.922 | 3.180 | 0.08 | 3.085E−06 |
| [Ni2(m-SB-Cyclams)(OAc)2][PF6]2 | KS25 | 1021.217 | 16.030 | 0.02 | 1.570E−05 |
| [Zn2(m-SB-Cyclams)(OAc)2][PF6]2 | KS26 | 1034.622 | 12.510 | 0.02 | 1.209E−05 |
| [Cu2(p-SB-Cyclens)(OAc)2][PF6]2 | OB28 | 1033.868 | 5.210 | 0.05 | 5.039E−06 |
| [Ni2(p-SB-Cyclens)(OAc)2][PF6]2•H2O | OB29 | 1042.171 | 0.800 | 0.31 | 7.676E−07 |
| [Co2(p-SB-Cyclens)(OAc)2][PF6]2•DMF | OB30 | 1097.737 | 0.800 | 0.33 | 7.288E−07 |
| [Cu2(m-SB-Cyclens)(OAc)2][PF6]2•2 H2O | OB34 | 1069.899 | 0.800 | 0.32 | 7.477E−07 |
| [Ni2(m-SB-Cyclens)(OAc)2][PF6]2•H2O | OB35 | 1042.171 | 0.800 | 0.31 | 7.676E−07 |
| [Co2(m-SB-Cyclens)(OAc)2][PF6]2•2H2O | OB36 | 1060.673 | 0.800 | 0.32 | 7.542E−07 |
| [Zn2(m-SB-Cyclens)(OAc)2][PF6]2•2H2O | OB37 | 1073.567 | 0.800 | 0.32 | 7.452E−07 |
| p-SB-Homocyclens | OB45 | 526.805 | 0.800 | 0.16 | 1.519E−06 |
| [Cu2(p-SB-Homocyclens)][PF6]4•2H2O | OB49 | 1269.783 | 0.800 | 0.38 | 6.300E−07 |
| m-SB-Homocyclens | OB46 | 526.805 | 4.850 | 0.03 | 9.206E−06 |
| [Co2(m-SB-Homocyclens)(OAc)2][PF6]2•H2O | OB55 | 1070.703 | 5.120 | 0.05 | 4.782E−06 |
| [Ni3(tris-SB-Cyclams)][PF6]6 | CDG024 | 1839.097 | 2.440 | 0.18 | 1.327E−06 |
| [Co3(tris-SB-Cyclams)(OAc)3][PF6]3 | CDG025 | 1582.068 | 1.800 | 0.21 | 1.138E−06 |
| [Zn3(tris-SB-Cyclams)(OAc)3][PF6]3•NH4PF6 | CDG026 | 1764.411 | 10.030 | 0.04 | 5.685E−06 |
| [Cu3(tris-SB-Cyclams)(OAc)3][PF6]3•1.5NH4PF6 | CDG027 | 1840.411 | 1.280 | 0.34 | 6.955E−07 |
| [Co3(tris-SB-Cyclens)(OAc)3][PF6]3 | CDG021 | 1497.907 | 0.800 | 0.45 | 5.341E−07 |
| [Cu3(tris-SB-Cyclens)(OAc)3][PF6]3•0.5NH4PF6 | CDG022 | 1593.247 | 5.480 | 0.07 | 3.440E−06 |
| [Zn3(tris-SB-Cyclens)(OAc)3][PF6]3•0.5NH4PF6 | CDG023 | 1598.749 | 1.310 | 0.29 | 8.194E−07 |
| [Ni3(tris-SB-Cyclens)OAc)3][PF6]3•H2O | CDG030 | 1515.193 | 0.800 | 0.45 | 5.280E−07 |
| [Ni3(tris-CB-Cyclams)(OAc)3][PF6]3•2.5H2O | BNS23 | 1668.457 | 12.110 | 0.03 | 7.258E−06 |
| [Co3(tris-CB-Cyclams)(OAc)1.5][PF6]4.5 | BNS24 | 1753.028 | 0.800 | 0.52 | 4.564E−07 |
| [Cu3(tris-CB-Cyclams)(OAc)3][PF6]3 | BNS25 | 1637.987 | 1.950 | 0.20 | 1.190E−06 |
| [Zn3(tris-CB-Cyclams)(OAc)3][PF6]3•2.4NH4PF6 | BNS26 | 2034.696 | 6.840 | 0.07 | 3.362E−06 |
| [Co3(tris-CB-Cyclens)(OAc)3][PF6]6 | BNS20 | 1974.880 | 1.000 | 0.47 | 5.064E−07 |
| [Cu3(tris-CB-Cyclens)(OAc)3][PF6]3 | BNS21 | 1553.826 | 1.320 | 0.28 | 8.495E−07 |
| [Zn3(tris-CB-Cyclens)(OAc)3][PF6]3•6H2O | BNS22 | 1667.420 | 3.410 | 0.12 | 2.045E−06 |
| [Co(Bn1Me1Bcyclen)(OAc)][PF6]2 | TRH15 | 710.369 | 0.800 | 0.21 | 1.126E−06 |
| [Co(Bn1Me1Bcyclam)(OAc)]PF6 | TRH16 | 593.453 | 9.190 | 0.02 | 1.549E−05 |
| [Co2(m-SB-cyclam-cyclen)(OAc)2][PF6]4•H2O | CMB032 | 1360.631 | 0.800 | 0.41 | 5.880E−07 |
| [Ni2(m-SB-cyclam-cyclen)(OAc)][PF6]3 | CMB033 | 1138.128 | 1.710 | 0.16 | 1.502E−06 |
| [Cu2(m-SB-cyclam-cyclen)(OAc)][PF6]3•2H2O | CMB034 | 1183.863 | 0.800 | 0.35 | 6.758E−07 |
| [Zn2(m-SB-cyclam-cyclen)(OAc)2][PF6]2•3.3H2O | CMB035 | 1125.063 | 0.800 | 0.33 | 7.111E−07 |
| [Co2(p-SB-cyclen-cyclen)(OAc)2][PF6]2 | CMB016A | 1052.696 | 1.570 | 0.16 | 1.491E−06 |
| [Ni2(p-SB-cyclam-cyclen)(OAc)][PF6]3•H2O | CMB017A | 1156.145 | 4.940 | 0.06 | 4.273E−06 |
| [Cu2(p-SB-cyclam-cyclen)(OAc)1.2][PF6]2.8 | CMB018 | 1130.658 | 3.020 | 0.09 | 2.671E−06 |
| p-CB-cyclam-cyclen | CMB008D | 554.858 | 0.800 | 0.17 | 1.442E−06 |
| [Co2(p-CB-cyclam-cyclen)(OAc)2][PF6]2 | CMB027 | 1080.750 | 0.800 | 0.32 | 7.402E−07 |
| [Ni2(p-CB-cyclam-cyclen)(OAc)2][PF6]2 | CMB028 | 1080.264 | 1.330 | 0.19 | 1.231E−06 |
| [Cu2(p-CB-cyclam-cyclen)(OAc)2][PF6]2 | CMB029 | 1089.976 | 0.800 | 0.32 | 7.340E−07 |
| [Zn2(p-CB-cyclam-cyclen)(OAc)][PF6]3•4H2O | CMB030 | 1251.624 | 1.380 | 0.22 | 1.103E−06 |
| [Zn(Me1-SB-Cyclen)(C2H3O2)]PF6 | DLM32 | 509.793 | 17.280 | 0.01 | 3.390E−05 |
| [Co(H2Bcyclam)(OAc)]PF6 | ANC25 | 489.304 | 4.360 | 0.03 | 8.911E−06 |
| [Co(Bcyclam)Cl2]PF6 | SAH06#2 | 529.218 | 19.220 | 0.01 | 3.632E−05 |
| [Mn(Bcyclen)Cl2]PF6 | CNV06 | 497.170 | 6.390 | 0.02 | 1.285E−05 |
| [Co(Bcyclen)Cl2]PF6 | DT06#2 | 500.051 | 3.390 | 0.04 | 6.779E−06 |
| [Co(H2Bcyclen)(OAc)]PF6 | ANC27A | 461.251 | 5.030 | 0.02 | 1.091E−05 |
| SB-BI-cyclen | SJA219 | 328.464 | 5.780 | 0.01 | 1.760E−05 |
| CB-BI-cyclen | SJA220 | 342.491 | 5.160 | 0.02 | 1.507E−05 |
| [Zn(SB-BI-cyclen)(Cl)2] | SJA222 | 328.464 | 2.610 | 0.03 | 7.946E−06 |
| [Zn(CB-BI-cyclen)(OAc)2] | SJA225 | 342.491 | 5.690 | 0.01 | 1.661E−05 |
| [Mn(CB-BI-cyclen)(Cl)2] | SJA227 | 342.491 | 1.930 | 0.04 | 5.635E−06 |
| SB-BINO2-cyclen | SJA229 | 463.586 | 1.890 | 0.06 | 4.077E−06 |
| CB-BINO2-cyclen | SJA230 | 477.613 | 7.930 | 0.01 | 1.660E−05 |
| [Ni(SB-BINO2-cyclen)(OAc)2] | SJA232 | 463.586 | 5.070 | 0.02 | 1.094E−05 |
| Bis-SB-C—Ar—NO2 | SJA233 | 689.980 | 0.550 | 0.30 | 7.971E−07 |
| [Cu2(bis-SB-C—Ar—NO2)(ClO4)4] | SJA234 | 1214.870 | 1.910 | 0.15 | 1.572E−06 |
| [Zn2(bis-SB-C—Ar—NO2)(OAc)4] | SJA235 | 1056.910 | 1.930 | 0.13 | 1.826E−06 |
| [Ni2(bis-SB-C—Ar—NO2)(NO3)4] | SJA236 | 1055.380 | 0.740 | 0.34 | 7.012E−07 |
| [Mn(Bcyclen)Cl2]PF6 | CNV06 | 497.170 | 5.579 | 0.02 | 1.122E−05 |
| [Mn(B13N4)Cl2]PF6 | DLM10 | 511.197 | 9.522 | 0.01 | 1.863E−05 |
| [Mn(pic1Me1-CB-Cyclen)Cl]Cl | KRW37 | 429.290 | 3.076 | 0.03 | 7.166E−06 |
| [Mn(Bn1Me1-CB-Cyclam)Cl2] | NS11 | 456.355 | 5.038 | 0.02 | 1.104E−05 |
| {[Mn(4,10-bis(7-chloroquinoline)cyclen]Cl2} | K-PAA2-0004-P8-TJH410 | 621.291 | 4.123 | 0.04 | 6.637E−06 |

TABLE 3

The in vitro Inhibitory Activity of the Macrocyclic Compounds Against *L. donovani*

| Sample Code | Sample Code | Molecular Weight | *L. donovani* IC$_{50}$ (µg/mL) | X more potent than Pentamidine | *L. donavani* IC$_{50}$ (mol/L) |
|---|---|---|---|---|---|
| Pentamidine | PENT | 340.420 | 1.81 | 1.00 | 5.317E−06 |
| [Mn2(H2-p-CB-cyclams)][MnCl4]2 | TJH412 | 1058.231 | 33.37 | 0.17 | 3.153E−05 |
| [Zn2(H2-p-CB-cyclams)(OAc)2][PF6]2•H2O | TJH417B | 1111.681 | 34.93 | 0.17 | 3.142E−05 |
| Bn2PBCyclam | SLK09 | 420.645 | 2.56 | 0.87 | 6.086E−06 |
| [Mn(Bn2PBCyclam)][MnCl4] | BME08 | 672.321 | 1.78 | 2.01 | 2.648E−06 |
| [Fe(Bn2PBCyclam)][FeCl4]•H2O | BME09 | 692.150 | 14.10 | 0.26 | 2.037E−05 |
| [Cu(Bn2PBCyclam)(OAc)]PF6•2.5 H2O | BME10B | 733.227 | 3.64 | 1.07 | 4.964E−06 |
| Cu(Bn2PBCyclam)(OAc)2 | DJD20 | 602.281 | 14.65 | 0.22 | 2.432E−05 |
| [Co(Bn2P8Cyclam)(OAc)]PF6 | DJD21 | 683.587 | 14.12 | 0.26 | 2.066E−05 |
| [Ni(Bn2P8Cyclam)(OAc)]PF6 | DJD22 | 683.344 | 13.10 | 0.28 | 1.917E−05 |
| [Zn(Bn2PBCyclam)(OAc)]PF6 | DJD23 | 690.044 | 4.32 | 0.85 | 6.260E−06 |
| [p-(BMBCyclams)]Br2 | SLK17A | 712.568 | 16.69 | 0.23 | 2.342E−05 |
| [p-(DCP-BMBCyclams)]Br4 | SLK26 | 1194.494 | 14.76 | 0.43 | 1.236E−05 |
| [m-(BMBCyclams)]Br2 | DJD05 | 712.568 | 18.18 | 0.21 | 2.551E−05 |
| [Co2(m-cyclam-homocyclen)(OAc)2][PF6]2 | AW049 | 1094.768 | 16.93 | 0.34 | 1.546E−05 |
| [Ni2(m-cyclam-homocyclen)(OAc)2][PF6]2•H2O | AW050 | 1112.303 | 16.50 | 0.36 | 1.483E−05 |
| [Zn2(m-cyclam-homocyclen)(OAc)2][PF6]2 | AW052B | 1107.692 | 17.60 | 0.33 | 1.589E−05 |
| p-H2PBCyclams | SLK10 | 582.911 | 15.50 | 0.20 | 2.659E−05 |
| Bn2Cyclam | BME04 | 380.571 | 2.63 | 0.77 | 6.911E−06 |
| [Ni(Bn2Cyclam)(OAc)]PF6•H2O | BME06 | 661.287 | 26.25 | 0.13 | 3.970E−05 |
| Mn(Bn2Cyclam)Cl2•H2O | TJH397A | 524.429 | 2.31 | 1.21 | 4.405E−06 |
| Fe(Bn2Cyclam)Cl2•0.5 H2O | TJH398A | 516.328 | 2.28 | 1.20 | 4.416E−06 |
| (Zn(Bn2Cyclam)(OAc)]PF6 | SLK07B | 649.974 | 2.97 | 1.16 | 4.569E−06 |
| (DCP)2Cyclam | DJD29 | 520.336 | 9.76 | 0.28 | 1.876E−05 |
| Bn2PBCyclen | AW009 | 392.581 | 21.40 | 0.10 | 5.451E−05 |
| [Mn(Bn2PBCyclen)(C2H3O2)]PF6•2NH4PF6 | AW036 | 977.533 | 25.41 | 0.20 | 2.599E−05 |
| [Fe(Bn2PBCyclen)(C2H3O2)]PF6•1.2NH4PF6 | AW037 | 848.038 | 26.63 | 0.17 | 3.140E−05 |
| [Co(Bn2PBCyclen)(C2H3O2)]PF6 | AW038 | 655.523 | 20.66 | 0.17 | 3.152E−05 |
| [Ni(Bn2PBCyclen)(C2H3O2)]PF6 | AW039 | 655.283 | 24.41 | 0.14 | 3.725E−05 |
| [Zn(Bn2PBCyclen)(C2H3O2)]PF6 | AW041 | 661.985 | 22.92 | 0.15 | 3.462E−05 |
| [Cu2(m-CB-Homocyclens)(OAc)2.5][PF6]1.5 | CDG035 | 1047.006 | 26.37 | 0.21 | 2.519E−05 |
| [Co2(m-CB-Homocyclens)(OAc)2.6][PF6]1.4 | CDG036 | 1029.189 | 22.23 | 0.25 | 2.160E−05 |
| [Ni2(m-CB-Homocyclens)(OAc)1.9][PF6]2.1 | CDG038 | 1088.853 | 19.92 | 0.29 | 1.829E−05 |
| [Zn2(m-CB-Cyclams)(OAc)2][PF6]2 | RM51 | 1121.697 | 19.82 | 0.30 | 1.767E−05 |
| p-SB-Homocyclens | OB45 | 526.805 | 17.44 | 0.16 | 3.311E−05 |
| [Ni3(tris-CB-Cyclams)(OAc)3][PF6]3•2.5H2O | BNS23 | 1668.457 | 31.63 | 0.28 | 1.896E−05 |
| [Cu(Bn1Me1Bcyclam)(OAc)]PF6 | RM56A | 598.072 | 33.32 | 0.10 | 5.571E−05 |
| [Ni(Bn1Me1Bcyclam)(OAc)]PF6•0.5NH4PF6 | TRH11B | 647.717 | 38.64 | 0.09 | 5.966E−05 |
| [Co2(p-SB-cyclam-cyclen)(OAc)2][PF6]2 | CMB016A | 1052.696 | 33.81 | 0.17 | 3.212E−05 |
| p-CB-cyclam-cyclen | CMB008D | 554.858 | 38.75 | 0.08 | 6.984E−05 |
| [Co2(p-CB-cyclam-cyclen)(OAc)2][PF6]2 | CMB027 | 1080.750 | 32.62 | 0.18 | 3.018E−05 |
| [Ni2(p-CB-cyclam-cyclen)(OAc)2][PF6]2 | CMB028 | 1080.264 | 30.69 | 0.19 | 2.841E−05 |
| [Zn2(p-CB-cyclam-cyclen)(OAc)2][PF6]3•4H2O | CMB030 | 1251.624 | 31.32 | 0.21 | 2.502E−05 |
| p-CB-cyclens HCl salt | OB15B | 872.115 | 20.94 | 0.22 | 2.401E−05 |
| m-CB-homocyclens HCl salt | OB65B | 990.676 | 11.08 | 0.48 | 1.118E−05 |
| m-CB-cyclens HCl salt | DJC05C | 890.561 | 22.89 | 0.21 | 2.570E−05 |
| p-CB-homocyclens HCl salt | TA22C | 928.223 | 16.31 | 0.30 | 1.757E−05 |
| m-CB-cyclams HCl salt | TJS04 | 973.692 | 10.37 | 0.50 | 1.065E−05 |
| m-SB-cyclams HCl salt | KS22B | 918.615 | 17.61 | 0.28 | 1.917E−05 |
| p-SB-cyclens HCl salt | OB24B | 863.104 | 32.40 | 0.14 | 3.754E−05 |
| m-SB-cyclens HCl salt | OB25B | 926.161 | 11.45 | 0.43 | 1.236E−05 |
| p-SB-homocyclens HCl salt | OB45B | 818.500 | 34.55 | 0.13 | 4.221E−05 |
| m-SB-homocyclens HCl salt | OB46B | 818.500 | 34.26 | 0.13 | 4.186E−05 |
| tris-SB-cyclams | CDG19 | 793.242 | 15.91 | 0.27 | 2.006E−05 |
| tris-SB-cyclens | CDG29 | 709.081 | 11.69 | 0.32 | 1.649E−05 |
| tris-CB-cyclens | BNS017 | 751.162 | 25.46 | 0.16 | 3.389E−05 |
| tris-CB-cyclams | BNS018 | 835.323 | 7.73 | 0.57 | 9.254E−06 |
| (dcp)1-SB-cyclen | OB99 | 358.314 | 20.87 | 0.09 | 5.825E−05 |
| [Ni(dcp1-SB-cyclen)(OAc)]PF6 | OB106 | 621.013 | 23.19 | 0.14 | 3.734E−05 |
| [Zn(dcp1-SB-cyclen)(OAc)]PF6 | OB110A | 758.105 | 38.32 | 0.11 | 5.055E−05 |
| [Zn2(p-CB-cyclams)(OAc)2](PF6)2 | KS34 | 1121.697 | 23.49 | 0.25 | 2.094E−05 |
| Bn2Bcyclam | JGL45 | 406.610 | 3.94 | 0.55 | 9.690E−06 |
| Mn(Bn2Bcyclam)Cl2 | NS06 | 532.458 | 21.99 | 0.13 | 4.130E−05 |
| Fe(Bn2Bcyclam)Cl2 | NS08 | 533.367 | 1.71 | 1.66 | 3.206E−06 |
| [Zn(Bn2Bcyclam)(OAc)]PF6 | RM41 | 676.003 | 9.51 | 0.38 | 1.407E−05 |
| [Cu(Bn2Bcyclam)(OAc)]PF6 | RM37 | 674.169 | 6.17 | 0.58 | 9.152E−06 |
| [Co(Bn2Bcyclam)(OAc)]PF6 | TC11 | 669.557 | 35.29 | 0.10 | 5.271E−05 |
| [Ni(Bn2Bcyclam)(OAc)]PF6 | TC09 | 669.313 | 6.51 | 0.55 | 9.726E−06 |
| Bn2Bcyclen | ANC14 | 378.564 | 3.80 | 0.53 | 1.004E−05 |
| Mn(Bn2Bcyclen)Cl2 | NS29 | 504.405 | 7.70 | 0.35 | 1.527E−05 |
| [Ni(Bn2Bcyclen)(OAc)]PF6 | TC10 | 641.260 | 10.95 | 0.31 | 1.708E−05 |
| [Zn(Bn2Bcyclen)(OAc)]PF6 | RM42 | 647.950 | 4.73 | 0.73 | 7.300E−06 |
| p-CB-H2Bcyclams | JGL44 | 554.872 | 28.08 | 0.11 | 5.061E−05 |
| p-CB-H2Bcyclens | JGL19 | 498.764 | 8.54 | 0.31 | 1.712E−05 |
| p-dcp2-CB-cyclens | PW111A | 818.764 | 12.89 | 0.34 | 1.574E−05 |

TABLE 3-continued

The in vitro Inhibitory Activity of the Macrocyclic Compounds Against *L. donovani*

| Sample Code | Sample Code | Molecular Weight | *L. donovani* IC$_{50}$ (µg/mL) | X more potent than Pentamidine | *L. donovani* IC$_{50}$ (mol/L) |
|---|---|---|---|---|---|
| Bis-SB-C—Ar—NO2 | SJA233 | 689.980 | 30.32 | 0.12 | 4.394E−05 |
| [Cu2(bis-SB-C—Ar—NO2)(ClO4)4] | SJA234 | 1214.870 | 30.31 | 0.21 | 2.495E−05 |
| [Zn2(bis-SB-C—Ar—NO2)(OAc)4] | SJA235 | 1056.910 | 34.77 | 0.16 | 3.290E−05 |
| [Ni2(bis-SB-C—Ar—NO2)(NO3)4] | SJA236 | 1055.380 | 24.85 | 0.23 | 2.355E−05 |

TABLE 4

The in vitro Inhibitory Activity of the Macrocyclic Compounds Against *C. krusei*

| Sample Code | Sample Code | Molecular Weight | *C. krusei* IC$_{50}$ (µg/mL) | X more potent than amphotericin B | *C. krusei* IC$_{50}$ (mol/L) |
|---|---|---|---|---|---|
| Amphotericin B | AMB | 923.490 | 1.380 | 1.00 | 1.494E−06 |
| m-SB-cyclens HCl salt | OB25B | 926.161 | 6.530 | 0.21 | 7.051E−06 |
| m-SB-homocyclens HCl salt | OB46B | 818.500 | 7.420 | 0.16 | 9.065E−06 |
| tris-SB-cyclams | CDG19 | 793.242 | 4.790 | 0.25 | 6.039E−06 |
| tris-SB-cyclens | CDG29 | 709.081 | 4.660 | 0.23 | 6.572E−06 |
| tris-CB-cyclens | BNS017 | 751.162 | 5.850 | 0.19 | 7.788E−06 |
| (dcp)1-SB-cyclen | OB99 | 358.314 | 5.660 | 0.09 | 1.580E−05 |
| [Cu2(p-CB-cyclams)(OAc)2][PF6)2 | TJH384A | 1118.030 | 6.760 | 0.25 | 6.046E−06 |
| [Ni(Bn2Bcyclam)(OAc)]PF6 | TC09 | 669.313 | 4.520 | 0.22 | 6.753E−06 |
| CB-BINO2-cyclen | SJA230 | 477.600 | 7.690 | 0.09 | 1.610E−05 |
| Bis-SB-C—Ar—NO2 | SJA233 | 689.980 | 4.070 | 0.25 | 5.899E−06 |
| [Cu2(bis-SB-C—Ar—NO2)(ClO4)4] | SJA234 | 1214.870 | 4.550 | 0.40 | 3.745E−06 |
| [Ni2(bis-SB-C—Ar—NO2)(NO3)4] | SJA236 | 1055.380 | 6.030 | 0.26 | 5.714E−06 |
| [Mn(Bn2PBCyclam)](MnCl4) | BME08 | 672.321 | 5.270 | 0.19 | 7.839E−06 |
| [Ni(Bn2PBCyclam)(OAc)]PF6 | DJD22 | 683.344 | 5.250 | 0.19 | 7.683E−06 |
| [p-(BMBCyclams)]Br2 | SLK17A | 712.568 | 0.880 | 1.21 | 1.235E−06 |
| [Co2(m-cyclam-homocyclen)(OAc)2][PF6]2 | AW049 | 1094.768 | 6.520 | 0.25 | 5.956E−06 |
| Bn2PBCyclen | AW009 | 392.581 | 6.170 | 0.10 | 1.572E−05 |
| (Mn(Bn2PBCyclen)(C2H3O2)]PF6•2NH4PF6 | AW036 | 977.533 | 4.990 | 0.29 | 5.105E−06 |
| [Ni(Bn2PBCyclen)(C2H3O2)]PF6 | AW039 | 655.283 | 5.610 | 0.17 | 8.561E−06 |
| [Zn(Bn2PBCyclen)(C2H3O2)]PF6 | AW041 | 661.985 | 5.170 | 0.19 | 7.810E−06 |
| [Cu2(m-SB-Cyclens)(OAc)2][PF6]2•2 H2O | OB34 | 1069.899 | 5.780 | 0.28 | 5.402E−06 |
| [Ni2(m-SB-Cyclens)(OAc)2][PF6]2•H2O | OB35 | 1042.171 | 0.800 | 1.95 | 7.676E−07 |
| p-SB-Homocyclens | OB45 | 526.805 | 0.800 | 0.98 | 1.519E−06 |
| [Co3(tris-SB-Cyclens)(OAc)3][PF6]3 | CDG021 | 1497.907 | 4.200 | 0.53 | 2.804E−06 |
| [Zn3(tris-CB-Cyclams)(OAc)3][PF6]3•2.4NH4PF6 | BNS26 | 2034.696 | 1.220 | 2.49 | 5.996E−07 |
| [Co3(tris-CB-Cyclens)(OAc)3][PF6]6 | BNS20 | 1974.880 | 0.980 | 3.01 | 4.962E−07 |

TABLE 5

The in vitro Inhibitory Activity of the Macrocyclic Compounds Against *C. glabrata*

| Sample Code | Sample Code | Molecular Weight | C glabrata IC$_{50}$ (µg/mL) | X more potent than amphotericin B | *C. glabrata* IC$_{50}$ (mol/L) |
|---|---|---|---|---|---|
| Amphotericin B | AMB | 923.490 | 1.310 | 1.00 | 1.419E−06 |
| tris-SB-cyclams | CDG19 | 793.242 | 9.800 | 0.11 | 1.235E−05 |
| Mn2(p-CB-cyclams)Cl4 | JGL16A | 834.608 | 18.600 | 0.06 | 2.229E−05 |
| [Cu2(p-CB-cyclams)(OAc)2](PF6)2 | TJH384A | 1118.030 | 14.590 | 0.11 | 1.305E−05 |
| [Zn2(p-CB-cyclams)(OAc)2](PF6)2 | KS34 | 1121.697 | 15.760 | 0.10 | 1.405E−05 |
| Me1Pic1-CB-cyclen | KRW32 | 303.454 | 14.360 | 0.03 | 4.732E−05 |
| [Co(dcp-SB-cyclam)(OAc)]PF6 | KLC002A | 649.310 | 16.070 | 0.06 | 2.475E−05 |
| [Co(pic-SB-cyclen)Cl]PF6 | KRW45 | 537.782 | 5.200 | 0.15 | 9.669E−06 |
| pic2-CB-cyclen | PW95 | 380.540 | 14.850 | 0.04 | 3.902E−05 |
| [p-(BMBCyclams)]Br2 | SLK17A | 712.568 | 1.317 | 0.77 | 1.848E−06 |
| [p-(DCP-BMBCyclams)]Br4 | SLK26 | 1194.494 | 5.705 | 0.30 | 4.776E−06 |
| [m-(BMBCyclams)]Br2 | DJD05 | 712.568 | 4.213 | 0.24 | 5.912E−06 |
| [Co2(m-cyclam-homocyclen)(OAc)2][PF6]2 | AW049 | 1094.768 | 1.217 | 1.28 | 1.112E−06 |
| [Cu2(m-cyclam-homocyclen)(OAc)1.5][PF6]2.5 | AW051A | 1146.953 | 7.253 | 0.22 | 6.324E−06 |
| [Co(Bn2Cyclam)(OAc)PF6•H2O | BME07 | 661.215 | 0.597 | 1.57 | 9.029E−07 |
| H2PBCyclam | DJD27 | 240.389 | 3.380 | 0.10 | 1.406E−05 |
| [Co(H2PBCyclam)(OAc)]PF6•NH4PF6•H2O | SLK38B | 684.348 | 0.375 | 2.59 | 5.480E−07 |
| Co(Py-SB-Cyclam)Cl2•2.2H2O | ADS19 | 486.945 | 5.160 | 0.13 | 1.060E−05 |
| [Co(Bn2PBCyclen)(C2H3O2)]PF6 | AW038 | 655.523 | 5.800 | 0.16 | 8.848E−06 |

TABLE 5-continued

The in vitro Inhibitory Activity of the Macrocyclic Compounds Against *C. glabrata*

| Sample Code | Sample Code | Molecular Weight | C glabrata IC$_{50}$ (μg/mL) | X more potent than amphotericin B | C. glabrata IC$_{50}$ (mol/L) |
|---|---|---|---|---|---|
| [Ni(Bn2PBCyclen)(C2H3O2)]PF6 | AW039 | 655.283 | 5.030 | 0.18 | 7.676E−06 |
| [Ni2(p-CB-Homocyclens)(OAc)2][PF6]2 | TJH378A | 1080.264 | 5.150 | 0.30 | 4.767E−06 |
| [Cu2(m-CB-Cyclams)(OAc)2][PF6]2 | RM52 | 1118.029 | 4.940 | 0.32 | 4.418E−06 |
| [Ni2(m-CB-Cyclams)(OAc)2][PF6]2 | CDG009 | 1108.315 | 5.150 | 0.31 | 4.647E−06 |
| [Co2(p-SB-Cyclens)(OAc)2][PF6]2•DMF | OB30 | 1097.737 | 0.800 | 1.95 | 7.288E−07 |
| [Co2(m-SB-Cyclens)(OAc)2][PF6]2•2H2O | OB36 | 1060.673 | 3.720 | 0.40 | 3.507E−06 |
| [Co3(tris-SB-Cyclams)(OAc)3][PF6]3 | CDG025 | 1582.068 | 1.500 | 1.50 | 9.481E−07 |
| [Zn3(tris-SB-Cyclams)(OAc)3][PF6]3•NH4PF6 | CDG026 | 1764.411 | 3.420 | 0.73 | 1.938E−06 |
| [Cu3(tris-SB-Cyclams)(OAc)3][PF6]3•1.5NH4PF6 | CDG027 | 1840.411 | 1.630 | 1.60 | 8.857E−07 |
| [Co3(tris-SB-Cyclens)(OAc)3][PF6]3 | CDG021 | 1497.907 | 0.800 | 2.66 | 5.341E−07 |
| [Ni3(tris-SB-Cyclens)OAc)3][PF6]3•H2O | CDG030 | 1515.193 | 4.170 | 0.52 | 2.752E−06 |
| [Co3(tris-CB-Cyclams)(OAc)1.5][PF6]4.5 | BNS24 | 1753.028 | 1.490 | 1.67 | 8.500E−07 |
| [Cu3(tris-CB-Cyclams)(OAc)3][PF6]3 | BNS25 | 1637.987 | 5.420 | 0.43 | 3.309E−06 |
| [Zn3(tris-CB-Cyclams)(OAc)3][PF6]3•2.4NH4PF6 | BNS26 | 2034.696 | 2.140 | 1.35 | 1.052E−06 |
| [Ni3(tris-CB-Cyclens)(OAc)3][PF6]3•6H2O | BNS19 | 1647.350 | 4.900 | 0.48 | 2.974E−06 |
| [Co3(tris-CB-Cyclens)(OAc)3][PF6]6 | BNS20 | 1974.880 | 4.720 | 0.59 | 2.390E−06 |
| [Co2(m-SB-cyclam-cyclen)(OAc)2][PF6]4•H2O | CMB032 | 1360.631 | 1.310 | 1.47 | 9.628E−07 |
| [Co2(p-SB-cyclam-cyclen)(OAc)2][PF6]2 | CMB016A | 1052.696 | 1.100 | 1.36 | 1.045E−06 |
| [Co2(p-CB-cyclam-cyclen)(OAc)2][PF6]2 | CMB027 | 1080.750 | 1.320 | 1.16 | 1.221E−06 |
| [Ni2(p-CB-cyclam-cyclen)(OAc)2][PF6]2 | CMB028 | 1080.264 | 4.490 | 0.34 | 4.156E−06 |
| [Cu2(p-CB-cyclam-cyclen)(OAc)2][PF6]2 | CMB029 | 1089.976 | 4.190 | 0.37 | 3.844E−06 |
| [Zn2(p-CB-cyclam-cyclen)(OAc)][PF6]3•4H2O | CMB030 | 1251.624 | 4.190 | 0.42 | 3.348E−06 |
| [Ni2(bis-SB-C—Ar—NO2)(NO3)4] | SJA236 | 1055.380 | 5.750 | 0.26 | 5.448E−06 |

TABLE 6

The in vitro Inhibitory Activity of the Macrocyclic Compounds Against *P. falciparum*

| Sample Code | Sample Code | Molecular Weight | P. falciparum D6 IC$_{50}$ (μg/mL) | X more potent than chloroquine | P. falciparum D6 IC$_{50}$ (mol/L) | P. falciparum W2 IC50 (μg/mL) | X more potent than chloroquine | P. falciparum W2 IC$_{50}$ (mol/L) |
|---|---|---|---|---|---|---|---|---|
| Chloroquine | CQ | 319.872 | 0.0117 | 1.00 | 3.658E−08 | 0.2170 | 1.00 | 6.784E−07 |
| m-CB-homocyclens HCl salt | OB65B | 990.676 | 0.2921 | 0.12 | 2.948E−07 | 0.3783 | 1.78 | 3.819E−07 |
| p-CB-homocyclens HCl salt | TA22C | 842.229 | 0.2596 | 0.12 | 3.082E−07 | 0.3189 | 1.79 | 3.786E−07 |
| Mn2(p-CB-cyclams)Cl4 | JGL16A | 834.608 | 0.7989 | 0.04 | 9.572E−07 | 0.8002 | 0.71 | 9.588E−07 |
| Bn2Bcyclam | JGL45 | 406.610 | 1.0894 | 0.01 | 2.679E−06 | 0.1772 | 1.56 | 4.358E−07 |
| Mn(Bn2Bcyclam)Cl2 | NS06 | 532.458 | 0.0838 | 0.23 | 1.574E−07 | 0.0674 | 5.36 | 1.266E−07 |
| Fe(Bn2Bcyclam)Cl2 | NS08 | 533.367 | 0.1726 | 0.11 | 3.236E−07 | 0.2271 | 1.59 | 4.258E−07 |
| [Zn(Bn2Bcyclam)(OAc)]PF6 | RM41 | 676.003 | 0.2315 | 0.11 | 3.425E−07 | 0.4010 | 1.14 | 5.932E−07 |
| [Cu(Bn2Bcyclam)(OAc)]PF6 | RM37 | 674.169 | 0.2855 | 0.09 | 4.235E−07 | 0.5451 | 0.84 | 8.086E−07 |
| Mn(Bn2Bcyclen)Cl2 | NS29 | 504.405 | 0.1337 | 0.14 | 2.651E−07 | 0.2747 | 1.25 | 5.446E−07 |
| [Cu(Bn2Bcyclen)(OAc)]PF6 | RM58 | 646.116 | 0.0947 | 0.25 | 1.466E−07 | 0.2015 | 2.18 | 3.119E−07 |
| Fe(Bn1Me1Bcyclam)Cl2 | NS12 | 457.270 | 0.1371 | 0.12 | 2.998E−07 | 0.1164 | 2.67 | 2.546E−07 |
| 4,10-bis(7-chloroquinoline)-1,7-dimethylcyclen | K-PAA-0012-P28 | 523.501 | 0.1169 | 0.16 | 2.233E−07 | 0.1992 | 1.78 | 3.805E−07 |
| Fe-complex-4,10-bis(chloroquinoline)cyclen | K-PAA-0016-P36 | 885.660 | 0.0196 | 1.65 | 2.213E−08 | 0.0336 | 17.88 | 3.794E−08 |
| [Mn(Bn1Me1-CB-Cyclam)Cl2] | NS11 | 456.355 | 0.6142 | 0.03 | 1.346E−06 | 0.5300 | 0.58 | 1.161E−06 |
| {[Mn(4,10-bis(7-chloroquinoline)cyclen]Cl2} | K-PAA2-0004-P8 | 622.200 | 0.0750 | 0.30 | 1.205E−07 | 0.0875 | 4.82 | 1.406E−07 |
| [Fe(Me1Py1-CB-Cyclam)Cl]PF6 | DGJ011 | 567.761 | 0.9983 | 0.02 | 1.758E−06 | 1.0356 | 0.37 | 1.824E−06 |
| [Mn(Bn2PBCyclam)][MnCl4] | BME08 | 672.321 | 0.0967 | 0.25 | 1.438E−07 | 0.1206 | 3.78 | 1.794E−07 |
| [Ni(Bn2PBCyclam)(OAc)]PF6 | DJD22 | 683.344 | 0.7074 | 0.04 | 1.035E−06 | 0.9060 | 0.51 | 1.326E−06 |
| p-H2PBCyclams | SLK10 | 582.911 | 0.8657 | 0.02 | 1.485E−06 | 1.7920 | 0.22 | 3.074E−06 |
| [Ni(Bn2Cyclam)(OAc)]PF6•H2O | BME06 | 661.287 | 0.7495 | 0.03 | 1.133E−06 | 1.7132 | 0.26 | 2.591E−06 |
| Bn2PBCyclen | AW009 | 392.581 | 1.0770 | 0.01 | 2.743E−06 | 1.5560 | 0.17 | 3.964E−06 |
| [Cu(Bn1Me1Bcyclam)(OAc)]PF6 | RM56A | 598.072 | 0.7145 | 0.03 | 1.195E−06 | 0.6747 | 0.60 | 1.128E−06 |
| [Mn(Bcyclam)Cl2]PF6 | OB15B | 526.818 | 0.5799 | 0.03 | 1.101E−06 | 0.6558 | 0.54 | 1.245E−06 |
| m-CB-cyclams HCl salt | TJS04 | 874.590 | 0.7450 | 0.04 | 8.518E−07 | 0.6558 | 0.90 | 7.498E−07 |
| [Ni(Bn2Bcyclam)(OAc)]PF6 | TC09 | 669.32 | 0.552 | 0.04 | 8.247E−07 | 0.8876 | 0.51 | 1.326E−06 |
| Bn2Bcyclen | ANC14 | 378.564 | 0.5110 | 0.03 | 1.35E−06 | 0.7602 | 0.34 | 2.008E−06 |
| Bis-crossbridge-Cyclam | K-PAA2-0009-P18 | 549.544 | 1.148 | 0.02 | 2.089E−06 | 2.1477 | 0.17 | 3.908E−06 |
| Tris-Cyclam | K-PAA2-0016-P32 | 685.094 | 0.0316 | 0.79 | 4.613E−08 | 0.0361 | 12.87 | 5.269E−08 |

TABLE 6-continued

The in vitro Inhibitory Activity of the Macrocyclic Compounds Against *P. falciparum*

| Sample Code | Sample Code | Molecular Weight | *P. falciparum* D6 IC$_{50}$ (μg/mL) | X more potent than chloroquine | *P. falciparum* D6 IC$_{50}$ (mol/L) | *P. falciparum* W2 IC50 (μg/mL) | X more potent than chloroquine | *P. falciparum* W2 IC$_{50}$ (mol/L) |
|---|---|---|---|---|---|---|---|---|
| Bis-tridecane | K-AVR-0005-P10-D1 | 509.479 | 0.1508 | 0.12 | 2.96E−07 | 0.1317 | 2.62 | 2.585E−07 |
| Bis-crossbridge-Cyclen | K-PAA2-0023-P46 | 521.49 | 0.1907 | 0.10 | 3.657E−07 | 0.6075 | 0.58 | 1.165E−06 |
| Cu complex of Cyclen bisquinoline | K-AVR-0009-P32 | 677.086 | 0.1732 | 0.14 | 2.558E−07 | 0.5625 | 0.82 | 8.308E−07 |
| Bis-BQ-Cyclen | K-AVR-0008-P30 | 698.561 | 2.1001 | 0.01 | 3.006E−06 | 3.3869 | 0.14 | 4.848E−06 |
| Pentadecane Mono | K-JDD-0011-P36 | 375.945 | 0.0203 | 0.68 | 5.4E−08 | 0.5279 | 0.48 | 1.404E−06 |

TABLE 7

The in vitro Inhibitory Activity of the Macrocyclic Compounds Against *S.aureus*

| Sample Code | Sample Code | Molecular Weight | *S.aureus* IC$_{50}$ (μg/mL) | X more potent than ciprofloxacen | *S.aureus* IC$_{50}$ (mol/L) |
|---|---|---|---|---|---|
| Ciprofloxacen | CIPRO | 331.346 | 0.090 | 1.00 | 2.716E−07 |
| m-CB-cyclams HCl salt | TJS04 | 973.692 | 9.280 | 0.03 | 9.531E−06 |
| m-SB-cyclens HCl salt | OB25B | 926.161 | 5.940 | 0.04 | 6.414E−06 |
| (dcp)1-SB-cyclen | OB99 | 358.314 | 7.520 | 0.01 | 2.099E−05 |
| Mn2(p-CB-cyclams)Cl4 | JGL16A | 834.608 | 8.090 | 0.03 | 9.693E−06 |
| [Ni2(p-CB-cyclams)(OAc)2](PF6)2 | KS33 | 1108.317 | 8.490 | 0.04 | 7.660E−06 |
| Mn(Bn2Bcyclam)Cl2 | NS06 | 532.458 | 2.310 | 0.06 | 4.338E−06 |
| Bn2Bcyclen | ANC14 | 378.564 | 8.810 | 0.01 | 2.327E−05 |
| Mn(Bn2Bcyclen)Cl2 | NS29 | 504.405 | 5.880 | 0.02 | 1.166E−05 |
| p-CB-H2Bcyclens | JGL19 | 498.764 | 2.900 | 0.05 | 5.814E−06 |
| p-dcp2-CB-cyclens | PW111A | 818.764 | 5.530 | 0.04 | 6.754E−06 |
| Bn2PBCyclam | SLK09 | 420.645 | 2.270 | 0.05 | 5.396E−06 |
| [Mn(Bn2PBCyclam)][MnCl4] | BME08 | 672.321 | 0.800 | 0.23 | 1.190E−06 |
| [Fe(Bn2PBCyclam)][FeCl4]•H2O | BME09 | 692.15 | 5.130 | 0.04 | 7.412E−06 |
| [Cu(Bn2PBCyclam)(OAc)]PF6•2.5 H2O | BME10B | 733.227 | 5.670 | 0.04 | 7.733E−06 |
| Cu(Bn2PBCyclam)(OAc)2 | DJD20 | 602.281 | 6.880 | 0.02 | 1.142E−05 |
| [Co(Bn2PBCyclam)(OAc)]PF6 | DJD21 | 683.587 | 3.590 | 0.05 | 5.252E−06 |
| [Ni(Bn2PBCyclam)(OAc)]PF6 | DJD22 | 683.344 | 4.630 | 0.04 | 6.776E−06 |
| [Zn(Bn2PBCyclam)(OAc)]PF6 | DJD23 | 690.044 | 6.530 | 0.03 | 9.463E−06 |
| [Mn2(m-cyclam-homocyclen)][MnCl4]2•12H2O | AW047 | 1288.441 | 5.380 | 0.07 | 4.176E−06 |
| [Co2(m-cyclam-homocyclen)(OAc)2][PF6]2 | AW049 | 1094.768 | 5.600 | 0.05 | 5.115E−06 |
| [Ni2(m-cyclam-homocyclen)(OAc)2][PF6]2•H2O | AW050 | 1112.303 | 8.540 | 0.04 | 7.678E−06 |
| [Zn2(m-cyclam-homocyclen)(OAc)2][PF6]2 | AW052B | 1107.692 | 6.580 | 0.05 | 5.940E−06 |
| p-H2PBCyclams | SLK10 | 582.911 | 1.410 | 0.11 | 2.419E−06 |
| Bn2PBCyclen | AW009 | 392.581 | 2.010 | 0.05 | 5.120E−06 |
| [Fe(Bn2PBCyclen)(C2H3O2)]PF6•1.2NH4PF6 | AW037 | 848.038 | 4.940 | 0.05 | 5.825E−06 |
| [Co(Bn2PBCyclen)(C2H3O2)]PF6 | AW038 | 655.523 | 5.080 | 0.04 | 7.750E−06 |
| [Ni(Bn2PBCyclen)(C2H3O2)]PF6 | AW039 | 655.283 | 4.73 | 0.04 | 7.218E−06 |
| [Ni2(m-CB-Homocyclens)(OAc)1.91[PF6]2.1 | CDG038 | 1088.853 | 9.58 | 0.03 | 8.798E−06 |
| [Zn2(m-CB-Cyclams)(OAc)2][PF6]2 | RM51 | 1121.697 | 6.17 | 0.05 | 5.501E−06 |
| [Ni2(m-CB-Cyclams)(OAc)2][PF6]2 | CDG009 | 1108.315 | 6.27 | 0.05 | 5.657E−06 |
| [Co2(p-CB-cyclam-cyclen)(OAc)2][PF6]2 | CMB027 | 1080.750 | 7.36 | 0.04 | 6.810E−06 |
| [Zn2(p-CB-cyclam-cyclen)(OAc)][PF6]3•4H2O | CMB030 | 1251.624 | 7.86 | 0.04 | 6.280E−06 |

TABLE 8

The in vitro Inhibitory Activity of the Macrocyclic Compounds Against MRSA

| Sample Code | Sample Code | Molecular Weight | MRSa IC$_{50}$ (μg/mL) | X more potent than ciprofloxacen | MRSA IC$_{50}$ (mol/L) |
|---|---|---|---|---|---|
| Ciprofloxacen | CIPRO | 331.346 | 0.070 | 1.00 | 2.113E−07 |
| m-CB-cyclams HCl salt | TJS04 | 973.692 | 7.050 | 0.03 | 7.240E−06 |
| m-SB-cyclens HCl salt | OB25B | 926.161 | 5.450 | 0.04 | 5.885E−06 |
| Mn2(p-CB-cyclams)Cl4 | JGL16A | 834.608 | 7.770 | 0.02 | 9.310E−06 |
| Mn(Bn2Bcyclam)Cl2 | NS06 | 532.458 | 1.510 | 0.07 | 2.836E−06 |
| Bn2Bcyclen | ANC14 | 378.564 | 8.570 | 0.01 | 2.264E−05 |
| Mn(Bn2Bcyclen)Cl2 | NS29 | 504.405 | 5.750 | 0.02 | 1.140E−05 |
| p-CB-H2Bcyclens | JGL19 | 498.764 | 1.060 | 0.10 | 2.125E−06 |
| Bn2PBCyclam | SLK09 | 420.645 | 4.960 | 0.02 | 1.179E−05 |
| [Mn(Bn2PBCyclam)][MnCl4] | BME08 | 672.321 | 0.800 | 0.18 | 1.190E−06 |
| [Cu(Bn2PBCyclam)(OAc)]PF6•2.5 H2O | BME10B | 733.227 | 5.350 | 0.03 | 7.297E−06 |
| [Co(Bn2PBCyclam)(OAc)]PF6 | DJD21 | 683.587 | 3.710 | 0.04 | 5.427E−06 |
| [Ni(Bn2PBCyclam)(OAc)]PF6 | DJD22 | 683.344 | 4.620 | 0.03 | 6.761E−06 |
| [Zn(Bn2PBCyclam)(OAc)]PF6 | DJD23 | 690.044 | 3.210 | 0.05 | 4.652E−06 |
| [Mn2(m-cyclam-homocyclen)][MnCl4]2•12H2O | AW047 | 1288.441 | 7.850 | 0.03 | 6.093E−06 |
| [Ni2(m-cyclam-homocyclen)(OAc)2][PF6]2•H2O | AW050 | 1112.303 | 4.650 | 0.05 | 4.181E−06 |
| p-H2PBCyclams | SLK10 | 582.911 | 2.500 | 0.05 | 4.289E−06 |
| Bn2PBCyclen | AW009 | 392.581 | 1.050 | 0.08 | 2.675E−06 |
| [Fe(Bn2PBCyclen)(C2H3O2)]PF6•1.2NH4PF6 | AW037 | 848.038 | 9.480 | 0.02 | 1.118E−05 |
| [Ni2(m-CB-Homocyclens)(OAc)1.9][PF6]2.1 | CDG038 | 1088.853 | 9.080 | 0.03 | 8.339E−06 |
| [Zn2(m-CB-Cyclams)(OAc)2][PF6]2 | RM51 | 1121.697 | 3.190 | 0.07 | 2.844E−06 |
| [Ni2(m-CB-Cyclams)(OAc)2][PF6]2 | CDG009 | 1108.315 | 5.410 | 0.04 | 4.881E−06 |
| [Co2(p-CB-cyclam-cyclen)(OAc)2][PF6]2 | CMB027 | 1080.750 | 5.390 | 0.04 | 4.987E−06 |
| [Zn2(p-CB-cyclam-cyclen)(OAc)][PF6]2•4H2O | CMB030 | 1251.624 | 8.760 | 0.03 | 6.999E−06 |

TABLE 9

Compounds evaluated against NTS *S. mansoni* at 33 μM

| S. No. | Compound ID | Effect at 72 h (%) |
|---|---|---|
| 1 | RM03 | 0.00% |
| 2 | MJG04 | 0.00% |
| 3 | AN06 | 5.41% |
| 4 | SH6 | 18.02% |
| 5 | ANC21 | 5.41% |
| 6 | ANC20A | 18.02% |
| 7 | DGJ061 | 30.63% |
| 8 | MBA04 | 24.32% |
| 9 | CNV06 | 0.00% |
| 10 | MM06 | 18.02% |
| 11 | NS6 | 11.71% |
| 12 | DJD50 | 18.02% |
| 13 | MM05 | 18.02% |
| 14 | JGL45 | 81.08% |
| 15 | NS06 | 81.08% |
| 16 | NS08 | 18.02% |
| 17 | TC11 | 24.32% |
| 18 | TC09 | 43.24% |
| 19 | RM37 | 100.00% |
| 20 | RM41 | 100.00% |
| 21 | AW056 | 5.41% |
| 22 | ANC14 | 43.24% |
| 23 | NS29 | 43.24% |
| 24 | NS30 | 24.32% |
| 25 | TC12 | 43.24% |
| 26 | TC10 | 30.63% |
| 27 | RM58 | 5.41% |
| 28 | RM42 | 30.63% |
| 29 | NS11 | 5.41% |
| 30 | NS12 | 100.00% |
| 31 | TRH016 | 11.71% |
| 32 | TRH11B | 24.32% |
| 33 | RM56A | 18.02% |
| 34 | RM55A | 30.63% |
| 35 | KS13 | 30.63% |
| 36 | KS15 | 11.71% |
| 37 | JGL08 | 11.71% |
| 38 | JGL16A | 5.41% |
| 39 | JGL17A | 100.00% |
| 40 | KS35 | 30.63% |
| 41 | KS33 | 0.00% |
| 42 | TJH384A | 5.41% |
| 43 | RM53 | 0.00% |
| 44 | KBN003 | 36.94% |
| 45 | KS41 | 5.41% |
| 46 | TJS04 | 24.32% |
| 47 | CDG009 | 0.00% |
| 48 | CDG010 | 11.71% |
| 49 | RM51 | 0.00% |
| 50 | RM52 | 5.41% |
| 51 | RM17 | 43.24% |
| 52 | OBO24B | 11.71% |
| 53 | OB28 | 0.00% |
| 54 | OB29 | 5.41% |
| 55 | OB30 | 5.41% |
| 56 | OB31 | 11.71% |
| 57 | DJC03 | 36.94% |
| 58 | DJC04 | 30.63% |
| 59 | DJC05C | 5.41% |
| 60 | DJC06A | 5.41% |
| 61 | DJC07 | 0.00% |
| 62 | MBA28A | 18.02% |
| 63 | MBA29A | 11.71% |
| 64 | KS22B | 5.41% |
| 65 | KS24 | 18.02% |
| 66 | KS25 | 18.02% |
| 67 | KS26 | 11.71% |
| 68 | KS27 | 100.00% |
| 69 | BNS009 | 24.32% |
| 70 | BNS017 | 0.00% |
| 71 | BNS19 | 18.02% |
| 72 | BNS20 | 18.02% |
| 73 | BNS21 | 5.41% |
| 74 | BNS22 | 11.71% |
| 75 | CDG029 | 24.32% |
| 76 | CDG021 | 11.71% |
| 77 | CDG022 | 11.71% |
| 78 | CDG023 | 18.02% |
| 79 | CDG030 | 18.02% |
| 80 | CDG015 | 5.41% |

TABLE 9-continued

Compounds evaluated against NTS S. mansoni at 33 μM

| S. No. | Compound ID | Effect at 72 h (%) |
|---|---|---|
| 81 | BNS018 | 11.71% |
| 82 | BNS023 | 5.41% |
| 83 | BNS024 | 5.41% |
| 84 | BNS025 | 18.02% |
| 85 | BNS026 | 0.00% |
| 86 | CDG019 | 0.00% |
| 87 | CDG024 | 5.41% |
| 88 | CDG025 | 18.02% |
| 89 | CDG026 | 11.71% |
| 90 | CDG027 | 11.71% |
| 91 | K-PAA2-0002-P3 | 100.00% |
| 92 | K-PAA2-0015-P40 | 100.00% |
| 93 | K-PAA2-0029-P68 | 43.24% |
| 94 | K-PAA2-0024-P48 | 43.24% |
| 95 | K-AVR-0005-P10-D1 | 100.00% |
| 96 | K-PSS-pentadecane | 93.69% |
| 97 | K-PSS-0001 | 62.16% |
| 98 | K-PAA2-0015-P30 | 100.00% |

TABLE 10

Compounds evaluated against NTS S. mansoni at 10 μM

| S. No | Compound ID | Effect at 72 h (%) |
|---|---|---|
| 14 | JGL45 | 44.83% |
| 15 | NS08 | 51.72 |
| 19 | RM37 | 24.14% |
| 20 | RM41 | 17.24% |
| 30 | NS12 | 100.00 |
| 39 | JGL17A | 100.00 |
| 68 | KS27 | 0.00% |
| 91 | K-PAA2-0002-P3 | 100.00 |
| 92 | K-PAA2-0015-P40 | 100.00 |
| 95 | K-AVR-0005-P10-D1 | 31.03% |
| 96 | K-PSS-pentadecane | 58.62 |
| 97 | K-PSS-0001 | 37.93% |
| 98 | K-PAA2-0015-P30 | 100.00 |

TABLE 11

$IC_{50}$ values of compounds on NTS 72 hours post-incubations

| S. No | Compound ID | $IC_{50}$ [μM] | r-value |
|---|---|---|---|
| 30 | NS12 | 6.69 | 0.81 |
| 39 | JGL17A | 9.65 | 0.95 |
| 91 | K-PAA2-0002-P3 | 1.40 | 0.84 |
| 92 | K-PAA2-0015-P40 | 0.87 | 0.91 |
| 98 | K-PAA2-0015-P30 | 0.83 | 0.83 |
| | Praziquantel | 2.2 | 0.9 |

TABLE 12

Compounds evaluated against adult S. mansoni at 10 μM

| S. No | Compound ID | Effect at 72 h (%) |
|---|---|---|
| 30 | NS12 | 2.08 |
| 39 | JGL17A | 8.33 |
| 91 | K-PAA2-0002-P3 | 87.50 |
| 92 | K-PAA2-0015-P40 | 100.0 |
| 98 | K-PAA2-0015-P30 | 100.0 |

TABLE 13

$IC_{50}$ values of compounds 72 hours post-exposure from adult worm screen

| S. No. | Compound ID | $IC_{50}$ [μM] | r-value |
|---|---|---|---|
| 91 | K-PAA2-0002-P3 | 4.12 | 0.91 |
| 92 | K-PAA2-0015-P40 | 1.34 | 0.87 |
| 98 | K-PAA2-0015-P30 | 1.62 | 0.87 |
| | Praziquantel | 0.1 | 0.90 |

TABLE 14

Comparison of activity of compounds 72 hours post-exposure against NTS and adult worms

| S. No. | Compound ID | $IC_{50}$ [μM] NTS | $IC_{50}$ [μM] Adults |
|---|---|---|---|
| 91 | K-PAA2-0002-P3 | 1.40 | 4.12 |
| 92 | K-PAA2-0015-P40 | 0.87 | 1.34 |
| 98 | K-PAA2-0015-P30 | 0.83 | 1.62 |

The invention claimed is:

1. A composition containing at least one macrocyclic ligand, the composition comprising a compound of Formula

(III)

wherein each "A" is a macrocyclic ligand that is independently selected from the group consisting of Formulas (a)-(e), with the proviso that at least one "A" must come from Formulas (a)-(d):

(a) a tetradentate ethylene cross-bridged macropolycyclic rigid ligand with ring size 12-14 and having the structure:

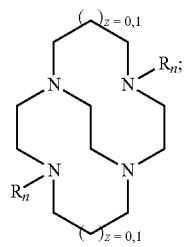

(b) a tetradentate ethylene side-bridged macropolycyclic rigid ligand with ring size 12-15 and having the structure:

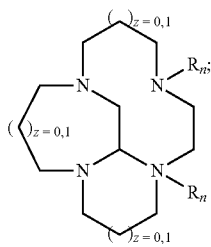

(c) a tetradentate propylene cross-bridged macropolycyclic rigid ligand with ring size 12-14 and having the structure:

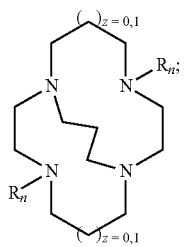

(d) a pentadentate ethylene cross-bridged macropolycyclic rigid ligand having the structure:

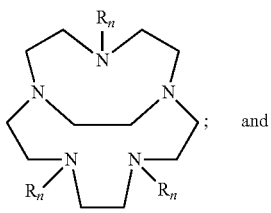

(e) a tetradentate or pentadentate-macrocyclic ligand having the structure:

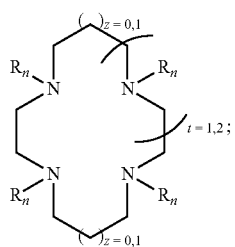

wherein, in Formulas (a)-(e):
  each "R" is independently selected from the group consisting of H, alkyl, heteroalkyl, aryl, heteroaryl, alkylaryl, and heteroalkylaryl groups;
  each "n" is an integer independently selected from 0, 1, and 2, completing the valence of the atoms to which the "R" moieties are covalently bonded;
  each "z" is an integer independently selected from 0 and 1; and
  each "t" is an integer independently selected from 1 and 2; and and wherein "Q" in Formula (III) is a linking mesityl group.

2. The composition of claim 1, further comprising a metal with which the compound is complexed, wherein the metal is selected from the group consisting of a transition metal, a main group metal, a lanthanide, an actinide, and mixtures thereof.

3. The composition of claim 2, wherein the transition metal is selected from the group consisting of cobalt, copper, iron, manganese, nickel, zinc, and mixtures thereof.

4. The composition of claim 2, wherein in Formulas (a)-(e), each nitrogen atom coordinates to a metal ion.

5. The composition of claim 1, wherein "Q" in Formula (III) is a 1,3,5-mesityl linker.

6. The composition of claim 1, wherein in Formulas (a)-(e), at least one "R" is a benzyl group.

7. The composition of claim 1, further defined as having anti-microbial activity.

8. The composition of claim 7, wherein the anti-microbial activity is further defined as an anti-fungal activity.

9. The composition of claim 8, wherein the composition has anti-fungal activity against at least one of *Cryptococcus neoformans*, *Cryptococcus laurentii*, *Cryptococcus albidus*, *Candida albicans*, *Candida glabrata*, *Candida krusei*, and *Aspergillus fumigatus*.

10. The composition of claim 7, wherein the anti-microbial activity is further defined as an anti-bacterial activity.

11. The composition of claim 10, wherein the anti-bacterial activity is effective against at least one of *Staphylococcus aureus*, Methicillin-resistant *Staphylococcus aureus* (MRSA), *Escherichia coli*, *Pseudomonas aeruginosa*, and *Mycobacterium intracellulare*.

12. The composition of claim 7, wherein the anti-microbial activity is further defined as an anti-parasitic activity.

13. The composition of claim 12, wherein the anti-parasitic activity is effective against at least one of *Leishmania donovani*, *Leishmania major*, *Leishmania tropica*, *Leishmania braziliensis*, *Leishmania Mexicana*, *Plasmodium falciparum*, and *Schistosoma mansoni*.

14. The composition of claim 1, further comprising an imaging agent attached thereto.

15. The composition of claim 14, wherein the imaging agent comprises a fluorophore.

16. The composition of claim 14, wherein the imaging agent comprises a radioisotope.

17. A pharmaceutical composition, comprising:
  at least one composition of claim 1; and
  a pharmaceutically acceptable carrier.

18. A method of inhibiting the growth and/or activity of at least one microbe, the method comprising the step of:
  contacting the microbe with the composition of claim 1, wherein the microbe is at least one of a bacteria, a fungus, or a parasite, and wherein:
  when the microbe is a bacteria, the bacteria is at least one of *Staphylococcus aureus*, Methicillin-resistant *Staphylococcus aureus* (MRSA), *Escherichia coli*, *Pseudomonas aeruginosa*, and *Mycobacterium intracellulare*;
  when the microbe is a fungus, the fungus is at least one of *Cryptococcus neoformans*, *Cryptococcus laurentii*, *Cryptococcus albidus*, *Candida albicans*, *Candida glabrata*, *Candida krusei*, and *Aspergillus fumigatus*; and
  when the microbe is a parasite, the parasite is at least one of *Leishmania donovani*, *Leishmania major*, *Leishmania tropica*, *Leishmania braziliensis*, *Leishmania Mexicana*, *Plasmodium falciparum*, and *Schistosoma mansoni*.

19. A method of treating, reducing the occurrence of, and/or reducing the severity of an infection in a subject, the method comprising the step of:
   administering an effective amount of the pharmaceutical composition of claim 17 to the subject; and
   wherein the infection is caused by at least one of a bacteria, a fungus, or a parasite, and wherein:
      when the infection is caused by a bacteria, the bacteria is at least one of *Staphylococcus aureus*, Methicillin-resistant *Staphylococcus aureus* (MRSA), *Escherichia coli, Pseudomonas aeruginosa*, and *Mycobacterium intracellulare;*
      when the infection is caused by a fungus, the fungus is at least one of *Cryptococcus neoformans, Cryptococcus laurentii, Cryptococcus albidus, Candida albicans, Candida glabrata, Candida krusei*, and *Aspergillus fumigatus*; and
         when the infection is caused by a parasite, the parasite is at least one of *Leishmania donovani, Leishmania major, Leishmania tropica, Leishmania braziliensis, Leishmania Mexicana, Plasmodium falciparum*, and *Schistosoma mansoni*.

20. The method of claim 19, wherein the infection is further defined as an opportunistic infection.

21. The method of claim 19, wherein the infection is a fungal infection caused by at least one of *Cryptococcus neoformans, Cryptococcus laurentii, Cryptococcus albidus, Candida albicans, Candida glabrata, Candida krusei*, and *Aspergillus fumigatus*.

22. The method of claim 19, wherein the infection is a bacterial infection caused by at least one of *Staphylococcus aureus*, Methicillin-resistant *Staphylococcus aureus* (MRSA), *Escherichia coli, Pseudomonas aeruginosa*, and *Mycobacterium intracellulare*.

23. The method of claim 19, wherein the infection is a parasitic infection caused by at least one of *Leishmania donovani, Leishmania major, Leishmania tropica, Leishmania braziliensis, Leishmania Mexicana, Plasmodium falciparum*, and *Schistosoma mansoni*.

24. A method of screening for the presence of an infection in a subject, the method comprising the steps of:
   contacting the subject with an effective amount of the composition of claim 14 and allowing the composition to bind to infection present in the subject;
   exposing at least a portion of the subject to an imaging device for cellular and/or tissue imaging of at least a portion of the subject to detect the presence of the imaging agent within the subject; and
   determining that the patient is infected if the imaging agent is detected; and
   wherein the infection is caused by at least one of a bacteria, a fungus, or a parasite, and wherein:
      when the infection is caused by a bacteria, the bacteria is at least one of *Staphylococcus aureus*, Methicillin-resistant *Staphylococcus aureus* (MRSA), *Escherichia coli, Pseudomonas aeruginosa*, and *Mycobacterium intracellulare;*
      when the infection is caused by a fungus, the fungus is at least one of *Cryptococcus neoformans, Cryptococcus laurentii, Cryptococcus albidus, Candida albicans, Candida glabrata, Candida krusei*, and *Aspergillus fumigatus*; and
      when the infection is caused by a parasite, the parasite is at least one of *Leishmania donovani, Leishmania major, Leishmania tropica, Leishmania braziliensis, Leishmania Mexicana, Plasmodium falciparum*, and *Schistosoma mansoni*.

\* \* \* \* \*

UNITED STATES PATENT AND TRADEMARK OFFICE
CERTIFICATE OF CORRECTION

PATENT NO. : 10,927,108 B2
APPLICATION NO. : 15/753409
DATED : February 23, 2021
INVENTOR(S) : Timothy J. Hubin et al.

It is certified that error appears in the above-identified patent and that said Letters Patent is hereby corrected as shown below:

In the Specification
Column 20, Line 6: Before "*1,1'-[1,4-phenylenebis(methylene)]-bis(1,5,9,12 Tetraazabicyclo[3.6.9.11] heptadecane)*" insert the following:

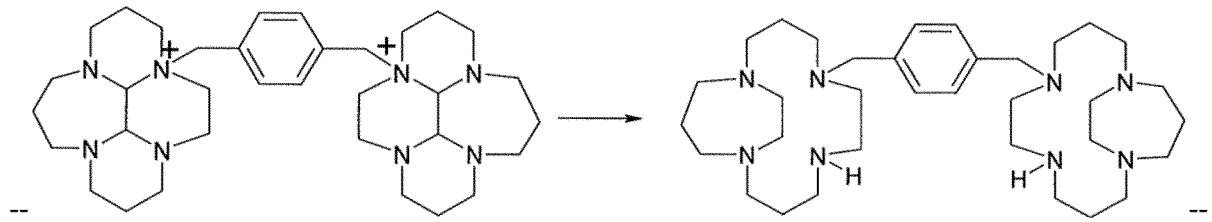

Column 25, Line 66: After "volume of" delete "2004" and replace with -- 200 µL --

Signed and Sealed this
Twenty-fifth Day of May, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,927,108 B2

From the bottom of Column 27 thru 32, replace the current Table 2, with:

TABLE 2: The *in vitro* Inhibitory Activity of the Macrocyclic Compounds Against *C. neoformans*

| Sample Code | Sample Code | Molecular Weight | *C. neoformans* IC$_{50}$ (µg/mL) | X more potent than Amphotericin B | *C. neoformans* IC$_{50}$ (mol/L) |
|---|---|---|---|---|---|
| Amphotericin B | AMB | 924.079 | 0.220 | 1.00 | 2.381E-07 |
| p-CB-cyclens HCl salt | OB15B | 872.115 | 0.610 | 0.34 | 6.994E-07 |
| m-CB-homocyclens HCl salt | OB65B | 990.676 | 0.160 | 1.47 | 1.615E-07 |
| m-CB-cyclens HCl salt | DJC05C | 890.561 | 0.940 | 0.23 | 1.056E-06 |
| p-CB-homocyclens HCl salt | TA22C | 928.223 | 0.310 | 0.71 | 3.340E-07 |
| p-CB-cyclams | KS23 | 582.926 | 8.200 | 0.02 | 1.407E-05 |
| m-CB-cyclams HCl salt | TJS04 | 973.692 | 0.380 | 0.61 | 3.903E-07 |
| m-SB-cyclams HCl salt | KS22B | 918.615 | 0.070 | 3.13 | 7.620E-08 |
| p-SB-cyclens HCl salt | OB24B | 863.104 | 0.670 | 0.31 | 7.763E-07 |
| m-SB-cyclens HCl salt | OB25B | 926.161 | 0.300 | 0.74 | 3.239E-07 |
| p-SB-homocyclens HCl salt | OB45B | 818.500 | 0.290 | 0.67 | 3.543E-07 |
| m-SB-homocyclens HCl salt | OB46B | 881.5 | 0.280 | 0.75 | 3.176E-07 |
| tris-SB-cyclams | CDG19 | 793.242 | 0.180 | 1.05 | 2.269E-07 |
| tris-SB-cyclens | CDG29 | 709.081 | 0.100 | 1.69 | 1.410E-07 |
| tris-CB-cyclens | BNS017 | 751.162 | 0.070 | 2.56 | 9.319E-08 |
| tris-CB-cyclams | BNS018 | 835.323 | 0.090 | 2.21 | 1.077E-07 |
| (dcp)1-SB-cyclen | OB99 | 358.314 | 0.310 | 0.28 | 8.652E-07 |
| [Cu(dcp1-SB-cyclen)(OAc)]PF6 | OB105 | 707.370 | 2.190 | 0.08 | 3.096E-06 |
| [Ni(dcp1-SB-cyclen)(OAc)]PF6 | OB106 | 621.013 | 0.390 | 0.38 | 6.280E-07 |
| [Zn(dcp1-SB-cyclen)(OAc)]PF6 | OB110A | 758.105 | 0.610 | 0.30 | 8.046E-07 |
| [Co(Me1dcp1-CB-cyclen)(OAc)]PF6 | OB118 | 635.283 | 6.050 | 0.03 | 9.523E-06 |
| [Cu2(p-CB-cyclams)(OAc)2](PF6)2 | TJH384A | 1118.030 | 0.700 | 0.38 | 6.261E-07 |
| [Zn2(p-CB-cyclams)(OAc)2](PF6)2 | KS34 | 1121.697 | 0.650 | 0.41 | 5.795E-07 |
| [Ni2(p-CB-cyclams)(OAc)2](PF6)2 | KS33 | 1108.317 | 1.020 | 0.26 | 9.203E-07 |
| [Co2(p-CB-cyclams)(OAc)2](PF6)2 | KS40 | 1108.804 | 0.020 | 13.21 | 1.804E-08 |
| Me1Pic1-CB-cyclen | KRW32 | 303.454 | 5.490 | 0.01 | 1.809E-05 |
| [Co(Me1Pic1-CB-cyclen)](PF6)3 | KRW48 | 838.329 | 1.090 | 0.18 | 1.300E-06 |
| [Zn(Me1Pic1-CB-cyclen)](PF6)2 | KRW49 | 694.79 | 5.230 | 0.03 | 7.527E-06 |
| p-CB-H2Bcyclams | JGL44 | 554.872 | 0.180 | 0.73 | 3.244E-07 |
| p-CB-H2Bcyclens | JGL19 | 498.764 | 0.590 | 0.20 | 1.183E-06 |
| p-dcp2-CB-cyclens | PW111A | 818.764 | 0.040 | 4.88 | 4.885E-08 |
| Fe-complex-4,10-bis(7-chloroquinoline)cyclen)Cl2 | K-PAA-0016-P36 | 885.67 | 0.940 | 0.22 | 1.061E-06 |
| [Mn2(H2-p-CB-cyclams)][MnCl4]2 | TJH412 | 1058.231 | 1.990 | 0.13 | 1.880E-06 |
| [Fe2(H2-p-CB-cyclams)][FeCl4]2 | TJH413B | 1061.859 | 7.380 | 0.03 | 6.950E-06 |
| [Co2(H2-p-CB-cyclams)(OAc)3](PF6)3 | TJH414B | 1284.749 | 0.234 | 1.31 | 1.821E-07 |
| [Ni2(H2-p-CB-cyclams)(OAc)2](PF6)2 | TJH415B | 1080.261 | 0.850 | 0.30 | 7.868E-07 |
| [Cu2(H2-p-CB-cyclams)(OAc)2](PF6)2 . 5H2O | TJH416B | 1180.042 | 3.030 | 0.09 | 2.568E-06 |
| [Zn2(H2-p-CB-cyclams)(OAc)2](PF6)2 . H2O | TJH417B | 1111.681 | 3.120 | 0.08 | 2.807E-06 |
| [Co(Me1Py1-CB-Cyclam)Cl]PF6 | DGJ012 | 570.849 | 4.730 | 0.03 | 8.286E-06 |
| [Co(B13N4)Cl2]PF6 | DGJ031 | 515.192 | 4.980 | 0.02 | 9.666E-06 |
| m-CB-cyclam-cyclen | DGJ036 | 554.856 | 5.800 | 0.02 | 1.045E-05 |
| Bn2PBCyclam | SLK09 | 420.645 | 0.910 | 0.11 | 2.163E-06 |
| [Mn(Bn2PBCyclam)][MnCl4] | BME08 | 672.321 | 1.203 | 0.13 | 1.789E-06 |
| [Fe(Bn2PBCyclam)][FeCl4] . H2O | BME09 | 692.15 | 1.070 | 0.15 | 1.546E-06 |
| [Cu(Bn2PBCyclam)(OAc)]PF6 . 2.5 H2O | BME10B | 733.227 | 13.810 | 0.01 | 1.883E-05 |
| Cu(Bn2PBCyclam)(OAc)2 | DJD20 | 602.281 | 3.130 | 0.05 | 5.197E-06 |
| [Co(Bn2PBCyclam)(OAc)]PF6 | DJD21 | 683.587 | 3.510 | 0.05 | 5.135E-06 |
| [Ni(Bn2PBCyclam)(OAc)]PF6 | DJD22 | 683.344 | 5.240 | 0.03 | 7.668E-06 |
| [Zn(Bn2PBCyclam)(OAc)]PF6 | DJD23 | 690.044 | 1.990 | 0.08 | 2.884E-06 |
| [p-(BMBCyclams)]Br2 | SLK17A | 712.568 | 8.250 | 0.02 | 1.158E-05 |
| [m-(BMBCyclams)]Br2 | DJD05 | 712.568 | 3.250 | 0.05 | 4.561E-06 |
| [Mn2(m-cyclam-homocyclen)][MnCl4]2 . 12H2O | AW047 | 1288.441 | 3.770 | 0.08 | 2.926E-06 |
| [Fe2(m-cyclam-homocyclen)][FeCl4]2 . 7H2O | AW048 | 1201.993 | 1.660 | 0.17 | 1.381E-06 |
| [Co2(m-cyclam-homocyclen)(OAc)2](PF6)2 | AW049 | 1094.768 | 0.156 | 1.67 | 1.425E-07 |

| Sample Code | Sample Code | Molecular Weight | C. neoformans IC$_{50}$ (μg/mL) | X more potent than Amphotericin B | C. neoformans IC$_{50}$ (mol/L) |
|---|---|---|---|---|---|
| [Ni2{m-cyclam-homocyclen}(OAc)2][PF6]2 . H2O | AW050 | 1112.303 | 1.040 | 0.25 | 9.350E-07 |
| [Cu2{m-cyclam-homocyclen}(OAc)1.5][PF6]2.5 | AW051A | 1146.953 | 1.172 | 0.23 | 1.022E-06 |
| [Zn2{m-cyclam-homocyclen}(OAc)2][PF6]2 | AW052B | 1107.692 | 1.150 | 0.23 | 1.038E-06 |
| p-H2PBCyclams | SLK10 | 582.911 | 15.010 | 0.01 | 2.575E-05 |
| Bn2Cyclam | BME04 | 380.571 | 12.160 | 0.01 | 3.195E-05 |
| [Ni(Bn2Cyclam)(OAc)]PF6 . H2O | BME06 | 661.287 | 17.990 | 0.01 | 2.720E-05 |
| [Co(Bn2Cyclam)(OAc)PF6 . H2O | BME07 | 661.215 | 6.980 | 0.02 | 1.056E-05 |
| Mn(Bn2Cyclam)Cl2 . H2O | TJH397A | 524.429 | 16.870 | 0.01 | 3.217E-05 |
| [Zn(Bn2Cyclam)(OAc)]PF6 | SLK07B | 649.974 | 19.840 | 0.01 | 3.052E-05 |
| H2PBCyclam | DJD27 | 240.389 | 1.830 | 0.03 | 7.613E-06 |
| Fe(H2PBCyclam)Cl3 . H2O | SLK36 | 420.607 | 3.330 | 0.03 | 7.917E-06 |
| Mn(H2PBCyclam)Cl3 . 3H2O | SLK37 | 455.730 | 1.780 | 0.06 | 3.906E-06 |
| [Co(H2PBCyclam)(OAc)]PF6 . NH4PF6 . H2O | SLK38B | 684.348 | 6.230 | 0.03 | 9.104E-06 |
| [Ni(H2PBCyclam)(OAc)]PF6 . 2NH4PF6 | SLK39B | 829.096 | 5.890 | 0.03 | 7.104E-06 |
| [Cu(H2PBCyclam)(OAc)]PF6 . 2NH4PF6 | SLK40B | 833.948 | 6.930 | 0.03 | 8.310E-06 |
| [Zn(H2PBCyclam)(OAc)]PF6 . 2.5NH4PF6 | SLK41 | 917.299 | 5.190 | 0.04 | 5.658E-06 |
| [Mn(Py-SB-Cyclam)Cl]PF6 . 3H2O | ADS17 | 606.874 | 5.220 | 0.03 | 8.601E-06 |
| [Fe(Py-SB-Cyclam)Cl]PF6 | ADS18C | 553.735 | 18.540 | 0.01 | 3.348E-05 |
| Ni(Py-SB-Cyclam)Cl2 . 3H2O | ADS20 | 501.117 | 18.590 | 0.01 | 3.710E-05 |
| Bn2PBCyclen | AW009 | 392.581 | 6.740 | 0.01 | 1.717E-05 |
| [Mn(Bn2PBCyclen)(C2H3O2)]PF6 . 2NH4PF6 | AW036 | 977.533 | 7.070 | 0.03 | 7.232E-06 |
| [Fe(Bn2PBCyclen)(C2H3O2)]PF6 . 1.2NH4PF6 | AW037 | 848.038 | 8.400 | 0.02 | 9.905E-06 |
| [Co(Bn2PBCyclen)(C2H3O2)]PF6 | AW038 | 655.523 | 4.370 | 0.04 | 6.666E-06 |
| [Ni(Bn2PBCyclen)(C2H3O2)]PF6 | AW039 | 655.283 | 7.640 | 0.02 | 1.166E-05 |
| [Cu(Bn2PBCyclen)(C2H3O2)0.4][PF6]1.6 | AW040 | 711.687 | 7.050 | 0.02 | 9.906E-06 |
| [Zn(Bn2PBCyclen)(C2H3O2)]PF6 | AW041 | 661.985 | 7.330 | 0.02 | 1.107E-05 |
| [Cu2(p-CB-Cyclens)(OAc)2][PF6]2 | JAV06 | 1061.922 | 10.900 | 0.02 | 1.026E-05 |
| [Cu2(m-CB-Cyclens)(OAc)2][PF6]2 | DJC06A | 1061.922 | 6.710 | 0.04 | 6.319E-06 |
| [Zn2(m-CB-Cyclens)(OAc)2][PF6]2 | DJC07 | 1065.590 | 7.410 | 0.03 | 6.954E-06 |
| [Cu2(p-CB-Homocyclens)(OAc)2][PF6]2 | ANC011 | 1089.274 | 4.190 | 0.06 | 3.847E-06 |
| [Ni2(p-CB-Homocyclens)(OAc)2][PF6]2 | TJH378A | 1080.264 | 7.540 | 0.03 | 6.980E-06 |
| [Co2(p-CB-Homocyclens)(OAc)2][PF6]2 | TJH379A | 1080.750 | 0.800 | 0.32 | 7.402E-07 |
| [Cu2(m-CB-Homocyclens)(OAc)2.5][PF6]1.5 | CDG035 | 1047.006 | 3.260 | 0.08 | 3.114E-06 |
| [Co2(m-CB-Homocyclens)(OAc)2.6][PF6]1.4 | CDG036 | 1029.189 | 3.040 | 0.08 | 2.954E-06 |
| [Zn2(m-CB-Homocyclens)(OAc)0.5][PF6]3.5 | CDG037 | 1222.546 | 1.620 | 0.18 | 1.325E-06 |
| [Ni2(m-CB-Homocyclens)(OAc)1.9][PF6]2.1 | CDG038 | 1088.853 | 3.010 | 0.09 | 2.764E-06 |
| [Cu2(m-CB-Cyclams)(OAc)2][PF6]2 | RM52 | 1118.029 | 0.820 | 0.32 | 7.334E-07 |
| [Zn2(m-CB-Cyclams)(OAc)2][PF6]2 | RM51 | 1121.697 | 1.850 | 0.14 | 1.649E-06 |
| [Ni2(m-CB-Cyclams)(OAc)2][PF6]2 | CDG009 | 1108.315 | 3.530 | 0.07 | 3.185E-06 |
| [Co2(m-CB-Cyclams)(OAc)2][PF6]4 | CDG010 | 1398.723 | 0.960 | 0.35 | 6.863E-07 |
| [Cu2(m-SB-Cyclams)(OAc)2][PF6]2 | KS24 | 1030.922 | 3.180 | 0.08 | 3.085E-06 |
| [Ni2(m-SB-Cyclams)(OAc)2][PF6]2 | KS25 | 1021.217 | 16.030 | 0.02 | 1.570E-05 |
| [Zn2(m-SB-Cyclams)(OAc)2][PF6]2 | KS26 | 1034.622 | 12.510 | 0.02 | 1.209E-05 |
| [Cu2(p-SB-Cyclens)(OAc)2][PF6]2 | OB28 | 1033.868 | 5.210 | 0.05 | 5.039E-06 |
| [Ni2(p-SB-Cyclens)(OAc)2][PF6]2 . H2O | OB29 | 1042.171 | 0.800 | 0.31 | 7.676E-07 |
| [Co2(p-SB-Cyclens)(OAc)2][PF6]2 . DMF | OB30 | 1097.737 | 0.800 | 0.33 | 7.288E-07 |
| [Cu2(m-SB-Cyclens)(OAc)2][PF6]2 . 2 H2O | OB34 | 1069.899 | 0.800 | 0.32 | 7.477E-07 |
| [Ni2(m-SB-Cyclens)(OAc)2][PF6]2 . H2O | OB35 | 1042.171 | 0.800 | 0.31 | 7.676E-07 |
| [Co2(m-SB-Cyclens)(OAc)2][PF6]2 . 2H2O | OB36 | 1060.673 | 0.800 | 0.32 | 7.542E-07 |
| [Zn2(m-SB-Cyclens)(OAc)2][PF6]2 . 2H2O | OB37 | 1073.567 | 0.800 | 0.32 | 7.452E-07 |
| p-SB-Homocyclens | OB45 | 526.805 | 0.800 | 0.16 | 1.519E-06 |
| [Cu2(p-SB-Homocyclens)][PF6]4 . 2H2O | OB49 | 1269.783 | 0.800 | 0.38 | 6.300E-07 |
| m-SB-Homocyclens | OB46 | 526.805 | 4.850 | 0.03 | 9.206E-06 |
| [Co2(m-SB-Homocyclens)(OAc)2][PF6]2 . H2O | OB55 | 1070.703 | 5.120 | 0.05 | 4.782E-06 |
| [Ni3(tris-SB-Cyclams)][PF6]6 | CDG024 | 1839.097 | 2.440 | 0.18 | 1.327E-06 |
| [Co3(tris-SB-Cyclams)(OAc)3][PF6]3 | CDG025 | 1582.068 | 1.800 | 0.21 | 1.138E-06 |

CERTIFICATE OF CORRECTION (continued)
U.S. Pat. No. 10,927,108 B2

| Sample Code | Sample Code | Molecular Weight | C. neoformans IC$_{50}$ (µg/mL) | X more potent than Amphotericin B | C. neoformans IC$_{50}$ (mol/L) |
|---|---|---|---|---|---|
| [Zn3{tris-SB-Cyclams}(OAc)3][PF6]3 . NH4PF6 | CDG026 | 1764.411 | 10.030 | 0.04 | 5.685E-06 |
| [Cu3{tris-SB-Cyclams}(OAc)3][PF6]3 . 1.5NH4PF6 | CDG027 | 1840.411 | 1.280 | 0.34 | 6.955E-07 |
| [Co3{tris-SB-Cyclens}(OAc)3][PF6]3 | CDG021 | 1497.907 | 0.800 | 0.45 | 5.341E-07 |
| [Cu3{tris-SB-Cyclens}(OAc)3][PF6]3 . 0.5NH4PF6 | CDG022 | 1593.247 | 5.480 | 0.07 | 3.440E-06 |
| [Zn3{tris-SB-Cyclens}(OAc)3][PF6]3 . 0.5NH4PF6 | CDG023 | 1598.749 | 1.310 | 0.29 | 8.194E-07 |
| [Ni3{tris-SB-Cyclens}OAc)3][PF6]3 . H2O | CDG030 | 1515.193 | 0.800 | 0.45 | 5.280E-07 |
| [Ni3{tris-CB-Cyclens}(OAc)3][PF6]3 . 2.5H2O | BNS23 | 1668.457 | 12.110 | 0.03 | 7.258E-06 |
| [Co3{tris-CB-Cyclams}(OAc)1.5][PF6]4.5 | BNS24 | 1753.028 | 0.800 | 0.52 | 4.564E-07 |
| [Cu3{tris-CB-Cyclams}(OAc)3][PF6]3 | BNS25 | 1637.987 | 1.950 | 0.20 | 1.190E-06 |
| [Zn3{tris-CB-Cyclams}(OAc)3][PF6]3 . 2.4NH4PF6 | BNS26 | 2034.696 | 6.840 | 0.07 | 3.362E-06 |
| [Co3{tris-CB-Cyclens}(OAc)3][PF6]6 | BNS20 | 1974.880 | 1.000 | 0.47 | 5.064E-07 |
| [Cu3{tris-CB-Cyclens}(OAc)3][PF6]3 | BNS21 | 1553.826 | 1.320 | 0.28 | 8.495E-07 |
| [Zn3{tris-CB-Cyclens}(OAc)3][PF6]3 . 6H2O | BNS22 | 1667.420 | 3.410 | 0.12 | 2.045E-06 |
| [Co(Bn1Me1Bcyclen)(OAc)][PF6]2 | TRH15 | 710.369 | 0.800 | 0.21 | 1.126E-06 |
| [Co(Bn1Me1Bcyclam)(OAc)]PF6 | TRH16 | 593.453 | 9.190 | 0.02 | 1.549E-05 |
| [Co2{m-SB-cyclam-cyclen}(OAc)2][PF6]4 . H2O | CMB032 | 1360.631 | 0.800 | 0.41 | 5.880E-07 |
| [Ni2{m-SB-cyclam-cyclen}(OAc)][PF6]3 | CMB033 | 1138.128 | 1.710 | 0.16 | 1.502E-06 |
| [Cu2{m-SB-cyclam-cyclen}(OAc)][PF6]3 . 2H2O | CMB034 | 1183.863 | 0.800 | 0.35 | 6.758E-07 |
| [Zn2{m-SB-cyclam-cyclen}(OAc)2][PF6]2 . 3.3H2O | CMB035 | 1125.063 | 0.800 | 0.33 | 7.111E-07 |
| [Co2{p-SB-cyclam-cyclen}(OAc)2][PF6]2 | CMB016A | 1052.696 | 1.570 | 0.16 | 1.491E-06 |
| [Ni2{p-SB-cyclam-cyclen}(OAc)][PF6]3 . H2O | CMB017A | 1156.145 | 4.940 | 0.06 | 4.273E-06 |
| [Cu2{p-SB-cyclam-cyclen}(OAc)1.2][PF6]2.8 | CMB018 | 1130.658 | 3.020 | 0.09 | 2.671E-06 |
| p-CB-cyclam-cyclen | CMB008D | 554.858 | 0.800 | 0.17 | 1.442E-06 |
| [Co2{p-CB-cyclam-cyclen}(OAc)2][PF6]2 | CMB027 | 1080.750 | 0.800 | 0.32 | 7.402E-07 |
| [Ni2{p-CB-cyclam-cyclen}(OAc)2][PF6]2 | CMB028 | 1080.264 | 1.330 | 0.19 | 1.231E-06 |
| [Cu2{p-CB-cyclam-cyclen}(OAc)2][PF6]2 | CMB029 | 1089.976 | 0.800 | 0.32 | 7.340E-07 |
| [Zn2{p-CB-cyclam-cyclen}(OAc)][PF6]3 . 4H2O | CMB030 | 1251.624 | 1.380 | 0.22 | 1.103E-06 |
| [Zn(Me1-SB-Cyclam)(C2H3O2)]PF6 | DLM32 | 509.793 | 17.280 | 0.01 | 3.390E-05 |

| Sample Code | Sample Code | Molecular Weight | C. neoformans IC$_{50}$ (µg/mL) | X more potent than Amphotericin B | C. neoformans IC$_{50}$ (mol/L) |
|---|---|---|---|---|---|
| [Co(H2Bcyclam)(OAc)]PF6 | ANC25 | 489.304 | 4.360 | 0.03 | 8.911E-06 |
| [Co(Bcyclam)Cl2]PF6 | SAH06#2 | 529.218 | 19.220 | 0.01 | 3.632E-05 |
| [Mn(Bcyclen)Cl2]PF6 | CNV06 | 497.170 | 6.390 | 0.02 | 1.285E-05 |
| [Co(Bcyclen)Cl2]PF6 | DT06#2 | 500.051 | 3.390 | 0.04 | 6.779E-06 |
| [Co(H2Bcyclen)(OAc)]PF6 | ANC27A | 461.251 | 5.030 | 0.02 | 1.091E-05 |
| SB-Bl-cyclen | SJA219 | 328.464 | 5.780 | 0.01 | 1.760E-05 |
| CB-Bl-cyclen | SJA220 | 342.491 | 5.160 | 0.02 | 1.507E-05 |
| [Zn(SB-Bl-cyclen)(Cl)2] | SJA222 | 328.464 | 2.610 | 0.03 | 7.946E-06 |
| [Zn(CB-Bl-cyclen)(OAc)2] | SJA225 | 342.491 | 5.690 | 0.01 | 1.661E-05 |
| [Mn(CB-Bl-cyclen)(Cl)2] | SJA227 | 342.491 | 1.930 | 0.04 | 5.635E-06 |
| SB-BINO2-cyclen | SJA229 | 463.586 | 1.890 | 0.06 | 4.077E-06 |
| CB-BINO2-cyclen | SJA230 | 477.613 | 7.930 | 0.01 | 1.660E-05 |
| [Ni(SB-BINO2-cyclen)(OAc)2] | SJA232 | 463.586 | 5.070 | 0.02 | 1.094E-05 |
| Bis-SB-C-Ar-NO2 | SJA233 | 689.980 | 0.550 | 0.30 | 7.971E-07 |
| [Cu2{bis-SB-C-Ar-NO2}(ClO4)4] | SJA234 | 1214.870 | 1.910 | 0.15 | 1.572E-06 |
| [Zn2{bis-SB-C-Ar-NO2}(OAc)4] | SJA235 | 1056.910 | 1.930 | 0.13 | 1.826E-06 |
| [Ni2{bis-SB-C-Ar-NO2}(NO3)4] | SJA236 | 1055.380 | 0.740 | 0.34 | 7.012E-07 |
| [Mn(Bcyclen)Cl2]PF6 | CNV06 | 497.170 | 5.579 | 0.02 | 1.122E-05 |
| [Mn(B13N4)Cl2]PF6 | DLM10 | 511.197 | 9.522 | 0.01 | 1.863E-05 |
| [Mn(plc1Me1-CB-Cyclen)Cl]Cl | KRW37 | 429.290 | 3.076 | 0.03 | 7.166E-06 |
| [Mn(Bn1Me1-CB-Cyclam)Cl2] | NS11 | 456.355 | 5.038 | 0.02 | 1.104E-05 |
| {[Mn(4,10-bis(7-chloroquinoline)cyclen)Cl2} | K-PAA2-0004-P8-TJH410 | 621.291 | 4.123 | 0.04 | 6.637E-06 |

Column 33 thru the top of 36, replace the current Table 3, with:

TABLE 3: The in vitro Inhibitory Activity of the Macrocyclic Compounds Against *L. donovani*

| Sample Code | Sample Code | Molecular Weight | *L. donovani* IC$_{50}$ (μg/mL) | X more potent than Pentamidine | *L. donavani* IC$_{50}$ (mol/L) |
|---|---|---|---|---|---|
| Pentamidine | PENT | 340.420 | 1.81 | 1.00 | 5.317E-06 |
| [Mn2(H2-p-CB-cyclams)][MnCl4]2 | TJH412 | 1058.231 | 33.37 | 0.17 | 3.153E-05 |
| [Zn2(H2-p-CB-cyclams)(OAc)2][PF6]2 . H2O | TJH417B | 1111.681 | 34.93 | 0.17 | 3.142E-05 |
| Bn2PBCyclam | SLK09 | 420.645 | 2.56 | 0.87 | 6.086E-06 |
| [Mn(Bn2PBCyclam)][MnCl4] | BME08 | 672.321 | 1.78 | 2.01 | 2.648E-06 |
| [Fe(Bn2PBCyclam)][FeCl4] . H2O | BME09 | 692.150 | 14.10 | 0.26 | 2.037E-05 |
| [Cu(Bn2PBCyclam)(OAc)]PF6 . 2.5 H2O | BME10B | 733.227 | 3.64 | 1.07 | 4.964E-06 |
| Cu(Bn2PBCyclam)(OAc)2 | DJD20 | 602.281 | 14.65 | 0.22 | 2.432E-05 |
| [Co(Bn2PBCyclam)(OAc)]PF6 | DJD21 | 683.587 | 14.12 | 0.26 | 2.066E-05 |
| [Ni(Bn2PBCyclam)(OAc)]PF6 | DJD22 | 683.344 | 13.10 | 0.28 | 1.917E-05 |
| [Zn(Bn2PBCyclam)(OAc)]PF6 | DJD23 | 690.044 | 4.32 | 0.85 | 6.260E-06 |
| [p-(BMBCyclams)]Br2 | SLK17A | 712.568 | 16.69 | 0.23 | 2.342E-05 |
| [p-(DCP-BMBCyclams)]Br4 | SLK26 | 1194.494 | 14.76 | 0.43 | 1.236E-05 |
| [m-(BMBCyclams)]Br2 | DJD05 | 712.568 | 18.18 | 0.21 | 2.551E-05 |
| [Co2(m-cyclam-homocyclen)(OAc)2][PF6]2 | AW049 | 1094.768 | 16.93 | 0.34 | 1.546E-05 |
| [Ni2(m-cyclam-homocyclen)(OAc)2][PF6]2 . H2O | AW050 | 1112.303 | 16.50 | 0.36 | 1.483E-05 |
| [Zn2(m-cyclam-homocyclen)(OAc)2][PF6]2 | AW052B | 1107.692 | 17.60 | 0.33 | 1.589E-05 |
| p-H2PBCyclams | SLK10 | 582.911 | 15.50 | 0.20 | 2.659E-05 |
| Bn2Cyclam | BME04 | 380.571 | 2.63 | 0.77 | 6.911E-06 |
| [Ni(Bn2Cyclam)(OAc)]PF6 . H2O | BME06 | 661.287 | 26.25 | 0.13 | 3.970E-05 |
| Mn(Bn2Cyclam)Cl2 . H2O | TJH397A | 524.429 | 2.31 | 1.21 | 4.405E-06 |
| Fe(Bn2Cyclam)Cl2 . 0.5 H2O | TJH398A | 516.328 | 2.28 | 1.20 | 4.416E-06 |
| [Zn(Bn2Cyclam)(OAc)]PF6 | SLK07B | 649.974 | 2.97 | 1.16 | 4.569E-06 |
| (DCP)2Cyclam | DJD29 | 520.336 | 9.76 | 0.28 | 1.876E-05 |
| Bn2PBCyclen | AW009 | 392.581 | 21.40 | 0.10 | 5.451E-05 |
| [Mn(Bn2PBCyclen)(C2H3O2)]PF6 . 2NH4PF6 | AW036 | 977.533 | 25.41 | 0.20 | 2.599E-05 |

| Sample Code | Sample Code | Molecular Weight | *L. donovani* IC$_{50}$ (μg/mL) | X more potent than Pentamidine | *L. donavani* IC$_{50}$ (mol/L) |
|---|---|---|---|---|---|
| [Fe(Bn2PBCyclen)(C2H3O2)]PF6 . 1.2NH4PF6 | AW037 | 848.038 | 26.63 | 0.17 | 3.140E-05 |
| [Co(Bn2PBCyclen)(C2H3O2)]PF6 | AW038 | 655.523 | 20.66 | 0.17 | 3.152E-05 |
| [Ni(Bn2PBCyclen)(C2H3O2)]PF6 | AW039 | 655.283 | 24.41 | 0.14 | 3.725E-05 |
| [Zn(Bn2PBCyclen)(C2H3O2)]PF6 | AW041 | 661.985 | 22.92 | 0.15 | 3.462E-05 |
| [Cu2(m-CB-Homocyclens)(OAc)2.5][PF6]1.5 | CDG035 | 1047.006 | 26.37 | 0.21 | 2.519E-05 |
| [Co2(m-CB-Homocyclens)(OAc)2.6][PF6]1.4 | CDG036 | 1029.189 | 22.23 | 0.25 | 2.160E-05 |
| [Ni2(m-CB-Homocyclens)(OAc)1.9][PF6]2.1 | CDG038 | 1088.853 | 19.92 | 0.29 | 1.829E-05 |
| [Zn2(m-CB-Cyclams)(OAc)2][PF6]2 | RM51 | 1121.697 | 19.82 | 0.30 | 1.767E-05 |
| p-SB-Homocyclens | OB45 | 526.805 | 17.44 | 0.16 | 3.311E-05 |
| [Ni3(tris-CB-Cyclams)(OAc)3][PF6]3 . 2.5H2O | BNS23 | 1668.457 | 31.63 | 0.28 | 1.896E-05 |
| [Cu(Bn1Me1Bcyclam)(OAc)]PF6 | RM56A | 598.072 | 33.32 | 0.10 | 5.571E-05 |
| [Ni(Bn1Me1Bcyclam)(OAc)]PF6 . 0.5NH4PF6 | TRH11B | 647.717 | 38.64 | 0.09 | 5.966E-05 |
| [Co2(p-SB-cyclam-cyclen)(OAc)2][PF6]2 | CMB016A | 1052.696 | 33.81 | 0.17 | 3.212E-05 |
| p-CB-cyclam-cyclen | CMB008D | 554.858 | 38.75 | 0.08 | 6.984E-05 |
| [Co2(p-CB-cyclam-cyclen)(OAc)2][PF6]2 | CMB027 | 1080.750 | 32.62 | 0.18 | 3.018E-05 |
| [Ni2(p-CB-cyclam-cyclen)(OAc)2][PF6]2 | CMB028 | 1080.264 | 30.69 | 0.19 | 2.841E-05 |
| [Zn2(p-CB-cyclam-cyclen)(OAc)][PF6]3 . 4H2O | CMB030 | 1251.624 | 31.32 | 0.21 | 2.502E-05 |
| p-CB-cyclens HCl salt | OB15B | 872.115 | 20.94 | 0.22 | 2.401E-05 |
| m-CB-homocyclens HCl salt | OB65B | 990.676 | 11.08 | 0.48 | 1.118E-05 |
| m-CB-cyclens HCl salt | DJC05C | 890.561 | 22.89 | 0.21 | 2.570E-05 |
| p-CB-homocyclens HCl salt | TA22C | 928.223 | 16.31 | 0.30 | 1.757E-05 |
| m-CB-cyclams HCl salt | TJS04 | 973.692 | 10.37 | 0.50 | 1.065E-05 |
| m-SB-cyclams HCl salt | KS22B | 918.615 | 17.61 | 0.28 | 1.917E-05 |
| p-SB-cyclens HCl salt | OB24B | 863.104 | 32.40 | 0.14 | 3.754E-05 |
| m-SB-cyclens HCl salt | OB25B | 926.161 | 11.45 | 0.43 | 1.236E-05 |
| p-SB-homocyclens HCl salt | OB45B | 818.500 | 34.55 | 0.13 | 4.221E-05 |
| m-SB-homocyclens HCl salt | OB46B | 818.500 | 34.26 | 0.13 | 4.186E-05 |
| tris-SB-cyclams | CDG19 | 793.242 | 15.91 | 0.27 | 2.006E-05 |

| Sample Code | Sample Code | Molecular Weight | L. donovani IC$_{50}$ (μg/mL) | X more potent than Pentamidine | L. donovani IC$_{50}$ (mol/L) |
|---|---|---|---|---|---|
| tris-SB-cyclens | CDG29 | 709.081 | 11.69 | 0.32 | 1.649E-05 |
| tris-CB-cyclens | BNS017 | 751.162 | 25.46 | 0.16 | 3.389E-05 |
| tris-CB-cyclams | BNS018 | 835.323 | 7.73 | 0.57 | 9.254E-06 |
| (dcp)1-SB-cyclen | OB99 | 358.314 | 20.87 | 0.09 | 5.825E-05 |
| [Ni(dcp1-SB-cyclen)(OAc)]PF6 | OB106 | 621.013 | 23.19 | 0.14 | 3.734E-05 |
| [Zn(dcp1-SB-cyclen)(OAc)]PF6 | OB110A | 758.105 | 38.32 | 0.11 | 5.055E-05 |
| [Zn2(p-CB-cyclams)(OAc)2](PF6)2 | KS34 | 1121.697 | 23.49 | 0.25 | 2.094E-05 |
| Bn2Bcyclam | JGL45 | 406.610 | 3.94 | 0.55 | 9.690E-06 |
| Mn(Bn2Bcyclam)Cl2 | NS06 | 532.458 | 21.99 | 0.13 | 4.130E-05 |
| Fe(Bn2Bcyclam)Cl2 | NS08 | 533.367 | 1.71 | 1.66 | 3.206E-06 |
| [Zn(Bn2Bcyclam)(OAc)]PF6 | RM41 | 676.003 | 9.51 | 0.38 | 1.407E-05 |
| [Cu(Bn2Bcyclam)(OAc)]PF6 | RM37 | 674.169 | 6.17 | 0.58 | 9.152E-06 |
| [Co(Bn2Bcyclam)(OAc)]PF6 | TC11 | 669.557 | 35.29 | 0.10 | 5.271E-05 |
| [Ni(Bn2Bcyclam)(OAc)]PF6 | TC09 | 669.313 | 6.51 | 0.55 | 9.726E-06 |
| Bn2Bcyclen | ANC14 | 378.564 | 3.80 | 0.53 | 1.004E-05 |
| Mn(Bn2Bcyclen)Cl2 | NS29 | 504.405 | 7.70 | 0.35 | 1.527E-05 |
| [Ni(Bn2Bcyclen)(OAc)]PF6 | TC10 | 641.260 | 10.95 | 0.31 | 1.708E-05 |
| [Zn(Bn2Bcyclen)(OAc)]PF6 | RM42 | 647.950 | 4.73 | 0.73 | 7.300E-06 |
| p-CB-H2Bcyclams | JGL44 | 554.872 | 28.08 | 0.11 | 5.061E-05 |
| p-CB-H2Bcyclens | JGL19 | 498.764 | 8.54 | 0.31 | 1.712E-05 |
| p-dcp2-CB-cyclens | PW111A | 818.764 | 12.89 | 0.34 | 1.574E-05 |
| Bis-SB-C-Ar-NO2 | SJA233 | 689.980 | 30.32 | 0.12 | 4.394E-05 |
| [Cu2(bis-SB-C-Ar-NO2)(ClO4)4] | SJA234 | 1214.870 | 30.31 | 0.21 | 2.495E-05 |
| [Zn2(bis-SB-C-Ar-NO2)(OAc)4] | SJA235 | 1056.910 | 34.77 | 0.16 | 3.290E-05 |
| [Ni2(bis-SB-C-Ar-NO2)(NO3)4] | SJA236 | 1055.380 | 24.85 | 0.23 | 2.355E-05 |

The middle of Column 35-36, replace the current Table 4, with:

TABLE 4: The *in vitro* Inhibitory Activity of the Macrocyclic Compounds Against *C. krusei*

| Sample Code | Sample Code | Molecular Weight | C. krusei IC$_{50}$ (μg/mL) | X more potent than amphotericin B | C. krusei IC$_{50}$ (mol/L) |
|---|---|---|---|---|---|
| Amphotericin B | AMB | 923.490 | 1.380 | 1.00 | 1.494E-06 |
| m-SB-cyclens HCl salt | OB25B | 926.161 | 6.530 | 0.21 | 7.051E-06 |
| m-SB-homocyclens HCl salt | OB46B | 818.500 | 7.420 | 0.16 | 9.065E-06 |
| tris-SB-cyclams | CDG19 | 793.242 | 4.790 | 0.25 | 6.039E-06 |
| tris-SB-cyclens | CDG29 | 709.081 | 4.660 | 0.23 | 6.572E-06 |
| tris-CB-cyclens | BNS017 | 751.162 | 5.850 | 0.19 | 7.788E-06 |
| (dcp)1-SB-cyclen | OB99 | 358.314 | 5.660 | 0.09 | 1.580E-05 |
| [Cu2(p-CB-cyclams)(OAc)2](PF6)2 | TJH384A | 1118.030 | 6.760 | 0.25 | 6.046E-06 |
| [Ni(Bn2Bcyclam)(OAc)]PF6 | TC09 | 669.313 | 4.520 | 0.22 | 6.753E-06 |
| CB-BiNO2-cyclen | SJA230 | 477.600 | 7.690 | 0.09 | 1.610E-05 |
| Bis-SB-C-Ar-NO2 | SJA233 | 689.980 | 4.070 | 0.25 | 5.899E-06 |
| [Cu2(bis-SB-C-Ar-NO2)(ClO4)4] | SJA234 | 1214.870 | 4.550 | 0.40 | 3.745E-06 |
| [Ni2(bis-SB-C-Ar-NO2)(NO3)4] | SJA236 | 1055.380 | 6.030 | 0.26 | 5.714E-06 |
| [Mn(Bn2PBCyclam)][MnCl4] | BME08 | 672.321 | 5.270 | 0.19 | 7.839E-06 |
| [Ni(Bn2PBCyclam)(OAc)]PF6 | DJD22 | 683.344 | 5.250 | 0.19 | 7.683E-06 |
| [p-(BMBCyclams)]Br2 | SLK17A | 712.568 | 0.880 | 1.21 | 1.235E-06 |
| [Co2(m-cyclam-homocyclen)(OAc)2](PF6)2 | AW049 | 1094.768 | 6.520 | 0.25 | 5.956E-06 |
| Bn2PBCyclen | AW009 | 392.581 | 6.170 | 0.10 | 1.572E-05 |
| [Mn(Bn2PBCyclen)(C2H3O2)]PF6 . 2NH4PF6 | AW036 | 977.533 | 4.990 | 0.29 | 5.105E-06 |
| [Ni(Bn2PBCyclen)(C2H3O2)]PF6 | AW039 | 655.283 | 5.610 | 0.17 | 8.561E-06 |
| [Zn(Bn2PBCyclen)(C2H3O2)]PF6 | AW041 | 661.985 | 5.170 | 0.19 | 7.810E-06 |
| [Cu2(m-SB-Cyclens)(OAc)2](PF6)2 . 2 H2O | OB34 | 1069.899 | 5.780 | 0.28 | 5.402E-06 |
| [Ni2(m-SB-Cyclens)(OAc)2](PF6)2 . H2O | OB35 | 1042.171 | 0.800 | 1.95 | 7.676E-07 |
| p-SB-Homocyclens | OB45 | 526.805 | 0.800 | 0.98 | 1.519E-06 |
| [Co3(tris-SB-Cyclens)(OAc)3](PF6)3 | CDG021 | 1497.907 | 4.200 | 0.53 | 2.804E-06 |
| [Zn3(tris-CB-Cyclams)(OAc)3](PF6)3 . 2.4NH4PF6 | BNS26 | 2034.696 | 1.220 | 2.49 | 5.996E-07 |
| [Co3(tris-CB-Cyclens)(OAc)3](PF6)6 | BNS20 | 1974.880 | 0.980 | 3.01 | 4.962E-07 |

The Bottom of Column 35-36 to 37-38, replace the current Table 5, with:

TABLE 5: The *in vitro* Inhibitory Activity of the Macrocyclic Compounds Against *C. glabrata*

| Sample Code | Sample Code | Molecular Weight | C. glabrata IC$_{50}$ (µg/mL) | X more potent than amphotericin B | C. glabrata IC$_{50}$ (mol/L) |
|---|---|---|---|---|---|
| Amphotericin B | AMB | 923.490 | 1.310 | 1.00 | 1.419E-06 |
| tris-SB-cyclams | CDG19 | 793.242 | 9.800 | 0.11 | 1.235E-05 |
| Mn2(p-CB-cyclams)Cl4 | JGL16A | 834.608 | 18.600 | 0.06 | 2.229E-05 |
| [Cu2(p-CB-cyclams)(OAc)2][PF6]2 | TJH384A | 1118.030 | 14.590 | 0.11 | 1.305E-05 |
| [Zn2(p-CB-cyclams)(OAc)2][PF6]2 | KS34 | 1121.697 | 15.760 | 0.10 | 1.405E-05 |
| Me1Pic1-CB-cyclen | KRW32 | 303.454 | 14.360 | 0.03 | 4.732E-05 |
| [Co(dcp-SB-cyclam)(OAc)]PF6 | KLC002A | 649.310 | 16.070 | 0.06 | 2.475E-05 |
| [Co(pic-SB-cyclen)Cl]PF6 | KRW45 | 537.782 | 5.200 | 0.15 | 9.669E-06 |
| pic2-CB-cyclen | PW95 | 380.540 | 14.850 | 0.04 | 3.902E-05 |
| [p-(BMBCyclams)]Br2 | SLK17A | 712.568 | 1.317 | 0.77 | 1.848E-06 |
| [p-(DCP-BMBCyclams)]Br4 | SLK26 | 1194.494 | 5.705 | 0.30 | 4.776E-06 |
| [m-(BMBCyclams)]Br2 | DJD05 | 712.568 | 4.213 | 0.24 | 5.912E-06 |
| [Co2(m-cyclam-homocyclen)(OAc)2][PF6]2 | AW049 | 1094.768 | 1.217 | 1.28 | 1.112E-06 |
| [Cu2(m-cyclam-homocyclen)(OAc)1.5][PF6]2.5 | AW051A | 1146.953 | 7.253 | 0.22 | 6.324E-06 |
| [Co(Bn2Cyclam)(OAc)PF6 . H2O | BME07 | 661.215 | 0.597 | 1.57 | 9.029E-07 |
| H2PBCyclam | DJD27 | 240.389 | 3.380 | 0.10 | 1.406E-05 |
| [Co(H2PBCyclam)(OAc)]PF6 . NH4PF6 . H2O | SLK38B | 684.348 | 0.375 | 2.59 | 5.480E-07 |
| Co(Py-SB-Cyclam)Cl2 . 2.2H2O | ADS19 | 486.945 | 5.160 | 0.13 | 1.060E-05 |
| [Co(Bn2PBCyclen)(C2H3O2)]PF6 | AW038 | 655.523 | 5.800 | 0.16 | 8.848E-06 |
| [Ni(Bn2PBCyclen)(C2H3O2)]PF6 | AW039 | 655.283 | 5.030 | 0.18 | 7.676E-06 |
| [Ni2(p-CB-Homocyclens)(OAc)2][PF6]2 | TJH378A | 1080.264 | 5.150 | 0.30 | 4.767E-06 |
| [Cu2(m-CB-Cyclams)(OAc)2][PF6]2 | RM52 | 1118.029 | 4.940 | 0.32 | 4.418E-06 |
| [Ni2(m-CB-Cyclams)(OAc)2][PF6]2 | CDG009 | 1108.315 | 5.150 | 0.31 | 4.647E-06 |

| Sample Code | Sample Code | Molecular Weight | C. glabrata IC$_{50}$ (µg/mL) | X more potent than amphotericin B | C. glabrata IC$_{50}$ (mol/L) |
|---|---|---|---|---|---|
| [Co2(p-SB-Cyclens)(OAc)2][PF6]2 . DMF | OB30 | 1097.737 | 0.800 | 1.95 | 7.288E-07 |
| [Co2(m-SB-Cyclens)(OAc)2][PF6]2 . 2H2O | OB36 | 1060.673 | 3.720 | 0.40 | 3.507E-06 |
| [Co3(tris-SB-Cyclams)(OAc)3][PF6]3 | CDG025 | 1582.068 | 1.500 | 1.50 | 9.481E-07 |
| [Zn3(tris-SB-Cyclams)(OAc)3][PF6]3 . NH4PF6 | CDG026 | 1764.411 | 3.420 | 0.73 | 1.938E-06 |
| [Cu3(tris-SB-Cyclams)(OAc)3][PF6]3 . 1.5NH4PF6 | CDG027 | 1840.411 | 1.630 | 1.60 | 8.857E-07 |
| [Co3(tris-SB-Cyclens)(OAc)3][PF6]3 | CDG021 | 1497.907 | 0.800 | 2.66 | 5.341E-07 |
| [Ni3(tris-SB-Cyclens)OAc)3][PF6]3 . H2O | CDG030 | 1515.193 | 4.170 | 0.52 | 2.752E-06 |
| [Co3(tris-CB-Cyclams)(OAc)1.5][PF6]4.5 | BNS24 | 1753.028 | 1.490 | 1.67 | 8.500E-07 |
| [Cu3(tris-CB-Cyclams)(OAc)3][PF6]3 | BNS25 | 1637.987 | 5.420 | 0.43 | 3.309E-06 |
| [Zn3(tris-CB-Cyclams)(OAc)3][PF6]3 . 2.4NH4PF6 | BNS26 | 2034.696 | 2.140 | 1.35 | 1.052E-06 |
| [Ni3(tris-CB-Cyclens)(OAc)3][PF6]3 . 6H2O | BNS19 | 1647.350 | 4.900 | 0.48 | 2.974E-06 |
| [Co3(tris-CB-Cyclens)(OAc)3][PF6]6 | BNS20 | 1974.880 | 4.720 | 0.59 | 2.390E-06 |
| [Co2(m-SB-cyclam-cyclen)(OAc)2][PF6]4 . H2O | CMB032 | 1360.631 | 1.310 | 1.47 | 9.628E-07 |
| [Co2(p-SB-cyclam-cyclen)(OAc)2][PF6]2 | CMB016A | 1052.696 | 1.100 | 1.36 | 1.045E-06 |
| [Co2(p-CB-cyclam-cyclen)(OAc)2][PF6]2 | CMB027 | 1080.750 | 1.320 | 1.16 | 1.221E-06 |
| [Ni2(p-CB-cyclam-cyclen)(OAc)2][PF6]2 | CMB028 | 1080.264 | 4.490 | 0.34 | 4.156E-06 |
| [Cu2(p-CB-cyclam-cyclen)(OAc)2][PF6]2 | CMB029 | 1089.976 | 4.190 | 0.37 | 3.844E-06 |
| [Zn2(p-CB-cyclam-cyclen)(OAc)2][PF6]3 . 4H2O | CMB030 | 1251.624 | 4.190 | 0.42 | 3.348E-06 |
| [Ni2(bis-SB-C-Ar-NO2)(NO3)4] | SJA236 | 1055.380 | 5.750 | 0.26 | 5.448E-06 |

CERTIFICATE OF CORRECTION (continued)
U.S. Pat. No. 10,927,108 B2

The Middle of Column 37-40 at the top, replace the current Table 6, with:

**TABLE 6: The *in vitro* Inhibitory Activity of the Macrocyclic Compounds Against *P. falciparum***

| Sample Code | Sample Code | Molecular Weight | P. falciparum D6 IC$_{50}$ (µg/mL) | X more potent than chloroquine | P. falciparum D6 IC$_{50}$ (mol/L) | P. falciparum W2 IC50 (µg/mL) | X more potent than chloroquine | P. falciparum W2 IC$_{50}$ (mol/L) |
|---|---|---|---|---|---|---|---|---|
| Chloroquine | CQ | 319.872 | 0.0117 | 1.00 | 3.658E-08 | 0.2170 | 1.00 | 6.784E-07 |
| m-CB-homocyclens HCl salt | OB65B | 990.676 | 0.2921 | 0.12 | 2.948E-07 | 0.3783 | 1.78 | 3.819E-07 |
| p-CB-homocyclens HCl salt | TA22C | 842.229 | 0.2596 | 0.12 | 3.082E-07 | 0.3189 | 1.79 | 3.786E-07 |
| Mn2(p-CB-cyclams)Cl4 | JGL16A | 834.608 | 0.7989 | 0.04 | 9.572E-07 | 0.8002 | 0.71 | 9.588E-07 |
| Bn2Bcyclam | JGL45 | 406.610 | 1.0894 | 0.01 | 2.679E-06 | 0.1772 | 1.56 | 4.358E-07 |
| Mn{Bn2Bcyclam}Cl2 | NS06 | 532.458 | 0.0838 | 0.23 | 1.574E-07 | 0.0674 | 5.36 | 1.266E-07 |
| Fe{Bn2Bcyclam}Cl2 | NS08 | 533.367 | 0.1726 | 0.11 | 3.236E-07 | 0.2271 | 1.59 | 4.258E-07 |
| [Zn(Bn2Bcyclam)(OAc)]PF6 | RM41 | 676.003 | 0.2315 | 0.11 | 3.425E-07 | 0.4010 | 1.14 | 5.932E-07 |
| [Cu(Bn2Bcyclam)(OAc)]PF6 | RM37 | 674.169 | 0.2855 | 0.09 | 4.235E-07 | 0.5451 | 0.84 | 8.086E-07 |
| Mn{Bn2Bcyclen}Cl2 | NS29 | 504.405 | 0.1337 | 0.14 | 2.651E-07 | 0.2747 | 1.25 | 5.446E-07 |
| [Cu(Bn2Bcyclen)(OAc)]PF6 | RM58 | 646.116 | 0.0947 | 0.25 | 1.466E-07 | 0.2015 | 2.18 | 3.119E-07 |
| Fe{Bn1Me1Bcyclam}Cl2 | NS12 | 457.270 | 0.1371 | 0.12 | 2.998E-07 | 0.1164 | 2.67 | 2.546E-07 |
| 4,10-bis(7-chloroquinoline)-1,7-dimethylcyclen | K-PAA-0012-P28 | 523.501 | 0.1169 | 0.16 | 2.233E-07 | 0.1992 | 1.78 | 3.805E-07 |
| Fe-complex-4,10-bis(chloroquinoline)cyclen | K-PAA-0016-P36 | 885.660 | 0.0196 | 1.65 | 2.213E-08 | 0.0336 | 17.88 | 3.794E-08 |
| [Mn(Bn1Me1-CB-Cyclam)Cl2] | NS11 | 456.355 | 0.6142 | 0.03 | 1.346E-06 | 0.5300 | 0.58 | 1.161E-06 |
| {[Mn(4,10-bis(7-chloroquinoline)cyclen]Cl2} | K-PAA2-0004-P8 | 622.200 | 0.0750 | 0.30 | 1.205E-07 | 0.0875 | 4.82 | 1.406E-07 |
| [Fe(Me1Py1-CB-Cyclam)Cl]PF6 | DGJ011 | 567.761 | 0.9983 | 0.02 | 1.758E-06 | 1.0356 | 0.37 | 1.824E-06 |
| [Mn(Bn2PBCyclam)][MnCl4] | BME08 | 672.321 | 0.0967 | 0.25 | 1.438E-07 | 0.1206 | 3.78 | 1.794E-07 |
| [Ni(Bn2PBCyclam)(OAc)]PF6 | DJD22 | 683.344 | 0.7074 | 0.04 | 1.035E-06 | 0.9060 | 0.51 | 1.326E-06 |
| p-H2PBCyclams | SLK10 | 582.911 | 0.8657 | 0.02 | 1.485E-06 | 1.7920 | 0.22 | 3.074E-06 |
| [Ni(Bn2Cyclam)(OAc)]PF6 . H2O | BME06 | 661.287 | 0.7495 | 0.03 | 1.133E-06 | 1.7132 | 0.26 | 2.591E-06 |
| Bn2PBCyclen | AW009 | 392.581 | 1.0770 | 0.01 | 2.743E-06 | 1.5560 | 0.17 | 3.964E-06 |
| [Cu(Bn1Me1Bcyclam)(OAc)]PF6 | RM56A | 598.072 | 0.7145 | 0.03 | 1.195E-06 | 0.6747 | 0.60 | 1.128E-06 |
| [Mn(Bcyclam)Cl2]PF6 | OB15B | 526.818 | 0.5799 | 0.03 | 1.101E-06 | 0.6558 | 0.54 | 1.245E-06 |
| m-CB-cyclams HCl salt | TJS04 | 874.590 | 0.7450 | 0.04 | 8.518E-07 | 0.6558 | 0.90 | 7.498E-07 |

| Sample Code | Sample Code | Molecular Weight | P. falciparum D6 IC$_{50}$ (µg/mL) | X more potent than chloroquine | P. falciparum D6 IC$_{50}$ (mol/L) | P. falciparum W2 IC50 (µg/mL) | X more potent than chloroquine | P. falciparum W2 IC$_{50}$ (mol/L) |
|---|---|---|---|---|---|---|---|---|
| [Ni(Bn2Bcyclam)(OAc)]PF6 | TC09 | 669.32 | 0.552 | 0.04 | 8.247E-07 | 0.8876 | 0.51 | 1.326E-06 |
| Bn2Bcyclen | ANC14 | 378.564 | 0.5110 | 0.03 | 1.35E-06 | 0.7602 | 0.34 | 2.008E-06 |
| Bis-crossbridge-Cyclam | K-PAA2-0009-P18 | 549.544 | 1.148 | 0.02 | 2.089E-06 | 2.1477 | 0.17 | 3.908E-06 |
| Tris-Cyclam | K-PAA2-0016-P32 | 685.094 | 0.0316 | 0.79 | 4.613E-08 | 0.0361 | 12.87 | 5.269E-08 |
| Bis-tridecane | K-AVR-0005-P10-D1 | 509.479 | 0.1508 | 0.12 | 2.96E-07 | 0.1317 | 2.62 | 2.585E-07 |
| Bis-crossbridge-Cyclen | K-PAA2-0023-P46 | 521.49 | 0.1907 | 0.10 | 3.657E-07 | 0.6075 | 0.58 | 1.165E-06 |
| Cu complex of Cyclen bisquinoline | K-AVR-0009-P32 | 677.086 | 0.1732 | 0.14 | 2.558E-07 | 0.5625 | 0.82 | 8.308E-07 |
| Bis-BQ-Cyclen | K-AVR-0008-P30 | 698.561 | 2.1001 | 0.01 | 3.006E-06 | 3.3869 | 0.14 | 4.848E-06 |
| Pentadecane Mono | K-JDD-0011-P36 | 375.945 | 0.0203 | 0.68 | 5.4E-08 | 0.5279 | 0.48 | 1.404E-06 |

CERTIFICATE OF CORRECTION (continued)
U.S. Pat. No. 10,927,108 B2

The middle of Column 41-43 at the top, replace the current Table 9, with:

TABLE 9: Compounds evaluated against NTS *S. mansoni* at 33 µM

| S. No. | Compound ID | Effect at 72h (%) | S. No. | Compound ID | Effect at 72h (%) |
|---|---|---|---|---|---|
| 1 | RM03 | 0.00% | 50 | RM52 | 5.41% |
| 2 | MJG04 | 0.00% | 51 | RM17 | 43.24% |
| 3 | AN06 | 5.41% | 52 | OBO24B | 11.71% |
| 4 | SH6 | 18.02% | 53 | OB28 | 0.00% |
| 5 | ANC21 | 5.41% | 54 | OB29 | 5.41% |
| 6 | ANC20A | 18.02% | 55 | OB30 | 5.41% |
| 7 | DGJ061 | 30.63% | 56 | OB31 | 11.71% |
| 8 | MBA04 | 24.32% | 57 | DJC03 | 36.94% |
| 9 | CNV06 | 0.00% | 58 | DJC04 | 30.63% |
| 10 | MM06 | 18.02% | 59 | DJC05C | 5.41% |
| 11 | NS6 | 11.71% | 60 | DJC06A | 5.41% |
| 12 | DJD50 | 18.02% | 61 | DJC07 | 0.00% |
| 13 | MM05 | 18.02% | 62 | MBA28A | 18.02% |
| 14 | JGL45 | 81.08% | 63 | MBA29A | 11.71% |
| 15 | NS06 | 81.08% | 64 | KS22B | 5.41% |
| 16 | NS08 | 18.02% | 65 | KS24 | 18.02% |
| 17 | TC11 | 24.32% | 66 | KS25 | 18.02% |
| 18 | TC09 | 43.24% | 67 | KS26 | 11.71% |
| 19 | RM37 | 100.00% | 68 | KS27 | 100.00% |
| 20 | RM41 | 100.00% | 69 | BNS009 | 24.32% |
| 21 | AW056 | 5.41% | 70 | BNS017 | 0.00% |
| 22 | ANC14 | 43.24% | 71 | BNS19 | 18.02% |
| 23 | NS29 | 43.24% | 72 | BNS20 | 18.02% |
| 24 | NS30 | 24.32% | 73 | BNS21 | 5.41% |
| 25 | TC12 | 43.24% | 74 | BNS22 | 11.71% |
| 26 | TC10 | 30.63% | 75 | CDG029 | 24.32% |
| 27 | RM58 | 5.41% | 76 | CDG021 | 11.71% |
| 28 | RM42 | 30.63% | 77 | CDG022 | 11.71% |
| 29 | NS11 | 5.41% | 78 | CDG023 | 18.02% |
| 30 | NS12 | 100.00% | 79 | CDG030 | 18.02% |
| 31 | TRH016 | 11.71% | 80 | CDG015 | 5.41% |
| 32 | TRH11B | 24.32% | 81 | BNS018 | 11.71% |
| 33 | RM56A | 18.02% | 82 | BNS023 | 5.41% |
| 34 | RM55A | 30.63% | 83 | BNS024 | 5.41% |
| 35 | KS13 | 30.63% | 84 | BNS025 | 18.02% |
| 36 | KS15 | 11.71% | 85 | BNS026 | 0.00% |
| 37 | JGL08 | 11.71% | 86 | CDG019 | 0.00% |
| 38 | JGL16A | 5.41% | 87 | CDG024 | 5.41% |
| 39 | JGL17A | 100.00% | 88 | CDG025 | 18.02% |
| 40 | KS35 | 30.63% | 89 | CDG026 | 11.71% |
| 41 | KS33 | 0.00% | 90 | CDG027 | 11.71% |
| 42 | TJH384A | 5.41% | 91 | K-PAA2-0002-P3 | 100.00% |
| 43 | RM53 | 0.00% | 92 | K-PAA2-0015-P40 | 100.00% |
| 44 | KBN003 | 36.94% | 93 | K-PAA2-0029-P68 | 43.24% |
| 45 | KS41 | 5.41% | 94 | K-PAA2-0024-P48 | 43.24% |
| 46 | TJS04 | 24.32% | 95 | K-AVR-0005-P10-D1 | 100.00% |
| 47 | CDG009 | 0.00% | 96 | K-PSS-pentadecane | 93.69% |
| 48 | CDG010 | 11.71% | 97 | K-PSS-0001 | 62.16% |
| 49 | RM51 | 0.00% | 98 | K-PAA2-0015-P30 | 100.00% |